(12) United States Patent
Wu et al.

(10) Patent No.: US 10,174,036 B2
(45) Date of Patent: Jan. 8, 2019

(54) SUBSTITUTED PYRAZOLES AS JAK INHIBITORS

(71) Applicant: WUXI FORTUNE PHARMACEUTICAL CO., LTD, Jiangsu (CN)

(72) Inventors: Hao Wu, Shanghai (CN); Peng Li, Shanghai (CN); Weiwei Mao, Shanghai (CN); Shuhui Chen, Shanghai (CN); Fei Wang, Shanghai (CN); Jian Li, Shanghai (CN)

(73) Assignee: WUXI FORTUNE PHARMACEUTICAL CO., LTD, Jiangsu (CN)

( * ) Notice: Subject to any disclaimer, the term of this patent is extended or adjusted under 35 U.S.C. 154(b) by 0 days.

(21) Appl. No.: 15/570,499

(22) PCT Filed: Apr. 26, 2016

(86) PCT No.: PCT/CN2016/080208
§ 371 (c)(1),
(2) Date: Oct. 30, 2017

(87) PCT Pub. No.: WO2016/173484
PCT Pub. Date: Nov. 3, 2016

(65) Prior Publication Data
US 2018/0179209 A1 Jun. 28, 2018

(30) Foreign Application Priority Data
Apr. 29, 2015 (CN) .......................... 2015 1 0213187

(51) Int. Cl.
| | |
|---|---|
| C07D 231/10 | (2006.01) |
| C07D 205/04 | (2006.01) |
| C07D 487/04 | (2006.01) |
| C07D 413/14 | (2006.01) |
| C07D 417/14 | (2006.01) |
| C07D 471/04 | (2006.01) |
| A61K 31/423 | (2006.01) |
| A61K 31/428 | (2006.01) |
| A61K 31/437 | (2006.01) |
| A61K 31/4985 | (2006.01) |
| A61K 31/506 | (2006.01) |
| A61K 31/519 | (2006.01) |

(52) U.S. Cl.
CPC ......... *C07D 487/04* (2013.01); *C07D 413/14* (2013.01); *C07D 417/14* (2013.01); *C07D 471/04* (2013.01); *A61K 31/423* (2013.01); *A61K 31/428* (2013.01); *A61K 31/437* (2013.01); *A61K 31/4985* (2013.01); *A61K 31/506* (2013.01); *A61K 31/519* (2013.01)

(58) Field of Classification Search
CPC .......................... C07D 205/04; C07D 231/10
USPC ............................................. 548/373.1, 953
See application file for complete search history.

(56) References Cited

U.S. PATENT DOCUMENTS

| | | | |
|---|---|---|---|
| 7,301,023 | B2 | 11/2007 | Flanagan et al. |
| 8,808,764 | B2 | 8/2014 | Heaton et al. |
| 2002/0094974 | A1 | 7/2002 | Castelhano et al. |
| 2013/0131039 | A1 | 5/2013 | Burgess et al. |
| 2014/0228349 | A1 | 8/2014 | Boys et al. |

FOREIGN PATENT DOCUMENTS

| | | |
|---|---|---|
| CN | 1489590 A | 4/2004 |
| CN | 1729192 A | 2/2006 |
| CN | 102985424 A | 3/2013 |
| CN | 103987713 A | 8/2014 |
| WO | 2002096909 A1 | 12/2002 |
| WO | 2009047514 A1 | 4/2009 |
| WO | 2010020905 A1 | 2/2010 |
| WO | 2015087201 A1 | 6/2015 |

OTHER PUBLICATIONS

Baxter EJ, et al., "Acquired mutation of the tyrosine kinase JAK2 in human myeloproliferative disorders", Lancet. 2005; 365 (9464): 1054-61.
Berge et al., "Pharmaceutical Salts", Journal of Pharmaceutical Science 66: 1-19 (1977).
Hubert Maehr, "A Proposed New Convention for Graphic Presentation of Molecular Geometry and Topography", J. Chem. Ed. 1985, 62: 114-120.
International Search Report & Written Opinion dated Jun. 30, 2016 from PCT Application No. PCT/CN2016/080208.
Linda M. Scott et al., "JAK2 Exon 12 Mutations in Polycythemia Vera and Idiopathic Erythrocytosis", NEngl J Med 2007;356:459-68.
O Kilpivaara et al., "JAK2 and MPL mutations in myeloproliferative neoplasms: discovery and science", Leukemia (2008) 22, 1813-1817.
Remington, "The Science and Practice of Pharmacy", 21st Ed., Lippincott, Williams & Wilkins (2005).

(Continued)

*Primary Examiner* — Douglas M Willis
(74) *Attorney, Agent, or Firm* — Innovation Capital Law Group, LLP; Vic Lin

(57) ABSTRACT

A compound having the structure of below Formula (I), or pharmaceutically acceptable salts thereof, are useful as JAK inhibitors, wherein $R_1$, $R_2$, $L_1$, $L_2$, T and X are as herein described.

20 Claims, No Drawings

(56) References Cited

OTHER PUBLICATIONS

Vainchenker W, et al., "Constantinescu SNJAKs in pathology: role of Janus kinases in hematopoietic malignancies and immunodeficiencies", Semin Cell Dev Biol 19:385-393 (http://www.sciencedirect.com/science/journal/10849521/19/4?sdc=1).
European Search Report dated Jun. 28, 2018 from European Application No. 16739772.8.
Flanagan et al., "Discovery of CP-690,550: A Potent and Selective Janus Kinase (JAK) Inhibitor for the Treatment of Autoimmune diseases and Organ Transplant Rejection", Journal of Medicinal Chemistry, vol. 53, No. 24, Dec. 23, 2010, pp. 8468-8484.
International Search Report & Written Opinion from corresponding International PCT Application No. PCT/CN2016/071313.
Levy et al., "STAT3 Signaling and the Hyper—IgE Syndrome", N Engl J Med 2007; 357:1655-1658Oct. 18, 2007DOI: 10.1056/NEJMe078197.
O'Shea, "Targeting the JAK/STAT pathway for immonusuppression", Ann Rheum Dis 2004;63(Suppl II):ii67-ii71. doi:10.1136/ard.2004.028290.

SUBSTITUTED PYRAZOLES AS JAK INHIBITORS

FIELD OF THE INVENTION

The present invention relates to a series of JAK inhibitors, in particular to compounds of Formula (I) or pharmaceutically acceptable salts thereof.

BACKGROUND OF THE INVENTION

JAK belongs to a family of tyrosine kinases that are involved in inflammation, autoimmune diseases, proliferative diseases, transplant rejection, diseases involving impairment of cartilage turnover, congenital cartilage malformations and/or diseases associated with hypersecretion of IL6. The present invention also provides methods for the production of the compounds, pharmaceutical compositions comprising the compounds, methods for the prophylaxis and/or treatment of diseases involving inflammation, autoimmune diseases, proliferative diseases, transplant rejection, diseases involving impairment of cartilage turnover, congenital cartilage malformations and/or diseases associated with hypersecretion of IL6 by administering a compound of the present invention.

Janus kinases (JAK) are cytoplasmic tyrosine kinases that transduce cytokine signaling from membrane receptors to STAT transcription factors. Four JAK family members are described in the prior art: JAK1, JAK2, JAK3 and TYK2. Upon binding of the cytokine to its receptor, JAK family members auto- and/or transphosphorylate each other, followed by phosphorylation of STATs and then migrate to the nucleus to modulate transcription. JAK-STAT intracellular signal transduction is suitable for the interferons, most interleukins, as well as a variety of cytokines and endocrine factors such as EPO, TPO, GH, OSM, LIF, CNTF, GM-CSF and PRL (Vainchenker W. et al. (2008)).

The combination of genetic models and small molecule JAK inhibitor research revealed the therapeutic potential of several JAKs. JAK2 gene mutation research is one of the breakthrough progress of hematological research in recent years. Myeloproliferative diseases (MPD) are disclosed in the prior art, including polycythemia vela (PV), essential thrombocythemia (ET) and idiopathicmyelofibrosis (IMF), which are malignant diseases caused by the lesions of a group of hematopoietic stem cell lesion. A JAK2 point mutation (JAK2V617F) in this group of diseases was discovered by the researchers in 2005, which led to a new era in MPD diagnosis and treatment. JAK2V617 is a point mutation that occurs at exon v617 at exon 14, and valine (V) is substituted by phenylalanine (F). In the structure of JAK2, JH1 is the kinase domain; and Val617 is located in JH2 adjacent to JH1, which is a pseudokinase domain, binds to JH1 and inhibits its activation. V617F mutations cause JH2 to lose inhibitory effect on JH1 kinase activity, leading to sustained activation of JAK2, resulting in enhanced cell proliferation [Kilpivaara 0, Levine R L. JAK2 and MPL mutations in myeloprolifer-ative neoplasms: discovery and science. Leukemia. 2008; 22(10):1813-7]. There is a high incidence of JAK2V617F mutation in patients with polycythaemia vera, essential thrombocythaemia, and idiopathic myelofibrosis. It was determined by Allele-Specific PCR that, the incidence of JAK2V617F mutation in patients with polycythaemia vera was 90%; in patients with essential thrombocythaemia and idiopathic myelofibrosis was 50%-60% [Baxter E J, Scott L M, Campbell P J, et al. Lancet. 2005; 365 (9464): 1054-61]. The molecular basis of these diseases without finding JAK2 mutation in patients lacking of V617F mutation is unclear. In 2007, an exon 12 mutation was found in JAK2V617F-negative MPD patients. This mutation can also cause JH2 to lose inhibitory effect on JH kinase activity, which provides molecular markers and genetic mechanisms for JAK2V617F-negative patients with myeloproliferative diseases [Scott L M, Tong W, Levine R L, et al. JAK2 exon 12 mutations in polycythemia vera and idiopathic erythrocytosis. N Engl J Med 2007; 356:459-68-]. In normal physiological conditions, JAK2 mediates signal transduction of various cytokines, including erythropoietin (EPO), thrombopoietin (TPO), granulocyte-macrophage colony stimulating factor, interleukin-3 and growth factor, and regulates and promotes cell proliferation. JAK2 gene plays an important role in adjustment of hematopoietic, and its downstream STAT family is a family of proteins that bind to DNA. The STAT family couples with JAK phosphorylated signaling pathway (JAK-STAT signaling pathway) and play a role in the regulation of transcription. JAK-STAT can directly correlate extracellular signals with gene expression regulation, initiate transcription and expression of responsive genes, complete the signal transduction process of cytokine receptors such as erythropoietin receptor (EPOR) and thrombopoietin receptor (MPL/TPOR), resulting in cell proliferation effects.

Tofacitinib is a pan jak inhibitor, a non-highly specific JAK2 inhibitor, its structural formula is as follows:

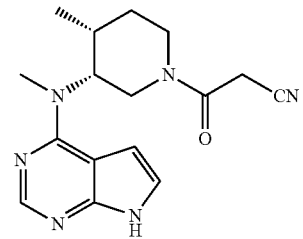

Tofacitinib

BRIEF SUMMARY OF THE INVENTION

It is an object of this invention to provide a compound of Formula (I) or a pharmaceutically acceptable salt thereof,

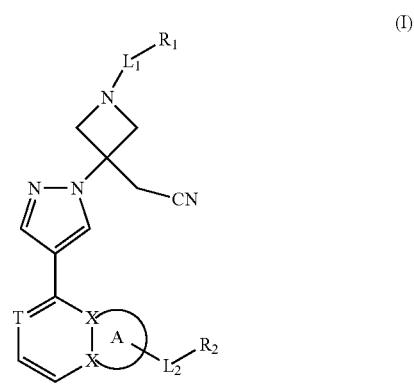

wherein,
$R_1$ is selected from H, or is selected from: $C_{1-6}$ alkyl, $C_{1-6}$ heteroalkyl, $C_{3-7}$ cycloalkyl, 3-7 membered heterocloalkyl, 5-6 membered aryl, 5-6 membered heteroaryl,

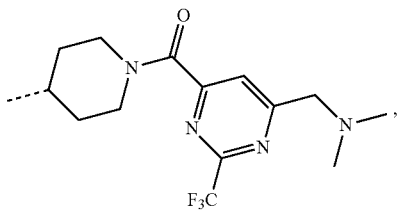

which can be optionally substituted with 1, 2, 3, or 4 R;

L$_1$, L$_2$ are independently selected from a single bond, —S(=O)$_2$—, —S(=O)—, —C(=O)—, —NHC(=O)—;

R$_2$ is selected from H, or is selected from NH$_2$, C$_{1-6}$ alkyl, C$_{1-6}$ heteroalkyl, C$_{3-7}$ cycloalkyl, 3-7 membered heterocycloalkyl, 5-6 membered aryl, 5-6 membered heteroaryl, which can be optionally substituted with 1, 2, 3, or 4 R;

ring A is selected from 5-6 membered heteroaryl;

X is independently selected from N, C;

T is selected from N or C(R);

R is selected from H, halogen, NH2, CN, OH, or is selected from C$_{1-3}$ alkyl, C$_{1-3}$ heteroalkyl, C$_{3-6}$ cycloalkyl, 3-6 membered heterocycloalkyl, 5-6 membered aryl, 5-6 membered heteroaryl, which can be optionally substituted with 1, 2, 3, or 4 R';

R' is selected from halogen, OH, CN, NH2;

the "hetero" represents heteroatoms or heterogroups, and is independently selected from O, S, N, C(=O), S(=O) or S(=O)$_2$;

the number of heteroatoms or heterogroups atoms is independently selected from 0, 1, 2, 3, or 4.

In one embodiment of the invention, R is independently selected from H, halogen, OH, NH$_2$, CN, or is selected from C$_{1-3}$ alkyl, C$_{1-3}$ alkoxy, C$_{1-3}$ alkylamino, which can be optionally substituted with 1, 2, 3, or 4 R'.

In one embodiment of the invention, R is selected from H, F, Cl, Br, I, OH, CN, NH$_2$, Me, Et, N(CH$_3$)$_2$, NH(CH$_3$).

In one embodiment of the invention, R$_1$ is selected from H, or is selected from C$_{1-3}$ alkyl, C$_{3-6}$ cycloalkyl, C$_{3-6}$ heterocycloalkyl, C$_{1-3}$ alkyl-O—C$_{1-3}$ alkyl-, C$_{1-3}$ alkyl-S—C$_{1-3}$ alkyl-, C$_{1-3}$ alkyl-NH—C$_{1-3}$ alkyl-, C$_{1-6}$ alkoxy, C$_{1-3}$ alkylamino,

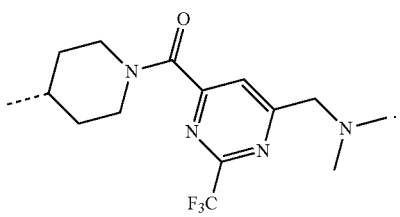

In one embodiment of the invention, R$_1$ is selected from H, or is selected from Me,

which is optionally substituted with 1, 2, 3, or 4 R.

In one embodiment of the invention, R$_1$ is selected from H, Me,

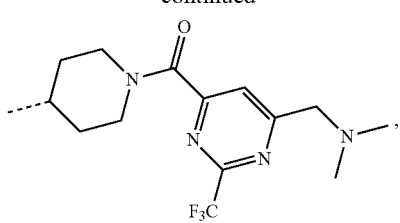

In one embodiment of the invention, R$_1$-L$_1$- is selected from H, or is selected from

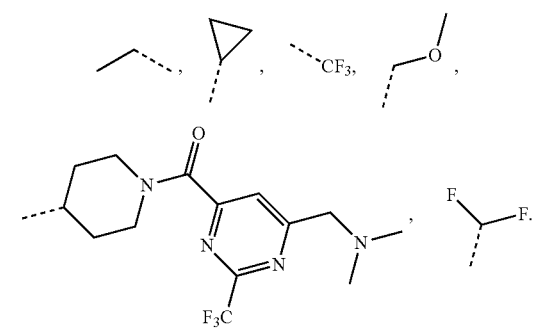

which can be optionally substituted with R.

In one embodiment of the invention, R$_1$-L$_1$- is selected from H,

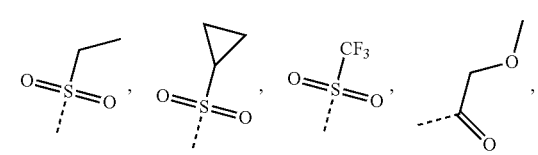

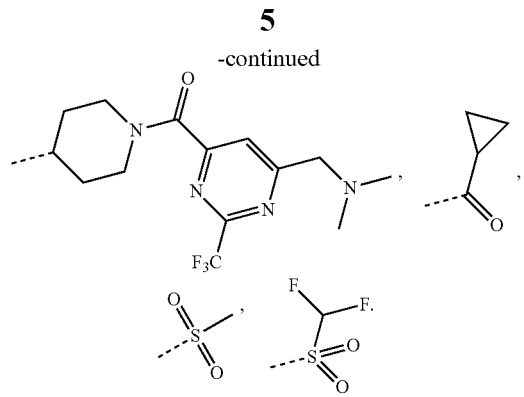

In one embodiment of the invention, $R_2$ is selected from H, $NH_2$, or is selected from $C_{1-3}$ alkyl, $C_{3-6}$ cycloalkyl, 3-6 membered heterocycloalkyl, $C_{1-3}$ alkyl-O—$C_{1-3}$ alkyl-, $C_{1-3}$ alkyl-S—$C_{1-3}$ alkyl-, $C_{1-3}$ alkyl-NH—$C_{1-3}$ alkyl-, $C_{1-6}$ alkoxy, $C_{1-6}$ alkylamino, which can be optionally substituted with R.

In one embodiment of the invention, $R_2$ is selected from H, $NH_2$, or is selected from Me,

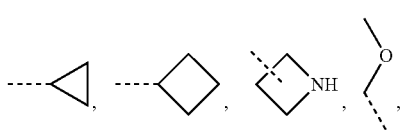

which can be optionally substituted with R.

In one embodiment of the invention, $R_2$ is selected from H, $NH_2$,

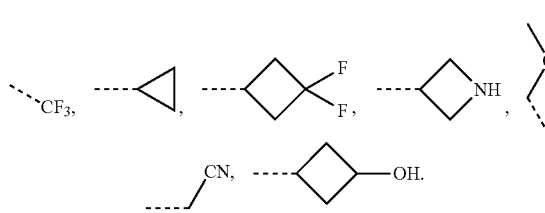

In one embodiment of the invention, $R_2$-$L_2$- is selected from H, or is selected from $NH_2$,

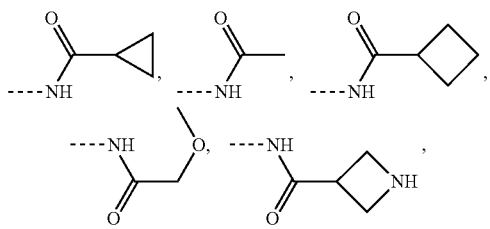

which can be optionally substituted with R'.

In one embodiment of the invention, $R_2$-$L_2$- is selected from H, $NH_2$,

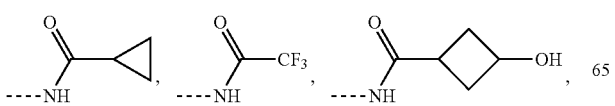

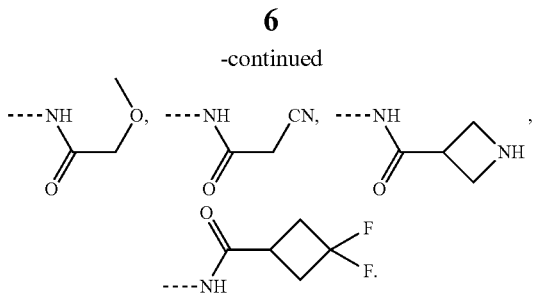

In one embodiment of the invention, the ring A is selected from 1,3,4-triazolyl, imidazolyl, oxazolyl, thiazolyl.

In one embodiment of the invention, the ring A is selected from:

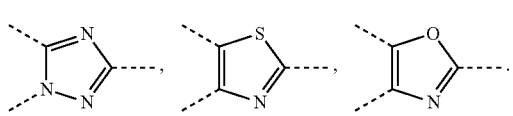

In one embodiment of the invention, the structural unit

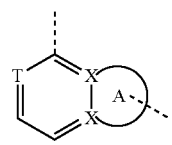

is selected from:

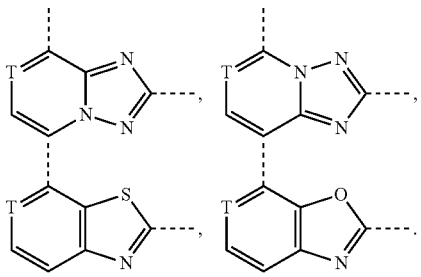

In one embodiment of the invention, the structural unit

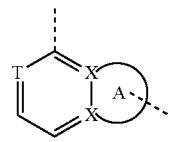

is selected from:

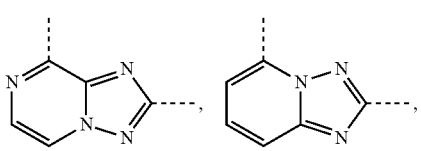

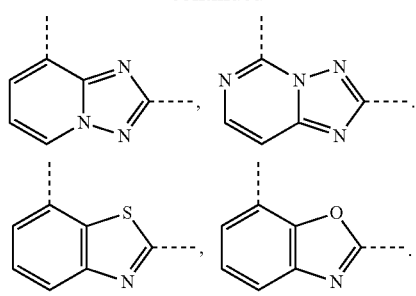
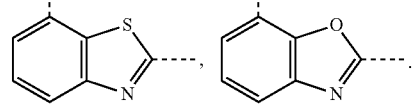
The compound of the invention is selected from:
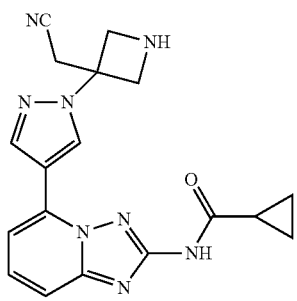
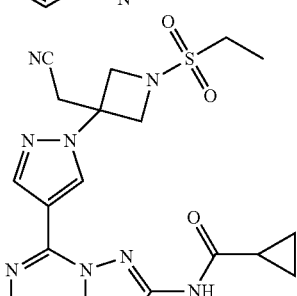
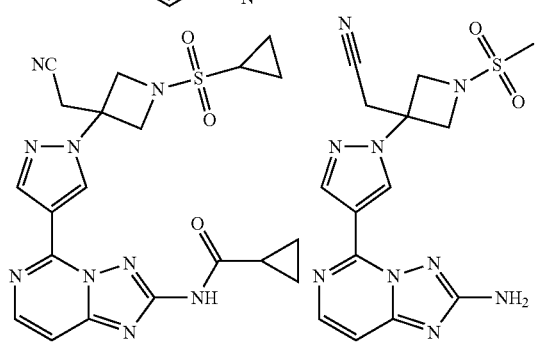
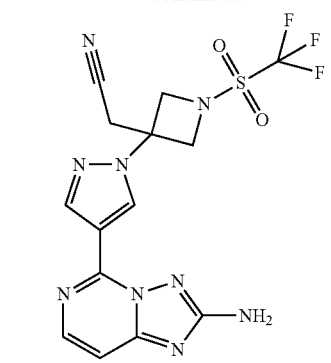
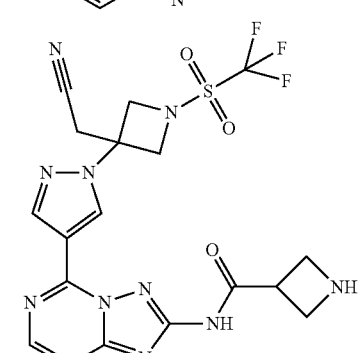
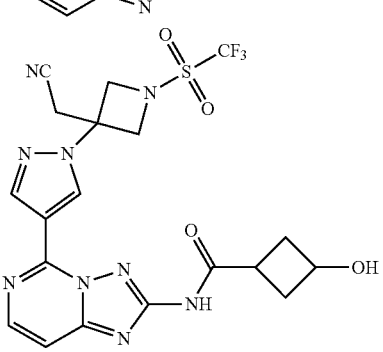
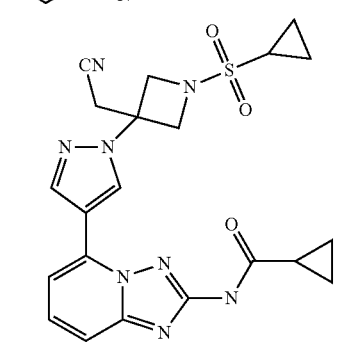
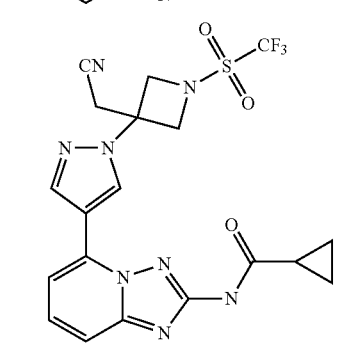

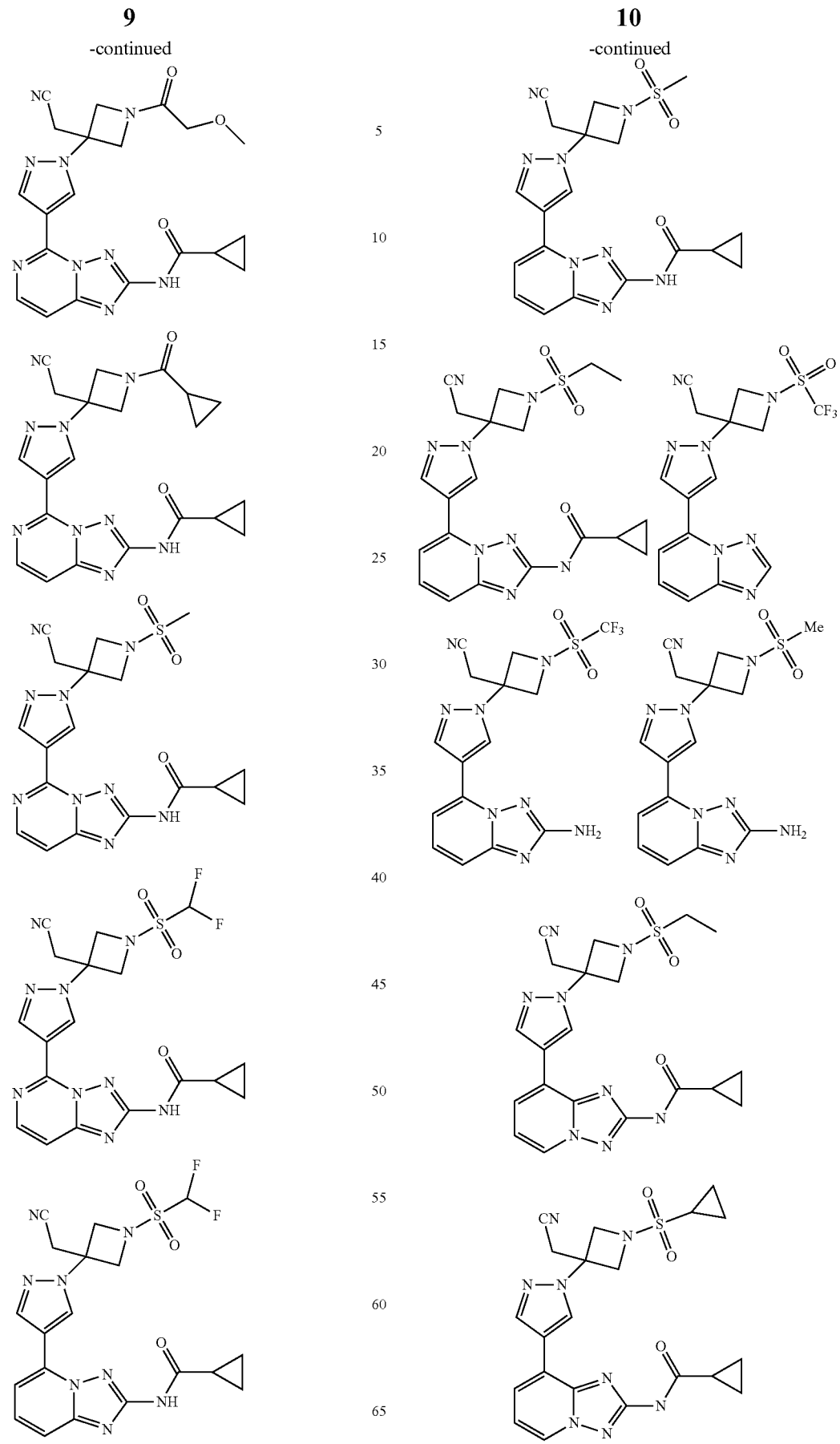

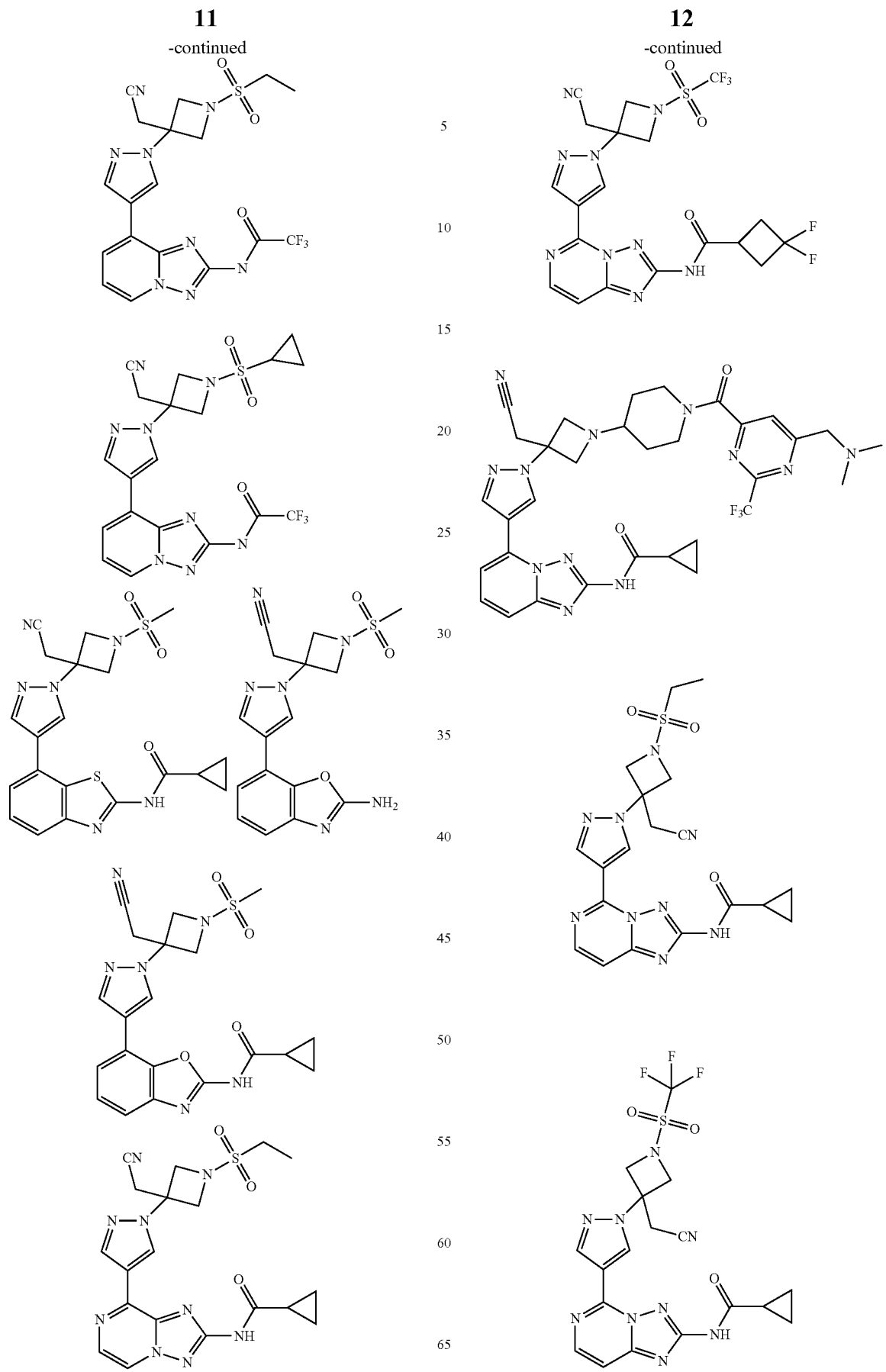

-continued

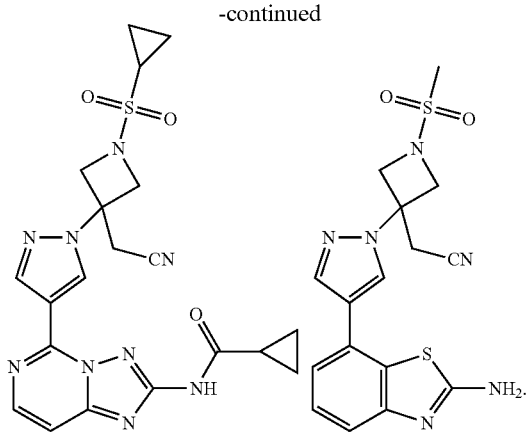

Definitions

Unless specified otherwise, the following terms and phrases used herein are intended to have the following meanings. A specific term or phrase should not be considered to be uncertain or unclear without specific definition, but should be understood in its general meanings. When a trade name appears herein, it is intended to refer to its corresponding commodity or its active ingredient.

$C_{1-6}$ is selected from $C_1$, $C_2$, $C_3$, $C_4$, $C_5$, and $C_6$; $C_{3-7}$ is selected from $C_3$, $C_4$, $C_5$, $C_6$, and $C_7$; 3-7 membered is selected from 3-membered, 4-membered, 5-membered, 6-membered, and 7-membered.

As used herein, the term "pharmaceutically acceptable" is employed to refer to those compounds, materials, compositions and/or dosage forms which are, within the scope of reliable medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" refers to salts of the compound of the present invention, which are prepared from the compounds having particular substituent found by the present invention with relatively nontoxic acids or bases. When compounds of the present invention contain relatively acidic functionalities, base addition salts can be obtained by contacting a sufficient amount of the base with the neutral form of such compounds, either in a neat solution or in a suitable inert solvent. The pharmaceutically acceptable base addition salts include sodium, lithium, calcium, ammonium, organic ammonium, magnesium, and the like. When compounds of the present invention contain relatively basic functionalities, acid addition salts can be obtained by contacting a sufficient amount of the acid with the neutral form of such compounds, either in a neat solution or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic acids and the like (see, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

Preferably, the neutral forms of the compounds may be regenerated by contacting the salt with a base or acid and isolating the parent compound in the conventional manner. The parent form of the compound differs from the various salt forms in certain physical properties, such as solubility in polar solvents.

As used herein, "pharmaceutically acceptable salts" belongs to derivatives of the disclosed compounds wherein the parent compound is modified by converting an existing acid or base to its salt form. Examples of pharmaceutically acceptable salts include, but not limited to, inorganic or organic acid salts of basic residues such as amines; alkali or organic salts of acidic residues such as carboxylic acids, and the like. The pharmaceutically acceptable salts include the conventional non-toxic salts or the quaternary ammonium salts of the parent compounds formed, for example, from non-toxic inorganic or organic acids. For example, such conventional non-toxic salts include, but not limited to, those derived from salts of inorganic or organic acids selected from 2-acetoxybenzoic, 2-hydroxyethane sulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, hydrobromic, hydrochloric, hydroiodic, hydroxy, hydroxynaphthoic, isethionic, lactic, lactobionic, lauryl sulfonic, maleic, malic, mandelic, methane sulfonic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and p-toluenesulfonic acids.

The pharmaceutically acceptable salts of the present invention can be synthesized from the parent compound which contains an acidic or basic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, iso-propanol, or acetonitrile are preferred.

In addition to salt forms, the compounds provided by the present invention are also in the form of prodrugs. The prodrugs of the compounds described herein are those compounds that readily undergo chemical changes under physiological conditions to convert to the compounds of the present invention. Additionally, prodrugs can be converted to the compounds of the present invention by chemical or biochemical methods in vivo environment.

The compounds of the present invention can exist in unsolvated forms as well as solvated forms, which including hydrated forms. In general, the solvated forms are equivalent to unsolvated forms and are intended to be encompassed within the scope of the present invention.

Certain compounds of the present invention possess asymmetric carbon atoms (optical centers) or double bonds. The racemates, diastereomers, geometric isomers and individual isomers are all intended to be encompassed within the scope of the present invention.

The graphic representations of racemic, ambiscalemic and scalemic or enantiomerically pure compounds used herein are taken from: Maehr, J. Chem. Ed. 1985, 62: 114-120. Unless specified otherwise, wedges and broken lines are used to denote the absolute configuration of a stereocenter.

When the compounds described herein contain olefinic double bonds or other centers of geometric asymmetry, and unless specified otherwise, it is intended to include both E and Z geometric isomers. All tautomers are encompassed by the present invention as well.

The compounds of the present invention may exist in particular geometric or stereoisomeric forms. The present invention takes into account all such compounds, including cis- and trans isomers, (−)- and (+)-pair enantiomers, R- and S-enantiomers, diastereomers, (D)-isomers, (L)-isomers, the racemic mixture thereof, such as the enriched mixture of either the enantiomers or the diastereomers, as being covered within the scope of this invention. Additional asymmetric carbon atoms may be present in a substituent such as an alkyl group. All such isomers, as well as mixtures thereof, are intended to be included in this invention.

Optically-active R- and S-enantiomers, and (D)-, and (L)-isomers may be prepared by chiral synthesis, or by chiral reagents, or by any other conventional techniques. If an enantiomer of a certain compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by resolution means well known in the art, and subsequent recovery of the pure enantiomers. Additionally, the separation of the enantiomers and diastereomers can be generally accomplished by using chromatography which using chiral stationary phase and optionally in combination with a chemical derivatization method (e.g. the formation of carbamates from amines).

The compounds of the present invention may also contain unnatural proportions of atomic isotopes at one or more of the atoms that constitute such compounds. For example, the compounds may be labeled by using radioactive isotopes, such as tritium ($^3$H), iodine-125 ($^{125}$I), or carbon-14 ($^{14}$C). All isotopic variations of the compounds of the present invention, whether radioactive or not, are intended to be encompassed within the scope of the present invention.

The term "pharmaceutically acceptable carriers" refers to any formulation or carrier medium capable of delivering an effective amount of the active substance of the present invention without interfering with the biological activity of the active substance and having no toxic side effects to the host or patient. The representative carriers include water, oils, vegetables and minerals, cream base, lotion matrix, ointment matrix, and the like. These matrices include suspending agents, tackifiers, transdermal enhancers, and the like, the formulations of which are well known to those skilled person in the art of cosmetics or local medicines. Regarding additional information about the carriers, refer to the content in "Remington: The Science and Practice of Pharmacy, 21st Ed., Lippincott, Williams & Wilkins (2005)" which are hereby incorporated by reference.

The term "excipient" generally refers to the carrier, diluent and/or medium required by preparation of an effective pharmaceutical composition.

For the drug or pharmacologically active agent, the term "effective amount" or "therapeutically effective amount" refers to a nontoxic but sufficient amount of the drug or agent to provide the desired effect. For the oral dosage in the present invention, the "effective amount" of an active substance in the composition refers to the amount required to achieve the desired effect when used in combination with another active substance in the composition. The effective amount will vary from subject to subject, depending on the age and general condition of the individual, depending on the particular active agent as well. Thus, it is not always possible to specify an exact "effective amount". However, an appropriate "effective" amount in any individual case may be determined by one of ordinary skill in the art in accordance with conventional experimentation.

The terms "active ingredient", "therapeutic agent", "active substance" or "active agent" mean a chemical entity which is effective in treating a target disorder, disease or condition.

The term "substituted" means that any one or more hydrogen atoms on the designated atom is replaced with substituent, provided that the designated atom's valency is normal, and that the substitution results in a stable compound. When the substituent is keto (i.e., =O), then two hydrogen atoms are substituted. Keto substituents are not present on aromatic moieties. The term "optionally substituted" means that it may be substituted or may not be substituted, unless specified otherwise, the type and number of substituents may be optionally on the chemically achievable basis.

When any variable (e.g., R) occurs more than one time in constituent or formula for a compound, its definition at each occurrence is independent. Thus, for example, if a group is shown to be substituted with 0-2 R, then said group may optionally be substituted with up to two R groups and R at each occurrence is selected independently from the definition of R. Also, combinations of substituents and/or variables are permissible only if such combinations result in stable compounds.

When one of the variables is selected from a single bond, it indicates that the two groups to which they are attached are directly connected, for example, when L in A-L-Z represents a single bond, the structure is actually A-Z.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds. For example, the structural unit

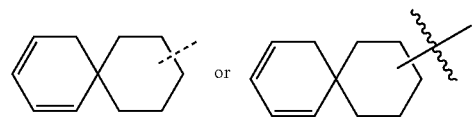

indicates that it can be substituted at any position on the cyclohexyl group or the cyclohexadiene group.

Substituents for the alkyl, and heteroalkyl radicals are generally referred to as "alkyl substituents", and they can be one or more of the following groups selected from, but not limited to: —R', —OR', =O, =NR', =N—OR', —NR'R", —SR', halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR''''—C(NR'R" R' ")=NR'''', NR''''C(NR'R")=NR''', —S(O)R', —S(O)$_2$R', —S(O)2NR'R", NR"SO$_2$R', —CN, —NO$_2$, —N$_3$, —CH(Ph)2, and fluoro(C$_1$-C$_4$)alkyl in a number ranging from zero to (2m'+1), wherein m' is the total number of carbon atoms in such radical. R', R", R'", R"" and R"'" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or aryalkyl groups. When a compound of the present invention includes more than one R group, for example, each of the R groups is independently selected as are each R', R", R'", R"" and R"'" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents", and are selected from, for example: —R', —OR', —NR'R", —SR', -halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR"'"—C(NR'R"R'")=NR"", NR"'"C(NR'R")=NR"', —S(O)R', —S(O)$_2$R', —S(O)$_2$NR'R", NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of pen valences on the aromatic ring system; and where R', R", R'", R"" and R"'" are preferably independently selected from hydrogen, substituted or unsubstituted alkyl, substituted or unsubstituted heteroalkyl, substituted or unsubstituted aryl, and substituted or unsubstituted heteroaryl. When a compound of the present invention includes more than one R group, for example, each of the R groups is independently selected as are each R', R", R'", R"" and R"'" groups when more than one of these groups is present.

Unless specified otherwise, two of the aryl substituents on adjacent atoms of the aryl or heteroaryl ring may optionally be replaced with a substituent of the formula -T-C(O)—(CRR')$_q$—U—, wherein T and U are independently selected from —NR—, —O—, CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. Optionally, one of the single bonds of the new ring so formed may be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, NR'—, —S—, —S(O)—, —S(O)$_2$—, or —S(O)$_2$NR'—. The substituent R, R', R" and R'" are preferably independently selected from hydrogen or substituted or unsubstituted (C$_1$-C$_6$) alkyl.

The terms "halo" or "halogen", by themselves of as part of another substituent, mean, unless specified otherwise, a fluorine, chlorine, bromine, or iodine atom. Additionally, terms such as "haloalkyl", are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. C$_{1-6}$ alkoxy includes the alkoxy of C$_1$, C$_2$, C$_3$, C$_4$, C$_5$ and C$_6$. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. C$_{3-7}$ cycloalkyl includes the cycloalkyl of C$_3$, C$_4$, C$_5$, C$_6$ and C$_7$. "Alkenyl" is intended to include hydrocarbon chains of either a straight or branched configuration and one or more carbon-carbon double bonds which may occur in any stable point along the chain, such as ethenyl and propenyl.

The terms "halo" or "halogen" as used herein refers to fluoro, chloro, bromo, and iodo.

Unless specified otherwise, the term "hetero" means a heteroatom or heteroatom radical (i.e., an atomic radical containing a heteroatom), including atoms other than carbon (C) and hydrogen (H), and atomic radical containing such heteroatoms, for example, including oxygen (O), nitrogen (N), sulfur (S), silicon (Si), germanium (Ge), aluminum (Al), boron (B), —O—, —S—, =O, =S, —C(=O)O—, —C(C=O)—, —S(=O), —S(=O)$_2$—, and optionally substituted —C(=O)N(H)—, —N(H)—, —C(=NH)—, —S(=O)$_2$N(H)— or —S(=O)N(H)—.

Unless specified otherwise, "cyclo" refers to a substituted or unsubstituted cycloalkyl, heterocycloalkyl, cycloalkenyl, heterocycloalkenyl, cycloalkynyl, heterocycloalkynyl, aryl or heteroaryl. The ring includes monocyclic ring, bicyclic ring, spiro ring, or bridged ring. The number of atoms on the ring is usually defined as the number of membered ring, for example, "5- to 7-membered ring" refers to the surrounding arrangement of 5 to 7 atoms. Unless specified otherwise, the ring optionally contains from 1 to 3 heteroatoms. Thus, the term "5- to 7-membered ring" includes such as phenyl, pyridyl and piperidinyl. On the other hand, the term "5- to 7-membered heterocycloalkyl ring" includes pyridyl and piperidinyl, but does not include phenyl. The term "cyclo" also includes cyclic system containing at least one ring, in which each "cyclo" independently meets the above definition.

Unless specified otherwise, the term "heterocycle" or "heterocyclic group" is intended to mean a stable monocyclic or bicyclic or tricyclic ring, including heteroatom or heteroatom radical, which is saturated, partially unsaturated or fully unsaturated (aromatic), and which consists of carbon atoms and from 1, 2, 3 or 4 cyclic heteroatoms independently selected from the group consisting of N, O and S; and including any bicyclic group in which any of the above-defined heterocyclic rings is fused to a benzene ring. The nitrogen and sulfur heteroatoms may optionally be oxidized (NO, and S(O)p). The nitrogen atom may be substituted or unsubstituted (i.e., N or NR, wherein R is H or other substituents already defined herein). The heterocyclic ring may be attached to its pendant group at any heteroatom or carbon atom which results in a stable structure. The heterocyclic ring described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl group" is intended to mean a stable 5, 6, 7-membered monocyclic or bicyclic or 10-membered bicyclic heterocyclic aromatic ring, and which consists of carbon atoms and from 1, 2, 3 or 4 cyclic heteroatoms independently selected from the group consisting of N, O and S. The nitrogen atom may be substituted or unsubstituted (i.e., N or NR, wherein R is H or other substituents already defined herein). The nitrogen and sulfur heteroatoms may optionally be oxidized (NO, and S(O)p). It is noted that the total number of S and O atoms in the aromatic heterocycle is not more than 1. Bridged rings are also included in the definition of heterocycle. A bridged ring forms when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. In bridged ring, the substituents recited for the ring may also be present on the bridge.

Examples of heterocyclic compounds include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, pyranyl, isoindolyl, isoindolinyl, indolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isooxazolyl, hydroxyindolyl, pyrimidyl, phenanthridinyl, phenanthrolinyl, phenazinyl, phenothiazinyl, phenoxazinyl, benzoxanthinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2H-pyrrolyl, pyrrolyl, pyrazolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolothienyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds.

The term "hydrocarbyl" or the specific term thereof (such as alkyl, alkenyl, alkynyl, phenyl, and the like), by itself or as part of another substituent, means, unless specified otherwise, a straight or branched chain, or cyclic hydrocarbon radical, or combination thereof, which may be fully saturated, mono- or polyunsaturated and may be mono-, di-, or poly-substituted, and may be monovalent (such as methyl), divalent (such as methylene), or multivalent (such as methenyl), and can include di- and multivalent radicals, having the number of carbon atoms designated (i.e. $C_1$-$C_{10}$ means one to ten carbons). "Hydrocarbyl" includes, but is not limited to, aliphatic and aromatic hydrocarbon. The aliphatic hydrocarbon includes linear and cyclic hydrocarbon, which specifically includes, but is not limited to, alkyl, alkenyl, alkynyl. The aromatic hydrocarbon includes, but is not limited to, 6- to 12-membered aromatic hydrocarbon, such as phenyl, naphthyl, and the like. In some embodiments, the term "hydrocarbyl" means a straight or branched chain radical, or combination thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, isobutyl, cyclohexyl, (cyclohexyl)methyl, cyclopropylmethyl, homologs and isomers of, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless specified otherwise, the term "heterohydrocarbyl" or the specific term thereof (such as heteroalkyl, heteroalkenyl, heteroalkynyl, heterophenyl, and the like), by itself or in combination with another term, means, a stable straight or branched chain, or cyclic hydrocarbon radical, or combinations thereof, consisting of a number of carbon atoms and at least one heteroatom. In some embodiments, the term "heteroalkyl", by itself or in combination with another term, means, a stable straight or branched chain, or cyclic hydrocarbon radical, or combinations thereof, consisting of a number of carbon atoms and at least one heteroatom. In a representative embodiment, the heteroatom is selected from the group consisting of B, O, N, and S, and wherein the nitrogen and sulfur atoms may optionally be oxidized and the nitrogen heteroatom may optionally be quaternized. The heteroatom or heteroatom radical may be placed at any interior position of the heteroalkyl group (including at the position at which the hydrocarbyl group is attached to the remainder of the molecule). Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms may be consecutive, such as —$CH_2$—NH—$OCH_3$.

Unless specified otherwise, the terms "alkoxy", "alkylamino" and "alkylthio" (or thioalkoxy) are used in their conventional sense, and refers to those alkyl groups attached to the remainder of the molecule via an oxygen atom, an amino group or a sulfur atom, respectively.

Unless specified otherwise, the terms "cyclohydrocarbyl" and "heterocyclohydrocarbyl" or the specific term thereof (such as aryl, heteroaryl, cycloalkyl, heterocycloalkyl, cycloalkenyl, heterocycloalkenyl, cycloalkynyl, heterocycloalkynyl, and the like), by themselves or in combination with other terms, represent, cyclic versions of "hydrocarbyl" and "heterohydrocarbyl", respectively. Additionally, for heterohydrocarbyl or heterocyclohydrocarbyl (such as heteroalkyl, heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocyclic radicals include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran indole-3-yl, tetrahydrothien-2-yl, tetrahydrothien-3-yl, 1-piperazinyl, 2-piperazinyl, and the like.

The term "aryl" means, unless specified otherwise, a polyunsaturated, aromatic, hydrocarbon substituent, which may be mono-, di-, or poly-substituted, and may be monovalent, divalent, or multivalent, and which can be a single ring or multiple rings (such as 1 to 3 rings; wherein at least one ring is the aromatic) which are fused together or linked covalently. The term "heteroaryl" refers to aryl groups (or rings) that contain from one to four heteroatoms. In one exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "aryl" when used in combination with other terms (e.g. aryloxy, arylthioxy, arylalkyl) includes both aryl and heteroaryl rings as defined above. Thus, the terms "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy) propyl, and the like).

The term "leaving group" means a functional group or atom which can be displaced by anther functional group or atom through a substitution reaction, such as a nucleophilic substitution reaction. By way of example, representative leaving groups include trifluoromethanesulfonate; chloro, bromo and iodo groups; sulfonic ester groups, such as mesylate, tosylate, brosylate, p-toluenesulfonate and the like; and acyloxy groups, such as acetoxy, trifluoroacetoxy and the like.

The term "protecting groups" include, but are not limited to "amino-protecting group", "hydroxyl-protecting group", and "thiol-protecting group". The term "amino-protecting group" means a protecting group suitable for preventing said reactions at N position of an amino group. Representative amino-protecting groups include, but not limited to, formyl; acyl, for example, alkane acyl, such as acetyl, trichloroacetyl or trifluoroacetyl;

alkoxycarbonyl, such as tert-butoxycarbonyl (Boc); aryl methoxycarbonyl, such as benzyloxycarbonyl (Cbz), 9-fluorenylmethoxycarbonyl (Fmoc), aryl methyl, such as benzyl (Bn), trityl (Tr), 1,1-di(4'-methoxyphenyl) methyl; siliyl such as trimethylsilyl (TMS), tert-butyldimethylsilyl (TBS), and the like. The term "hydroxyl-protecting group" means a protecting group suitable for preventing said reactions at a carboxy group. Representative hydroxyl-protecting groups include, but are not limited to, alkyl, such as methyl, ethyl, and tert-butyl; acyl, for example, alkane acyl, such as acetyl; aryl methyl, such as benzyl (Bn), p-methoxybenzyl (PMB), 9-fluroenylmethyl (Fm), benzhydryl (diphenyl-methyl, DPM); siliyl, such as trimethylsilyl (TMS), tert-butyldimethylsilyl (TBS), and the like.

The compounds of the present invention can be prepared in a number of synthetic methods well known to one person skilled in the art. The methods includes the specific embodiments described below; the embodiments formed by the combination with the following embodiments and other chemical synthesis methods; and the substitution to the same methods well known to those skilled in the art. The preferred embodiments include, but are not limited to, the examples of the present invention.

The solvents used in the present invention are commercially available. And the following abbreviations are used in the present invention: aq represents water; HATU represents O-(7-azabenzotriazol-1-yl)-N,N,N',N'-tetramethyluronium hexafluoro phosphate, EDC represents N-(3-dimethylaminopropyl)-N'-ethylcarbodiimide hydrochloride; eq represents equivalent, equal quantity; CDI represents carbonyl diimidazole; DCM represents dichloromethylene; PE represents petroleum ether; DIAD represents diisopropyl azodicarboxylate; DMF represents N, N-dimethylformamide; DMSO represents dimethyl sulfoxide; EtOAc represents ethyl acetate; EtOH represents ethanol; MeOH represents methanol; CBz represents benzyloxycarbonyl and is an amine-protecting group; BOC represents tert-butoxycarbonyl and is an amine-protecting group; HOAc represents acetic acid; NaCNBH$_3$ represents Sodium cyanoborohydride; r.t. represents room temperature; O/N represents overnight; THF represents tetrahydrofuran; Boc$_2$O represents di-t-butyldicarbonate; TFA represents trifluoroacetic acid; DIPEA represents diisopropylethylamine; TsOH represents p-toluenesulfonic acid; NFSI represents N-fluoro-N-(benzenesulfonyl) benzenesulfonamide; NCS represents 1-chloropyrrolidine-2,5-dione; n-Bu$_4$NF represents tetrabutylammonium fluoride; iPrOH represents 2-propanol; mp represents melting point; LDA represents Lithium diisopropylamide, MsCl represents methylsulfonyl chloride; THF represents tetrahydrofuran; Pd(dppf)Cl$_2$ represents [1,1'-bis (diphenylphosphino)ferrocene]dichloropalladium(II); DBU represents 1.8-diazabicyclo-undec-7-ene; TFA represents trifluoroacetic acid; EtOAc or EA represents ethyl acetate; EDCI represents N-(3-dimethylaminopropyl)-N'-ethyl carbodiimide hydrochloride; DMAP represents 4-dimethylaminopyridine; DIEA represents diisopropylamine; MTBE represents methyl tert-butyl ether; BnBr represents benzyl bromide; DAST represents di ethyl aminosulfurtrifluoride.

The compounds are named by handwork or ChemDraw® software, and the commercially available compounds are used with the supplier catalog name.

Advantages

The selectivity of the compounds of the present invention for JAK2 is superior to that of Tofacitinib.

DETAILED DESCRIPTION OF THE EMBODIMENTS

Preparation of Intermediate Compounds

Preparation of the Intermediates 1-5

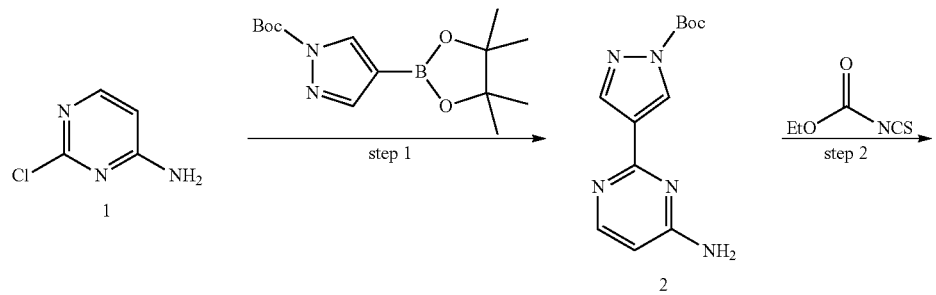

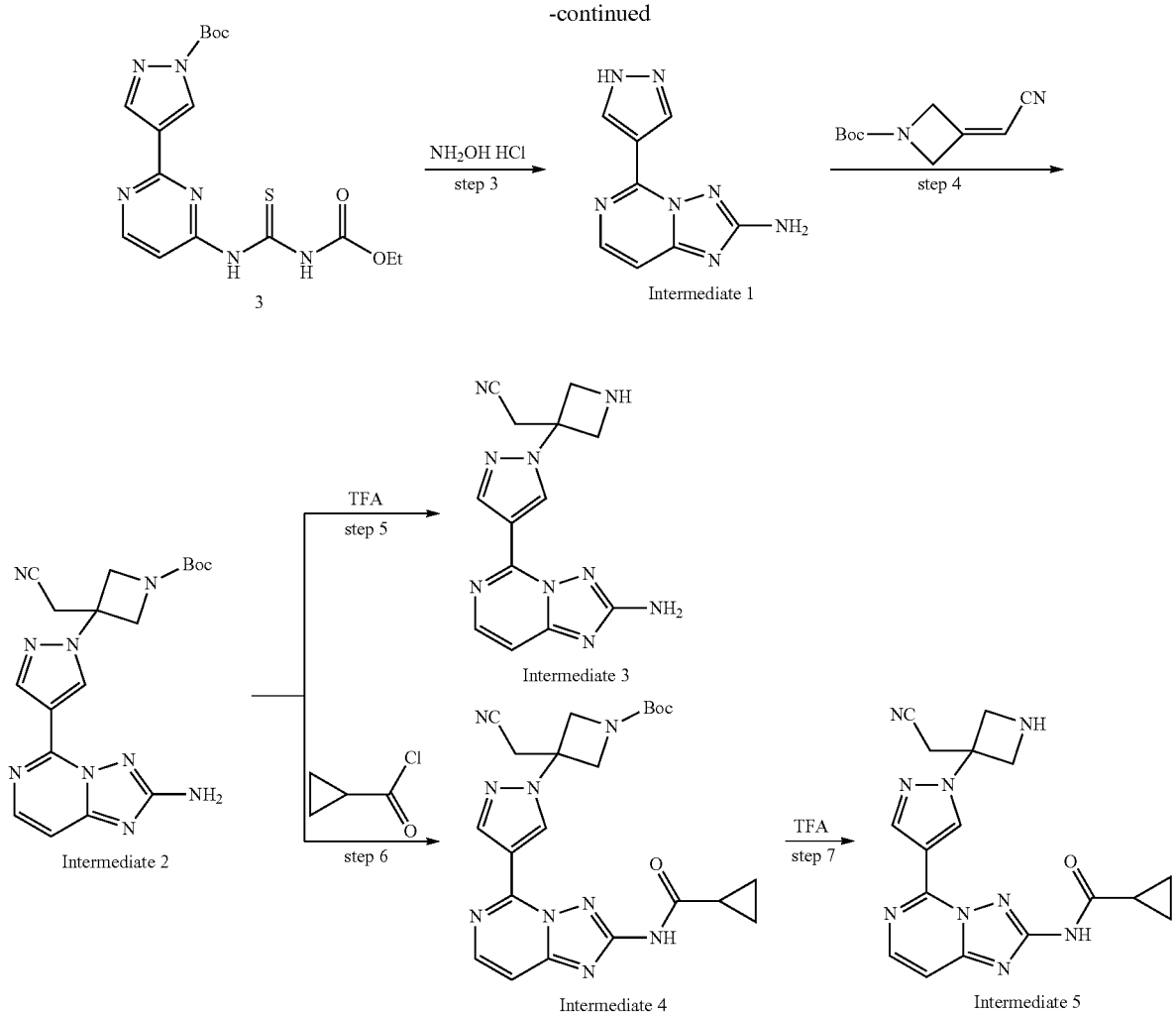

Step 1: Preparation of tert-butyl 4-(4-amidopyrimidinyl-2-yl) pyrazole-1-carboxylate (2)

2-chloro-4-aminopyrimidine (3.0 g, 23.2 mmol), tert-butyl 4-(4,4,5,5-tetramethyl-1,3,2-dioxaborolan-2-yl) pyrazol-1-carboxylic ester (8.2 g, 27.8 mmol), and potassium carbonate (9.6 g, 69.5 mmol) were dissolved in the mixed solvent of dioxane (30 mL) and water (5 mL). Then Pd(dppf)Cl$_2$ (1.7 g, 2.3 mmol) was added. It was vacuumed and purged with nitrogen. The reaction mixture was stirred at 80° C. in an oil bath for 2 hours under the protection of nitrogen, and the complete reaction was tracked and determined by TLC. After cooling, the mixture was filtered through diatomaceous earth and filter cake washed with ethyl acetate (100 mL) and tetrahydrofuran (100 mL). The filtrate was dried by anhydrous sodium sulfate, filtered and concentrated under reduced pressure. The residue was purified by using silica gel column chromatography (eluting with petroleum ether/ethyl acetate=2/1~1/1) to give tert-butyl 4-(4-amidopyrimidinyl-2-yl) pyrazole-1-carboxylate (4.50 g, 59.49% yield) as a pale yellow oil. $^1$H NMR (400 MHz, DMSO-d$_6$) δ=8.50 (s, 1H), 8.17 (s, 1H), 8.07 (d, J=5.8 Hz, 1H), 6.92 (br. s., 2H), 6.30 (d, J=5.8 Hz, 1H), 1.58 (s, 9H). MS (ESI). Calcd. for C$_{12}$H$_{15}$N$_5$O$_2$ [M+H]$^+$ 262, Found 262.

Step 2: Preparation of tert-butyl 4-(4-(3-(ethoxycarbonyl)thiourea)pyrimidin-2-yl)-1H-pyrazole-1-carboxylate (3)

To tert-butyl 4-(4-aminopyrimidinyl-2-yl) pyrazole-1-carboxylate (4.0 g, 15.3 mmol) dissolved in a solution of tetrahydrofuran (40 mL) and dichloromethane (40 mL) was added ethoxycarbonyl isothiocyanate (4.0 g, 30.6 mmol). The reaction mixture was heated to 70° C. and stirred for 16 hours. After TLC showed that the reaction was completed, the mixture was concentrated under reduced pressure, and purified through silica gel column chromatography (eluting with petroleum ether/ethyl acetate=10:1~2:1) to give tert-butyl 4-(4-(3-(ethoxycarbonyl)thiourea) pyrimidinyl-2-yl)-1H-pyrazole-1-carboxylate (4.00 g, 63.25% yield) as a pale yellow oil. $^1$H NMR (400 MHz, DMSO-d$_6$) δ=12.49 (br. s., 1H), 12.16 (br. s., 1H), 8.78 (d, J=5.8 Hz, 1H), 8.72 (s, 1H), 8.32 (s, 1H), 8.22 (br. s., 1H), 4.27 (q, J=7.1 Hz, 2H), 1.62 (s, 9H), 1.30 (t, J=7.2 Hz, 3H). MS (ESI) Calcd. for C$_{16}$H$_{20}$N$_6$O$_4$S [M+H]$^+$ 393, Found 393.

Step 3: Preparation of 5-(1H-pyrazole-4-yl)-[1,2,4]triazolo[1,5-c] pyrimidin-2-amine (Intermediate 1)

To hydroxylamine hydrochloride (3.5 g, 50.9 mmol) dissolved in a solution of methanol (50 mL) and ethanol (50 mL) was added DIEA (4.0 g, 30.6 mmol). After stirring the resulting turbid solution at 26° C. for 1 hour, tert-butyl 4-(4-(3-(ethoxycarbonyl)thiourea) pyrimidin-2-yl)-1H-pyrazole-1-carboxylate was added. Then the reaction mixture was heated to 90° C. for refluxing 3 hours, and TLC showed that the reaction was completed. The reaction mixture was concentrated under reduced pressure, and water (20 mL) was added. The resulting precipitation was filtered, collected, and dried under vacuum to give 5-(1H-pyrazole-4-yl)-[1,2,4]triazolo[1,5-c] pyrimidin-2-amine (1.7 g, 82.9% yield) as a white solid. $^1$H NMR (400 MHz, DMSO-d$_6$) δ=13.53 (br. s., 1H), 8.87 (br. s., 1H), 8.47 (br. s., 1H), 8.10 (d, J=6.0 Hz, 1H), 7.23 (d, J=6.0 Hz, 1H), 6.50 (s, 2H). MS (ESI) Calcd. for $C_8H_7N_7$[M+H]$^+$ 202, Found 202.

Step 4: Preparation of tert-butyl 3-[4-(2-amino-[1,2,4] triazolo[1,5-c] pyrimidin-5-yl) pyrazole-1-yl]-3-(cyanomethyl)azetidine-1-carboxylate (Intermediate 2)

To the Intermediate 1 (500 mg, 2.5 mmol) slightly dissolved in a suspension of acetonitrile (10 mL) was added tert-butyl 3-(cyanomethylene)azetidine-1-carboxylate (600 mg, 3.1 mmol) and DBU (756 mg, 4.97 mmol). The reaction mixture was stirred at 26° C. for 16 hours. After TLC showed that the reaction was completed, the mixture was concentrated under reduced pressure, and purified through silica gel column chromatography (eluting with petroleum ether/ethyl acetate=1:1~1:3) to give tert-butyl 3-[4-(2-amino-[1,2,4]triazolo[1,5-c]pyrimidin-5-yl)pyrazole-1yl]-3-(cyanomethyl) azetidine-1-carboxylate (800 mg, 81.3% yield) as a white solid. $^1$H NMR (400 MHz, CDCl$_3$) δ=9.03 (s, 1H), 8.64 (s, 1H), 8.17 (d, J=6.0 Hz, 1H), 7.24 (d, J=6.0 Hz, 1H), 4.83 (s, 2H), 4.57 (d, J=9.8 Hz, 2H), 4.33 (d, J=9.8 Hz, 2H), 3.36 (s, 2H), 1.49 (s, 9H). MS (ESI) Calcd. for $C_{18}H_{21}N_9O_2$ [M+H]$^+$ 396, Found 396.

Step 5: Preparation of 2-[3-[4-(2-amino-[1,2,4]triazolo[1,5-c]pyrimidin-5-yl) pyrazole-1-yl]cyclobutylamine-3-yl] acetonitrile (Intermediate 3)

To the Intermediate 2 (500 mL, 1.3 mmol) in DCM (10 mL) was added TFA (4 mL) at 15° C., and at this temperature, the mixture was stirred and reacted for 3 hours. After the reaction was completed, the reaction mixture was concentrated under reduced pressure to give 2-[3-[4-(2-amino-[1,2,4]triazolo[1,5-c]pyrimidin-5-yl) pyrazole-1-yl]cyclobutylamine-3-yl]acetonitrile (515 mg, 99.9% yield, TFA salt) as a brown solid. MS (ESI) Calcd. for $C_{13}H_{13}N_9$ [M+H]$^+$ 296, Found 296.

Step 6: Preparation of tert-butyl 3-(cyanomethyl)-3-[4-2-(cyclopropylcarbonylamino)-[1,2,4]triazolo[1,5-c]pyrimidin-5-yl]pyrazole-1-yl] azetidine-1-carboxylate (Intermediate 4)

To tert-butyl 3-[4-(2-amino-[1,2,4]triazolo[1,5-c]pyrimidin-5-yl)pyrazole-1-yl]-3-(cyanomethyl) azetidine-1-carboxylate (400 mg, 1.0 mmol) slightly dissolved in turbid solution of acetonitrile (8 mL) was added cyclopropanecarboxylic acid chloride (317 mg, 3.0 mmol) and triethylamine (307 mg, 3.0 mmol). The reaction mixture was stirred at 26° C. for 16 hours. After TLC showed that the reaction was completed, a disubstituted product was formed from LC-MS display. The reaction mixture was concentrated under reduced pressure, then methylamine in ethanol solution (27%~32%, 3 mL) was added, stirred at 26° C. for 0.5 hour.

A monosubstituted target product was formed from LC-MS display. The reaction mixture was concentrated under reduced pressure, and purified through silica gel column chromatography (eluting with petroleum ether/ethyl acetate=1:1~1:3) to give tert-butyl 3-(cyanomethyl)-3-[4-2-(cyclopropylcarbonylamino)-[1,2,4]triazolo[1,5-c]pyrimidin-5-yl]pyrazole-1-yl]azetidine-1-carboxylate (420 mg, 89.7% yield) as a white solid. $^1$H NMR (400 MHz, CDCl$_3$) δ=9.31 (s, 1H), 9.11 (s, 1H), 8.67 (s, 1H), 8.28 (d, J=6.0 Hz, 1H), 7.42 (d, J=6.0 Hz, 1H), 4.58 (d, J=9.5 Hz, 2H), 4.34 (d, J=9.5 Hz, 2H), 3.37 (s, 2H), 1.50 (s, 9H), 1.31-1.22 (m, 3H), 1.03 (qd, J=3.7, 7.4 Hz, 2H). MS (ESI) Calcd. for $C_{22}H_{25}N_9O_3$ [M+H]$^+$464, Found 464.

Step 7: Preparation of N-[5-[1-[3-(cyanomethyl) azetidine-3-yl]pyrazole-4-yl]-[1,2,4]triazolo[1,5-c] pyrimidin-2-yl]cyclopropanecarboxamide (Intermediate 5)

To 3-(cyanomethyl)-3-[4-2-(cyclopropylcarbonylamino)-[1,2,4]triazolo[1,5-c] pyrimidin-5-yl]pyrazole-1-yl]azetidine-1-carboxylate (220 mg, 474.7 umol) dissolved in dichloromethane (8 mL) was added trifluoroacetic acid (2 mL). The reaction mixture was stirred at 26° C. for 2 hours. After TLC showed that the reaction was completed, the mixture was concentrated under reduced pressure to give N-[5-[1-[3-(cyanomethyl)azetidine-3-yl]pyrazole-4-yl]-[1,2,4]triazolo[1,5-c]pyrimidin-2-yl]cyclopropanecarboxamide (280 mg, the crude product is directly used in the next step) as a pale yellow solid. MS (ESI) Calcd. for $C_{17}H_{17}N_9O$ [M+H]$^+$ 364, Found 364.

Preparation of the Intermediates 6-8

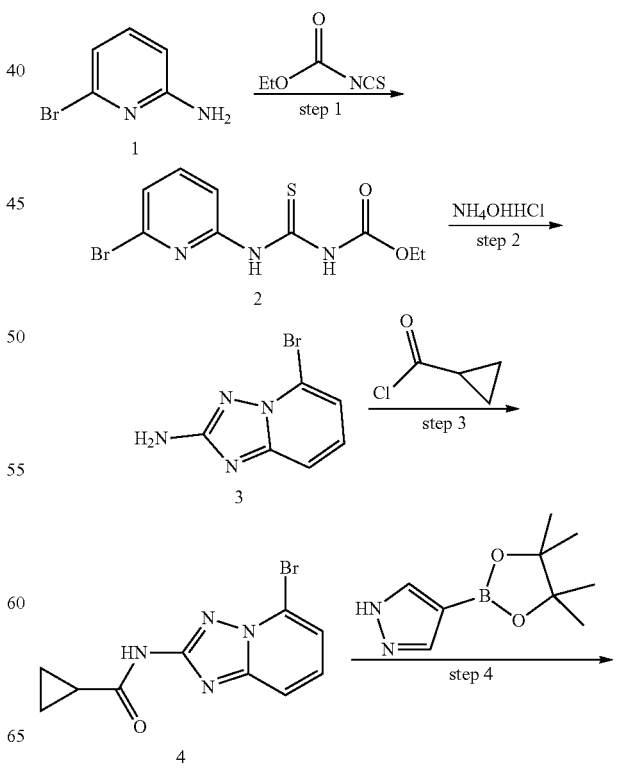

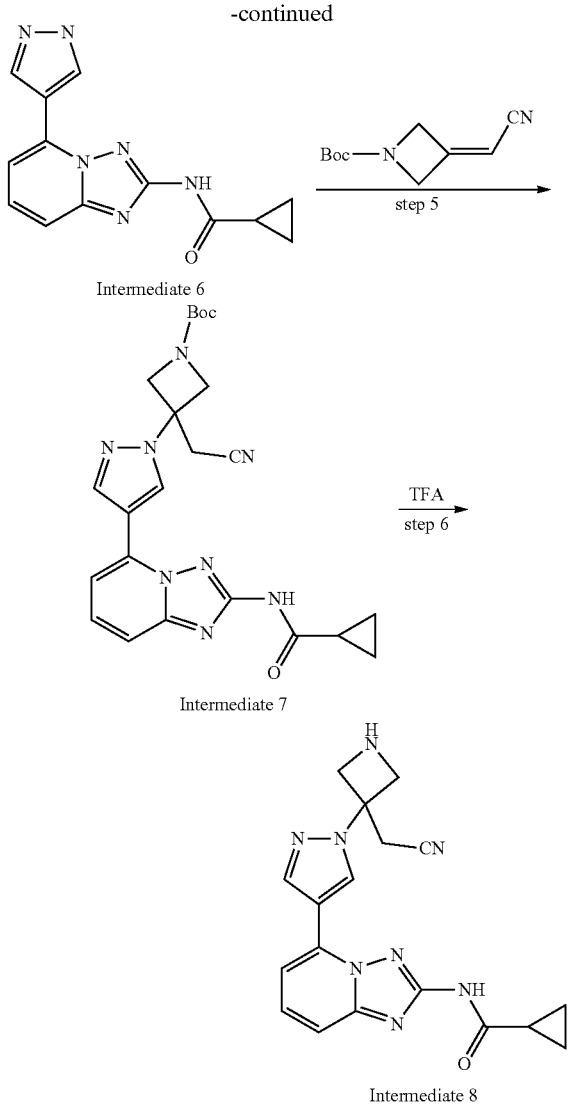

Intermediate 6

Intermediate 7

Intermediate 8

Step 1: Preparation of ethyl-N-[(6-bromo-2-pyridyl)thiocarbamoyl]carbamic acid (2)

To 6-bromopyridine-2-amine (30 mg, 173.4 mmol) dissolved in dichloromethane (400 mL) was added dropwise ethyl isothiocyanate (25.0 g, 190.7 mmol), and the reaction was carried out at 25° C. for 16 hours. After TLC showed that the reaction was completed, the reaction mixture was distilled under reduced pressure. The resulting residue was stirred by using 200 mL of petroleum ether for 30 min, then filtered. The filter cake was collected and dried to give ethyl-N-[(6-bromo-2-pyridyl)thiocarbamoyl]carbamic acid (51 g, 96.7% yield) as a faint red solid. $^1$H NMR (400 MHz, DMSO-d6) δ=12.17 (s, 1H), 11.66 (br. s., 1H), 8.65 (d, J=7.54 Hz, 1H), 7.82 (t, J=7.92 Hz, 1H), 7.49 (d, J=7.78 Hz, 1H), 4.22 (q, J=7.18 Hz, 2H), 1.25 (t, J=7.16 Hz, 3H). MS (ESI) Calcd. for $C_9H_{10}BrN_3O_2S$ [M+H]$^+$ 304, Found 304.

Step 2: Preparation of 5-bromo-[1,2,4]triazolo[1,5-a]pyridin-2-amine (3)

Hydroxylamine hydrochloride (35.2 g, 503.1 mmol), diisopropylethylamine (54.1 g, 419.3 mmol) was dissolved in a mixed solvent of ethanol (500 mL) and methanol (500 mL). After stirring at 25° C. for 1 hour, ethyl-N-[(6-bromo-2-pyridyl)thiocarbamoyl] carbamic acid (51.0 g, 167.7 mmol) was added, and purged with nitrogen for three times. The reaction mixture was heated to 80° C. for the reaction for 3 hours, and then cooled. After the reaction was completed from the TLC monitoring display, the reaction mixture was distilled under reduced pressure. The resulting residue was stirred by using 500 mL of water for 10 min, then filtered. The filter cake was collected and dried to give 5-bromo-[1,2,4]triazolo[1,5-a]pyridin-2-amine (32 g, 85.1% yield) as a white solid. $^1$H NMR (400 MHz, DMSO-d$_6$) 7.30-7.39 (m, 1H), 7.20 (dd, J=6.78, 1.76 Hz, 1H), 6.27 (s, 2H). MS (ESI) Calcd. for $C_6H_5BrN_4$ [M+H]$^+$ 215, Found 215.

Step 3: Preparation of N-(5-bromo-[1,2,4]triazolo[1,5-a]pyridin-2-yl)cyclopropyl carboxamide (4)

To 5-bromo-[1,2,4]triazolo[1,5-a]pyridin-2-amine (15.00 g, 70.41 mmol) and triethylamine (21.4 g, 211.2 mmol), dissolved in acetonitrile (150 mL) was added dropwise cyclopropanecarboxylic acid chloride (8.8 g, 84.5 mmol) at 0° C. After adding, the mixture was warmed to room temperature for the reaction for 16 hours. After TLC showed that the reaction was completed through monitoring, the reaction mixture was distilled under reduced pressure. The resulting residue was dissolved in an alcoholic solution of methylamine (150 mL), heated to 80° C. for the reaction for 1 hour, cooled, distilled under reduced pressure. The resulting residue was dissolved in mixed solution of water (100 mL) and ethyl acetate (200 mL), and the layers were separated and extracted. The combined organic phase was dried with anhydrous sodium sulfate and filtered, and the filtrate was distilled under reduced pressure. The resulting crude product was purified through silica gel column chromatography (eluting with ethyl acetate/petroleum ether=0~70%) to give N-(5-bromo-[1,2,4]triazolo[1,5-a]pyridin-2-yl)cyclopropyl carboxamide (7.2 g, 56.64% yield) as a pale yellow solid. $^1$H NMR (400 MHz, DMSO-d6) δ=11.20 (br. s., 1H), 7.68-7.73 (m, 1H), 7.52-7.58 (m, 1H), 7.46-7.51 (m, 1H), 1.96-2.09 (m, 1H), 0.82 (d, J=6.28 Hz, 4H). MS (ESI) Calcd. for $C_{10}H_9BrN_4O$ [M+H]$^+$ 282, Found 282.

Step 4: Preparation of N-[5-(1H-pyrazole-4-yl)-[1,2,4]triazolo[1,5-a]pyridin-2-yl]cyclopropane carboxamide (Intermediate 6)

To N-(5-bromo-[1,2,4]triazolo[1,5-a]pyridin-2-yl)cyclopropane carboxamide (3.0 mg, 10.67 mmol), 4-(4,4,5,5-tetramethyl-1,3,2-dioxaborolan-2-yl)-1H-pyrazole (2.4 g, 12.9 mmol) and potassium carbonate (3.7 g, 26.7 mmol), dissolved in a mixed solution of dioxane (30 mL) and water (5 mL), was added Pd(dppf)Cl$_2$ (260 mg) in the nitrogen atmosphere. The resulting mixture was heated to 110° C. for the reaction for 3 hours, then cooled to room temperature. After TLC showed that raw material was completely reacted, the reaction mixture was filtered. The filtrate was washed with water (150 mL) and extracted with ethyl acetate (150 mL×3). The combined organic phase was dried with anhydrous sodium sulfate and filtered, and the filtrate was distilled under reduced pressure. The resulting crude product was purified through silica gel column chromatography (eluting with ethyl acetate/petroleum ether=50~100%) to give N-[5-(1H-pyrazole-4-yl)-[1,2,4]triazolo[1,5-a]pyridin-2-yl]cyclopropane carboxamide (2.1 g, 62.4% yield) as a gray solid. $^1$H NMR (400 MHz, DMSO-$d_6$) δ=13.37 (br. s., 1H), 11.15 (br. s., 1H), 8.96 (s, 1H), 8.53 (s, 1H), 7.57-7.72 (m, 2H), 7.51 (d, J=8.28 Hz, 1H), 2.06 (br. s., 1H), 0.78-0.91 (m, 4H). MS (ESI) Calcd. for $C_{13}H_{12}N_6O$ [M+H]$^+$ 269, Found 269.

Step 5: Preparation of tert-butyl 3-(cyanomethyl)-3-[4-[2-(cyclopropylcarbonylamino)-[1,2,4]triazolo[1,5-a]pyridin-5-yl]pyrazole-1-yl]azetidine-1-carboxylate (Intermediate 7)

To N-[5-(1H-pyrazole-4-yl)-[1,2,4]triazolo[1,5-a]pyridin-2-yl] cyclopropane carboxamide (200 mg, 745.5 umol), tert-butyl 3-(cyanomethylene)azetidine-1-carboxylate (144.8 mg, 745.5 umol), dissolved in acetonitrile (5 mL), was added DBU (340.49 mg, 2.3 mmol) and reacted at room temperature for 16 hours. After LCMS showed that raw material was completely reacted, the reaction mixture was distilled under reduced pressure. The resulting residue was dissolved in mixed solution of water (20 mL) and ethyl acetate (20 mL), and the layers were separated and extracted. The combined organic phase was dried with anhydrous sodium sulfate and filtered, and the filtrate was distilled under reduced pressure. The resulting crude product was purified through preparative TLC (pure ethyl acetate) to give tert-butyl 3-(cyanomethyl)-3-[4-[2-(cyclopropylcarbonylamino)-[1,2,4]triazolo[1,5-a]pyridin-5-yl]pyrazole-1-yl] azetidine-1-carboxylate (170 mg, 44.4% yield) as a pale yellow solid. MS (ESI) Calcd. for $C_{23}H_{26}N_8O_3$ [M+H]$^+$ 463, Found 463.

Step 6: Preparation of N-[5-[1-[3-(cyanomethyl) azetidine-3-yl]pyrazole-4-yl]-[1,2,4]triazolo[1,5-a] pyridin-2-yl] cyclopropane carboxamide (Intermediate 8)(WX00)

To tert-butyl 3-(cyanomethyl)-3-[4-2-(cyclopropylcarbonylamino)-[1,2,4]triazolo[1,5-a]pyridin-5-yl]pyrazole-1-yl] azetidine-1-carboxylate (150 mg, 324.3 umol) dissolved in 5 mL of dichloromethane (5 mL) was added trifluoroacetic acid (1 mL) at room temperature for the reaction for 2 hours. After LCMS showed that the reaction was completely reacted, the reaction mixture was distilled under reduced pressure to give crude product of N-[5-[1-[3-(cyanomethyl) azetidine-3-yl] pyrazole-4-yl]-[1,2,4] triazolo[1,5-a]pyridin-2-yl]cyclopropane carboxamide (100 mg) as a yellow oil which was directly used in the next step. $^1$H NMR (400 MHz, DMSO-$d_6$) δ=11.16 (br. s., 1H), 9.18 (s, 1H), 8.71 (s, 1H), 7.75-7.63 (m, 2H), 7.61-7.50 (m, 1H), 4.00 (d, J=9.0 Hz, 2H), 3.71 (d, J=9.0 Hz, 2H), 3.57 (s, 2H), 2.13 (br. s., 1H), 0.95-0.81 (m, 4H). MS (ESI) Calcd. for $C_{18}H_{18}N_8O$ [M+H]$^+$ 363, Found 363.

Preparation of the Intermediates 9

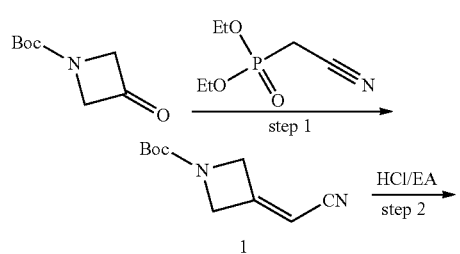

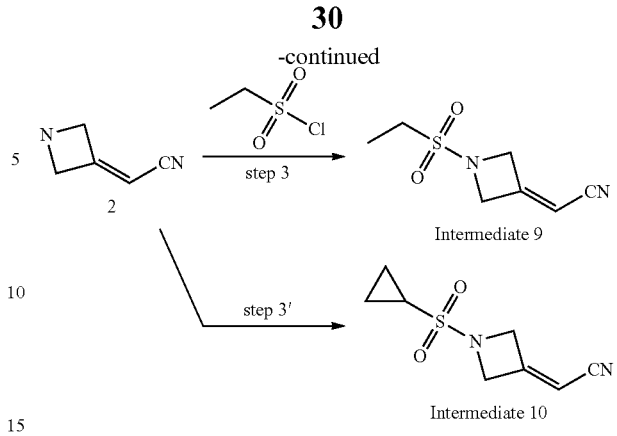

Step 1: Preparation of tert-butyl 3-(cyanomethyl)azetine-1-carbonate (1)

Under cooling in ice bath, to sodium-hydrogen (1.2 g, 30.7 mmol) in tetrahydrofuran (50 mL) was added dropwise cyanomethyl diethyl phosphite (5.7 g, 32.1 mmol) in tetrahydrofuran (50 mL). After adding dropwise, the mixture was stirred at 25° C. for 1 hour, then cooled to 0° C. Then tert-butyl 3-azetidinone-1-carbonate (5.0 g, 29.2 mmol) in tetrahydrofuran (50 mL) was added dropwise within 1 hour. The mixture is stirred at 25° C. for the reaction for 16 hours. After the reaction was completed, the reaction mixture was quenched with water (80 mL) and extracted with ethyl acetate (80 mL×3). The combined organic phase was washed with saturated salt water and dried with anhydrous sodium sulfate to give crude product of tert-butyl 3-(cyanomethyl) azetine-1-carbonate (5.2 g, 78.0% yield) as a yellow solid, the crude product was directly used in the next step without further purification. $^1$H NMR (400 MHz, CDCl$_3$) δ=5.38 (t, J=2.5 Hz, 1H), 4.73-4.68 (m, 2H), 4.61 (td, J=2.4, 4.3 Hz, 2H), 1.45 (s, 9H). MS (ESI) Calcd. for $C_{10}H_{14}N_2O_2$ [M+H]$^+$ 195, Found 195.

Step 2: Preparation of 2-(azetine-3-yl)methyl cyanide(2)

Tert-butyl 3-(cyanomethyl) azetine-1-carbonate (5.2 g, 26.8 mmol) was soaked with a small amount of ethyl acetate (5 mL). After stirring well, hydrochloride ethyl acetate (150 mL) was added at 0° C. and stirred at 0° C. for 1 hour. After TLC showed that the reaction was completed (petroleum ether/ethyl acetate=5:1), the resulting yellow suspension was filtered. The resulting solid was washed with a small amount of cold ethyl acetate (5 mL×2) and dried under vacuum to give 2-(azetine-3-yl) methyl cyanide (2.8 g, 80.0% yield) as a white solid. $^1$H NMR (400 MHz, D$_2$O) δ=5.69-5.65 (m, 1H), 4.95 (d, J=2.5 Hz, 2H), 4.88 (br. s., 2H). MS (ESI) Calcd. for $C_5H_6N_2$ [M+H]$^+$ 95, Found 95.

Step 3: Preparation of 2-(1-(ethyl sulfonyl)azetine-3-yl)methyl cyanide (Intermediate 9)

To a solution of 2-(azetine-3-yl) methyl cyanide (2.8 g, 21.4 mmol) and DIPEA (8.3 g, 64.3 mmol) in dichloromethane (30 mL) was added dropwise ethanesulfonyl chloride (4.1 g, 32.1 mmol) at 0° C. under the protection of nitrogen, and the temperature was kept below 2° C. when dropping. The reaction mixture was stirred at 25° C. for reacting for 16 hours. TLC showed that the reaction was completed (petroleum ether/ethyl acetate=1:1). After the reaction mixture was quenched with water, extracted with dichloromethane (30 mL×2). The combined organic phase was washed with saturated salt water (20 mL×2), dried with anhydrous sodium sulfate, filtered, and spun dry. The residue was purified through column chromatography (dichloromethane/ ethyl acetate=3/1) to give 2-(1-(ethylsulfonyl)azetine-3-yl) methyl cyanide (1.4 g, 33.0% yield) as a pale yellow solid. $^1$H NMR (400 MHz, CDCl$_3$) δ=5.50-5.41 (m, 1H), 4.79 (d, J=3.0 Hz, 2H), 4.71 (d, J=2.5 Hz, 2H), 3.06 (q, J=7.4 Hz, 2H), 1.40 (t, J=7.4 Hz, 3H). MS (ESI) Calcd. for C$_7$H$_{10}$N$_2$O$_2$S [M+H]$^+$187, Found 187.

Step 3': Preparation of 2-(1-cyclopropylsulfonylaze-tidine-3-alkenyl)acetonitrile (Intermediate 10)

Intermediate 10 was prepared in the same method as Intermediate 9. 2-(1-cyclopropylsulfonylazetidine-3-alkenyl)acetonitrile (1.5 g) was a pale yellow solid, MS (ESI) Calcd. for C$_7$H$_{10}$N$_2$O$_2$S [M+H]$^+$ 199, Found 199.

Example 1

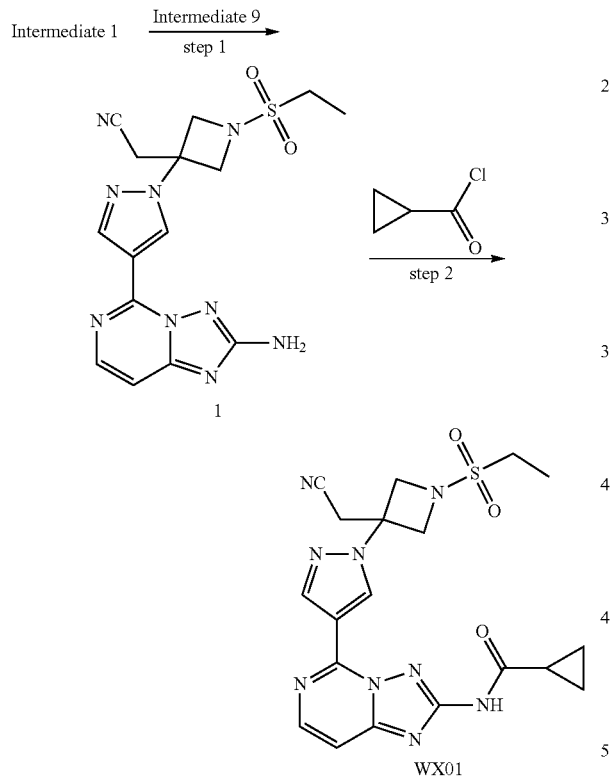

Step 1: Preparation of 2-[3-[4-(2-amino-[1,2,4]tri-azolo[1,5-c]pyrimidin-5-yl)pyrazole-1-yl]-1-ethyl-sulfonylazetidine-3-yl] acetonitrile (1)

To a suspension of Intermediate 1 (150 mg, 745.6 umol) slightly dissolved in acetonitrile (4 mL) and DMF (2 mL) was added Intermediate 9 (208 mg, 1.1 mmol) and DBU (227 mg, 1.5 mmol). The reaction mixture was stirred at 26° C. for 16 hours. LC-MS showed that the reaction was completed. The precipitated solid was filtered, collected, washed with cold acetonitrile (5 mL), and dried under reduced pressure to give 2-[3-[4-(2-amino-[1,2,4]triazolo[1,5-c]pyrimidin-5-yl) pyrazole-yl]-1-ethylsulfonylazetidine-3-yl] acetonitrile (200 mg, 69.2% yield) as a white solid. $^1$H NMR (400 MHz, DMSO-d$_6$) δ=9.16 (s, 1H), 8.69 (s, 1H), 8.16 (d, J=6.3 Hz, 1H), 7.31 (d, J=6.0 Hz, 1H), 6.56 (s, 2H), 4.53 (d, J=9.0 Hz, 2H), 4.28 (d, J=9.0 Hz, 2H), 3.70 (s, 2H), 3.25 (q, J=7.4 Hz, 2H), 1.25 (t, J=7.4 Hz, 3H). MS (ESI) Calcd. for C$_{15}$H$_{17}$N$_9$O$_2$S [M+H]$^+$ 388, Found 388.

Step 2: Preparation of N-[5-[1-[3-(cyanomethyl)-1-ethylsulfonylazetidine-3-yl]pyrazole-4-yl]-[1,2,4] triazolo[1,5-c]pyrimidin-2-yl]cyclopropanecarbox-amide(WX01)

To a suspension of 2-[3-[4-(2-amino-[1,2,4]triazolo[1,5-c]pyrimidin-5-yl)pyrazole-yl]-1-ethylsulfonyl azetidine-3-yl] acetonitrile (100 mg, 258.1 umol) slightly dissolved in acetonitrile (2 mL) and tetrahydrofuran (1 mL) was added cyclopropanecarboxylic acid chloride (80.9 mg, 774.4 umol) and triethylamine (78 mg, 774.4 mmol). The reaction mixture was stirred at 26° C. for 16 hours. TLC showed that the reaction was completed, and LC-MS showed that all was produced as a di-substituted product. After the reaction mixture was concentrated under reduced pressure, methylamine in ethanol solution (27%-32%, 3 mL) was added and stirred at 26° C. for reacting for 0.5 hour. LC-MS showed that all was produced as a mono-substituted product. The reaction mixture was concentrated under reduced pressure and purified through preparative HPLC (alkaline condition) to give N-[5-[1-[3-(cyanomethyl)-1-ethylsulfonylazetidine-3-yl]pyrazole-4-yl]-[1,2,4]triazolo[1,5-c]pyrimidin-2-yl]cyclopropanecarboxamide (25 mg, 21.1% yield). $^1$H NMR (400 MHz, DMSO-d$_6$) δ=11.43 (br. s., 1H), 9.25 (s, 1H), 8.82 (s, 1H), 8.32 (d, J=6.0 Hz, 1H), 7.60 (d, J=6.3 Hz, 1H), 4.50 (d, J=9.0 Hz, 2H), 4.28 (d, J=9.0 Hz, 2H), 3.70 (s, 2H), 3.24 (q, J=7.3 Hz, 2H), 2.18-2.02 (m, 1H), 1.23 (t, J=7.3 Hz, 3H), 0.95-0.80 (m, 4H). MS (ESI) Calcd. for C$_{19}$H$_{21}$N$_9$O$_3$S [M+H]$^+$ 456, Found 456.

Example 2

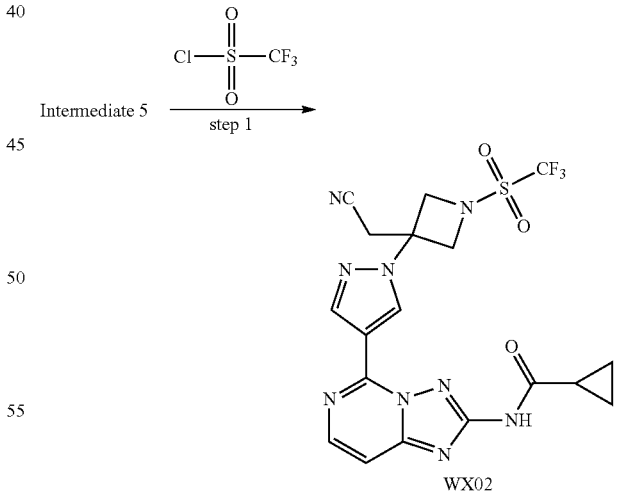

Step 1: Preparation of N-[5-[1-[3-(cyanomethyl)-1-(trifluoromethylsulfonyl)azetidine-3-yl]pyrazole-4-yl]-[1,2,4]triazolo[1,5-c]pyrimidin-2-yl]cyclopropanecarboxamide(WX02)

To a suspension of Intermediate 5 (100 mg, 209.5 umol) slightly dissolved in dichloromethane (3 mL) was added trifluoromethanesulfonyl chloride (53 mg, 314.2 umol) and triethylamine (106 mg, 1.1 mmol). The reaction mixture was stirred at 26° C. for 16 hours. LC-MS showed that the reaction was completed. The reaction mixture was concentrated under reduced pressure and purified through preparative HPLC (alkaline condition) to give N-[5-[1-[3-(cyanomethyl)-1-(trifluoromethylsulfonyl)azetidine-3-yl]pyrazole-4-yl]-[1,2,4]triazolo[1,5-c]pyrimidin-2-yl] cyclopropanecarboxamide (25 mg, 24.1% yield). $^1$H NMR (400 MHz, DMSO-d$_6$) δ=11.45 (br. s., 1H), 9.27 (s, 1H), 8.90 (s, 1H), 8.35 (d, J=6.0 Hz, 1H), 7.63 (d, J=6.3 Hz, 1H), 4.90 (d, J=9.0 Hz, 2H), 4.72 (d, J=9.0 Hz, 2H), 3.85 (s, 2H), 1.30-1.23 (m, 1H), 0.97-0.87 (m, 4H). MS (ESI) Calcd. for $C_{18}H_{16}F_3N_9O_3S$ [M+H]$^+$ 496, Found 496.

Example 3

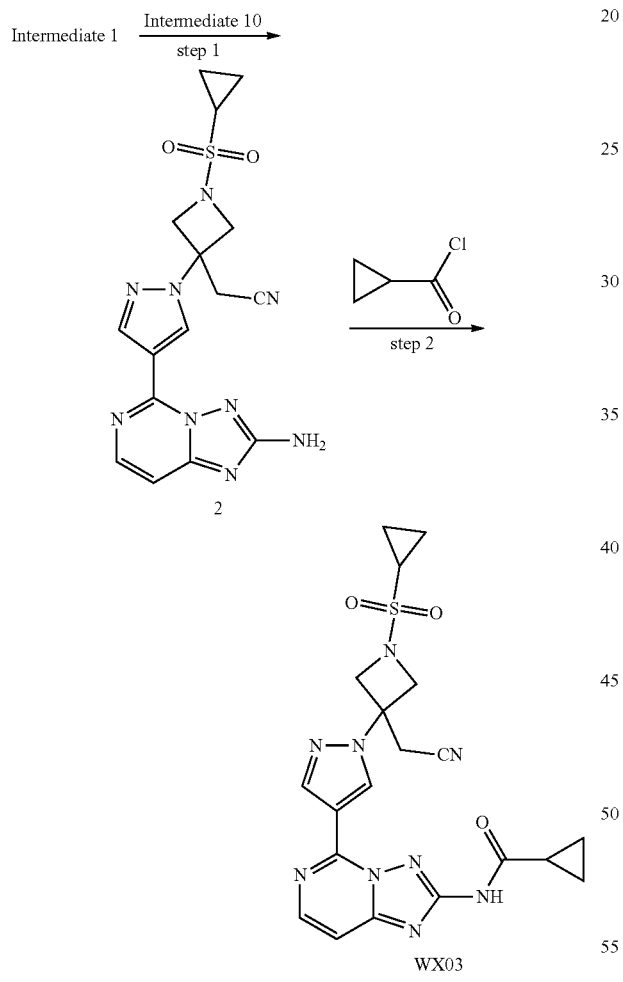

Step 1: Preparation of 2-[3-[4-(2-amino-[1,2,4]triazolo[1,5-c]pyrimidin-5-yl)pyrazole-1-yl]-1-cyclopropylsulfonyl-azetidine-3-yl] acetonitrile (2)

To a suspension of Intermediate 1 (150 mg, 745.6 umol) dissolved in acetonitrile (4 mL) was added Intermediate 10 (192 mg, 969.2 umol) and DBU (227 mg, 1.5 mmol). The reaction mixture was stirred at 26° C. for 16 hours. TLC showed that the reaction was completed. The precipitated solid was filtered, collected, washed with cold acetonitrile (5 mL), and dried under reduced pressure to give 2-[3-[4-(2-amino-[1,2,4]triazolo[1,5-c]pyrimidin-5-yl)pyrazole-1-yl]-1-cyclopropylsulfonyl-azetidine-3-yl] acetonitrile (200 mg, 67.2% yield) as a white solid. H NMR (400 MHz, DMSO-d$_6$) δ=9.18 (s, 1H), 8.70 (s, 1H), 8.15 (d, J=6.3 Hz, 1H), 7.30 (d, J=6.0 Hz, 1H), 6.56 (s, 2H), 4.59 (d, J=9.3 Hz, 2H), 4.33 (d, J=9.3 Hz, 2H), 3.70 (s, 2H), 2.90-2.82 (m, 1H), 1.09-1.03 (m, 2H), 1.03-0.96 (m, 2H). MS (ESI) Calcd. for $C_{16}H_{17}N_9O_2S$ [M+H]$^+$ 400, Found 400.

Step 2: Preparation of N-[5-[1-[3-(cyanomethyl)-1-cyclopropylsulfonyl-azetidine-3-yl]pyrazole-4-yl]-[1,2,4]triazolo[1,5-c]pyrimidin-2-yl]cyclopropanecarboxamide (WX3)

To a suspension of 2-[3-[4-(2-amino-[1,2,4]triazolo[1,5-c]pyrimidin-5-yl)pyrazole-1-yl]-1-cyclopropylsulfonyl-azetidine-3-yl]acetonitrile (80 mg, 200.3 umol) slightly dissolved in acetonitrile (2 mL) was added cyclopropanecarboxylic acid chloride (63 mg, 600.9 umol) and triethylamine (61 mg, 600.9 umol). The reaction mixture was stirred at 26° C. for 16 hours and at 80° C. for 3 hours. LC-MS showed that all was produced as a mixture of mono- and di-substituted product. After the reaction mixture was concentrated under reduced pressure, methylamine in ethanol solution (27%-32%, 3 mL) was added and stirred at 26° C. for 0.5 hour. LC-MS showed that all was produced as a mono-substituted product. The reaction mixture was concentrated under reduced pressure and purified through preparative HPLC (alkaline condition) to give N-[5-[1-[3-(cyanomethyl)-1-cyclopropylsulfonyl-azetidine-3-yl]pyrazole-4-yl]-[1,2,4]triazolo[1,5-c]pyrimidin-2-yl] cyclopropanecarboxamide (60 mg, 64.1% yield). $^1$H NMR (400 MHz, DMSO-d$_6$) δ=11.43 (s, 1H), 9.27 (s, 1H), 8.81 (s, 1H), 8.32 (d, J=6.0 Hz, 1H), 7.60 (d, J=6.0 Hz, 1H), 4.57 (d, J=9.3 Hz, 2H), 4.32 (d, J=9.3 Hz, 2H), 3.70 (s, 2H), 2.92-2.79 (m, 1H), 2.07 (d, J=13.6 Hz, 1H), 1.07-0.96 (m, 4H), 0.91-0.83 (m, 4H). MS (ESI) Calcd. for $C_{20}H_{21}N_9O_3S$ [M+H]$^+$ 468, Found 468.

Example 4

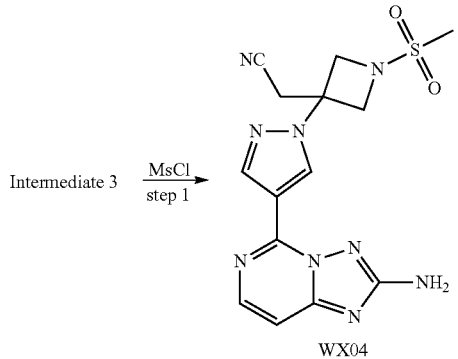

Step 1: Preparation of 2-[3-[4-(2-amino-[1,2,4]triazolo[1,5-c]pyrimidin-5-yl)pyrazole-1-yl]-1-methylsulfonyl-cyclobutylamine-3-yl] acetonitrile (WX04)

To Intermediate 3 (1.0 g, 2.4 mmol, TFA salt) and triethylamine (617 mg, 6.1 mmol), dissolved in solution of DCM (50 mL) was added dripwise MsCl (307 mg, 2.7 mmol) at 15° C. After dropping, the reaction mixture was stirred at 15° C. for 2 hours. After the reaction was completed, the reaction mixture was concentrated to dry. The resulting solid was separated and purified through preparative HPLC (alkaline condition) to give 2-[3-[4-(2-amino-[1,2,4]triazolo[1,5-c]pyrimidin-5-yl)pyrazole-1-yl]-1-methylsulfonyl-cyclobutylamine-3-yl]acetonitrile (800 mg, 87.8% yield). $^1$H-NMR (400 MHz, DMSO-d$_6$) δ=9.17 (s, 1H), 8.70 (s, 1H), 8.15 (d, J=6.0 Hz, 1H), 7.30 (d, J=6.0 Hz, 1H), 6.56 (brs, 2H), 4.55 (d, J=9.2 Hz, 2H), 4.31 (d, J=9.2 Hz, 2H), 3.69 (s, 2H), 3.14 (s, 3H). MS (ESI) Calcd. for $C_{14}H_{12}F_3N_9O_2S$ [M+H]$^+$ 428, Found 428.

Example 5

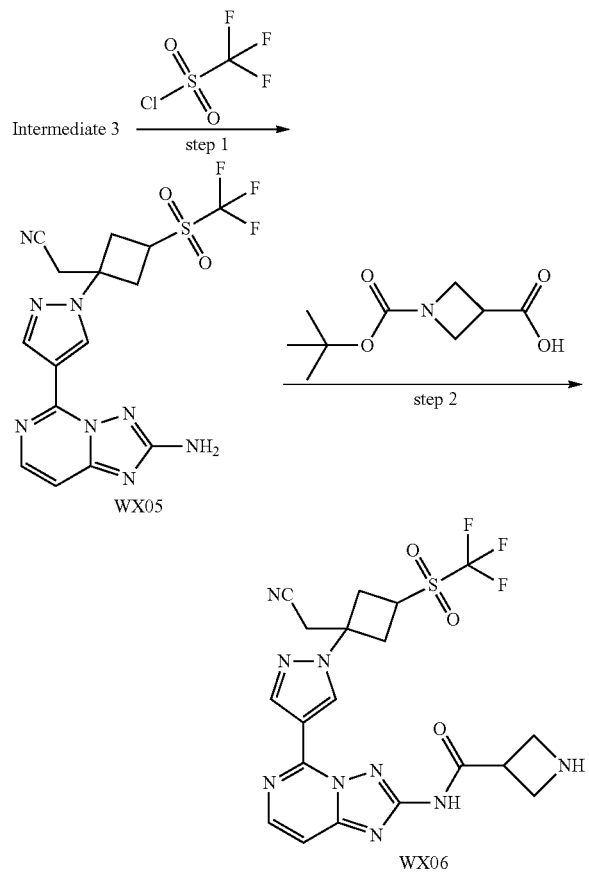

Step 1: Preparation of 2-[3-[4-(2-amino-[1,2,4]triazolo[1,5-c]pyrimidin-5-yl)pyrazole-1-yl]-1-(trifluoromethylsulfonyl)cyclobutylamine-3-yl]acetonitrile (WX05)

To a solution of Intermediate 3 (515 mg, 1.7 mmol) and TEA (264 mg, 2.6 mmol) dissolved in DCM (10 mL), was added dropwise trifluoromethanesulfonyl chloride (323 mg, 1.9 mmol) at 15° C. under the protection of nitrogen. After dropping, the reaction mixture was stirred at 15° C. for 3 hours. After the reaction was completed, the mixture was concentrated to dry. The resulting solid was beat with water, and filtered, the filter cake was dried to give 2-[3-[4-(2-amino-[1,2,4]triazolo[1,5-c]pyrimidin-5-yl)pyrazole-1-yl]-1-(trifluoromethylsulfonyl)cyclobutylamine-3-yl]acetonitrile (700 mg, 94.1% yield) as a white solid. $^1$H-NMR (400 MHz, DMSO-d$_6$) δ=9.18 (s, 1H), 8.74 (s, 1H), 8.15 (d, J=6.0 Hz, 1H), 7.30 (d, J=6.0 Hz, 1H), 6.55 (brs, 2H), 4.91 (d, J=9.2 Hz, 2H), 4.70 (d, J=9.2 Hz, 2H), 3.82 (s, 2H). MS (ESI) Calcd. for $C_{14}H_{12}F_3N_9O_2S$ [M+H]$^+$ 428, Found 428.

Step 2: Preparation of N-[5-[1-[3-(cyanomethyl)-1-(trifluoromethylsulfonyl) cyclobutylamine-3-yl]pyrazole-4-yl]-[1,2,4]triazolo[1,5-c]pyrimidin-2-yl]cyclobutylamine-3-formamide(WX06)

To DCM (10 mL) solution of N-tert-butyl-formylcyclobutylamine-3-carboxylic acid (198 mg, 982.8 umol) and DMF (100 uL) was added dropwise oxalyl chloride (156 mg, 1.23 mmol) in DCM (2 mL) at 0° C. under the protection of nitrogen. After dropping, the reaction mixture was stirred at 0° C. for 2 hours. Then the reaction mixture was concentrated under reduced pressure to dry. The resulting liquid was dissolved in DCM (2 mL), and was added dropwise through a injector to 2-[3-[4-(2-amino-[1,2,4]triazolo[1,5-c]pyrimidin-5-yl)pyrazole-1-yl]-1-(trifluoromethylsulfonyl)cyclobutylamine-3-yl]acetonitrile (350 mg, 818.9 umol) in DCM (10 mL) at 0° C. under the protection of nitrogen. After dropping, the reaction mixture was stirred at 0° C. for 2 hours. The reaction mixture was directly purified through preparative thin-layer chromatography (DCM/MeOH=10/1) to give Boc protected product (10 mg). The product was dissolved in DCM (2 mL), to which the TFA (2 mL) was added at 15° C. The resulting mixture was stirred at 15° C. for 1 hour. After the reaction was completed, the mixture was concentrated and dried. The resulting solid was separated and purified through preparative HPLC (alkaline method) to give N-[5-[1-[3-(cyanomethyl)-1-(trifluoromethylsulfonyl)cyclobutylamine-3-yl]pyrazole-4-yl]-[1,2,4]triazolo[1,5-c]pyrimidin-2-yl]cyclobutylamine-3-formamide (2 mg, 0.42% yield). MS (ESI) Calcd. for $C_{18}H_{17}F_3N_{10}O_3S$ [M+H]$^+$ 511, Found 511.

Example 6

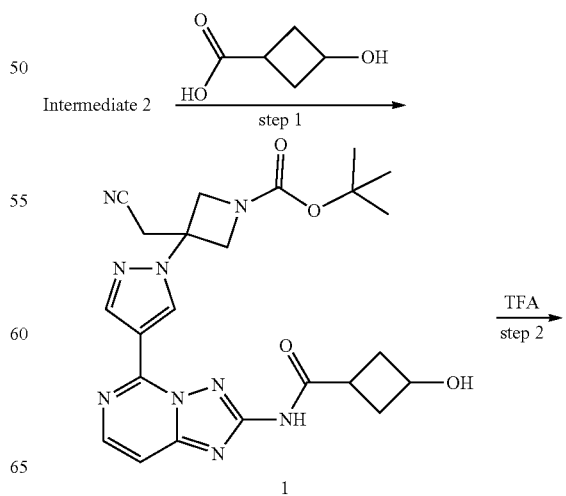

-continued

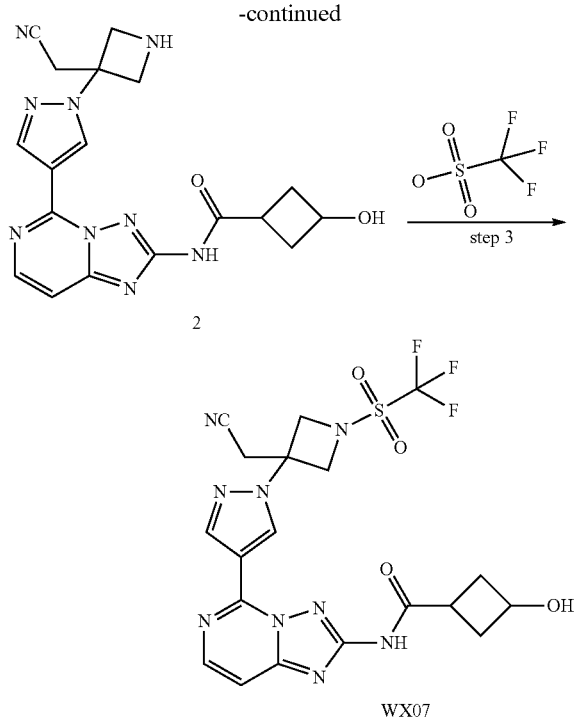

Step 1: Preparation of tert-butyl-3-(cyanomethyl)-3-[4-[2-[(3-hydroxycyclobutane formoxyl)amino]-[1,2,4] triazolo[1,5-c]pyrimidin-5-yl]pyrazole-1-yl] cyclobutane-1-formate (1)

To pyridine (10 mL) was added the mixture of Intermediate (300 mg, 758.7 umol), 3-hydroxycyclobutane formic acid (106 mg, 910.4 umol) and EDCI (218 mg, 1.1 mmol), and the resulting mixture was heated to reflux for 16 hours under the protection of nitrogen. After concentrating to dry, the remaining solid was purified through preparative thin-layer chromatography (DCM/MeOH=10/1) to give tert-butyl-3-(cyanomethyl)-3-[4-[2-[(3-hydroxycyclobutaneformoxyl)amino]-[1,2,4]triazolo[1,5-c]pyrimidin-5-yl] pyrazole-1-yl]cyclobutane-1-formate (36 mg, 9.61% yield) as a white solid. MS (ESI) Calcd. for $C_{23}H_{27}N_9O_4$ $[M+H]^+$ 494, Found 494.

Step 2: Preparation of N-[5-[1-[3-(cyanomethyl) cyclobutylamine-3-yl]pyrazole-4-yl]-[1,2,4]triazolo [1,5-c]pyrimidin-2-yl]-3-hydroxy-cyclobutane formamide (2)

To a solution of tert-butyl-3-(cyanomethyl)-3-[4-[2-[(3-hydroxycyclobutaneformoxyl) amino]-[1,2,4]triazolo[1,5-c] pyrimidin-5-yl]pyrazole-1-yl]cyclobutane-1-formate (36 mg, 72.9 umol) in dichloromethane (2.00 mL) was added dropwise TFA (1 mL) at 15° C. The resulting mixture was stirred at 15° C. for 30 min. LCMS showed that the reaction was completed. The reaction mixture was concentrated at 30° C. until dry to give N-[5-[1-[3-(cyanomethyl)cyclobutylamine-3-yl]pyrazole-4-yl]-[1,2,4]triazolo[1,5-c]pyrimidin-2-yl]-3-hydroxy-cyclobutane formamide (37 mg, 99.9% yield, TFA salt) as a yellow solid. MS (ESI) Calcd. for $C_{18}H_{19}N_9O_2$ $[M+H]^+$ 394, Found 394.

Step 3: Preparation of N-[5-[1-[3-(cyanomethyl)-1-(trifluoromethylsulfonyl)cyclobutylamine-3-yl]pyrazole-4-yl]-[1,2,4]triazolo[1,5-c]pyrimidin-2-yl]-3-hydroxy-cyclobutane formamide(WX07)

To a solution of N-[5-[1-[3-(cyanomethyl)cyclobutylamine-3-yl]pyrazole-4-yl]-[1,2,4]triazolo[1,5-c]pyrimidin-2-yl]-3-hydroxy-cyclobutane formamide (15 mg, 29.6 umol) and triethylamine (9 mg, 88.7 umol) in DCM (5.00 mL) was added dropwise a solution of trifluoromethanesulfonyl chloride (7 mg, 44.34 umol) in DCM (1 mL) at 20° C. under the protection of nitrogen. After adding, the mixture was stirred at 20° C. for 1 hour. After the reaction was completed, the reaction mixture was concentrated to dry. The resulting solid was separated and purified through preparative HPLC (0.1% of $NH_4OH$ was used as an additive) to give N-[5-[1-[3-(cyanomethyl)-1-(trifluoromethylsulfonyl)cyclobutylamine-3-yl]pyrazole-4-yl]-[1,2,4]triazolo[1,5-c]pyrimidin-2-yl]-3-hydroxy-cyclobutane formamide (8 mg, 51.50% yield). $^1$H-NMR (400 MHz, MeOD-$d_4$) δ=9.29 (s, 1H), 8.73 (s, 1H), 8.32 (d, J=6.4 Hz, 1H), 7.49 (d, J=6.0 Hz, 1H), 5.00 (d, J=9.6 Hz, 2H), 4.70 (d, J=9.2 Hz, 2H), 4.05-4.13 (m, 1H), 3.70 (s, 2H), 2.90 (brs, 1H), 2.50-2.66 (m, 2H), 2.20-2.35 (m, 2H). MS (ESI) Calcd. for $C_{19}H_8F_3N_9O_4S$ $[M+H]^+$ 526, Found 526.

Example 7

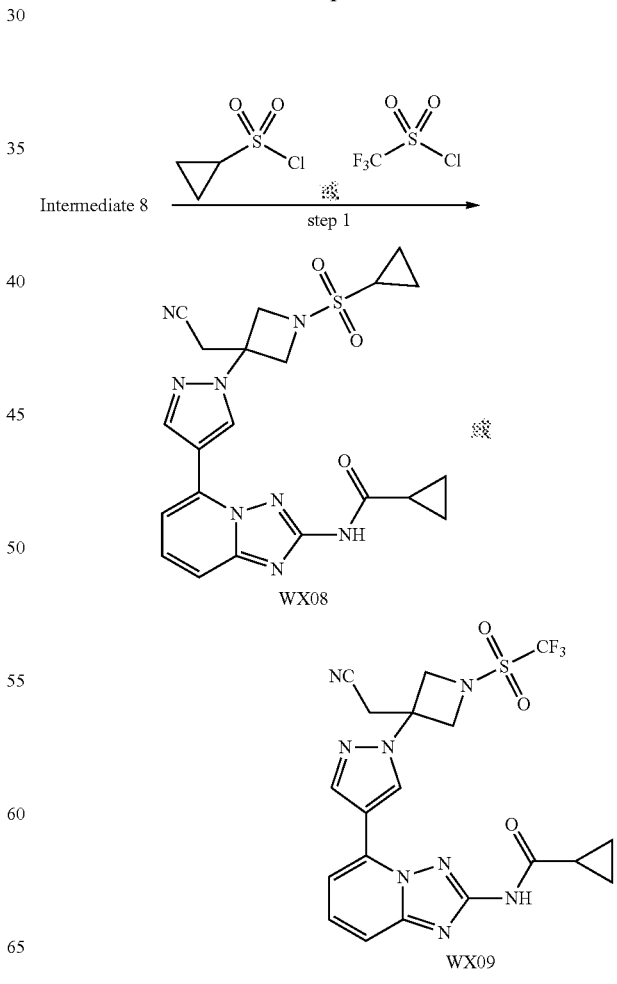

Step 1: Preparation of N-(5-(1-(3-(cyanomethyl)-1-(trifluoromethyl sulfonyl)azetidine-3-yl)-1H-pyrazole-4-yl)-[1,2,4]triazolo[1,5-a]pyridin-2-yl)cyclopropane formamide To Intermediate 8 (100 mg, 275.9 umol) and triethylamine (84 mg, 827.9 umol), dissolved in dichloromethane (5 mL) was dropwise added slowly trifluoromethanesulfonyl chloride (56 mg, 331.4 umol) at 0° C. After adding, the mixture was warmed to room temperature for reacting for 16 hours. After LCMS showed that the reaction was completed, the reaction mixture was diluted with water (20 mL), extracted with dichloromethane (20 mL×3). The combined organic phase was dried with anhydrous sodium sulfate and filtered, and the filtrate was distilled under reduced pressure. The resulting residue was purified through thin layer chromatography (ethyl acetate) to give N-(5-(1-(3-(cyanomethyl)-1-(trifluoromethylsulfonyl)azetidine-3-yl)-1H-pyrazole-4-yl)-[1,2,4]triazolo[1,5-a]pyridin-2-yl)cyclopropane formamide (WX09, 45 mg, 31.33% yield), $^1$H NMR (400 MHz, METHANOL-$d_4$) $\delta$=9.21 (s, 1H), 8.59 (s, 1H), 7.71-7.77 (m, 1H), 7.60 (dd, J=14.44, 8.16 Hz, 1H), 5.00 (d, J=9.04 Hz, 2H), 4.70 (d, J=9.04 Hz, 2H), 3.68 (s, 2H), 1.28-1.39 (m, 1H), 1.11 (quin, J=3.84 Hz, 2H) 0.97-1.04 (m, 2H). MS (ESI) Calcd. for $C_{19}H_{17}N_8O_3F_3S$ [M+H]$^+$ 495, Found 495.

Preparation of WX08: N-(5-(1-(3-(cyanomethyl)-1-(cyclopropylsulfonyl)azetidine-3-yl)-1H-pyrazole-4-yl)-[1,2,4]triazolo[1,5-a]pyridin-2-yl)cyclopropane formamide (WX08) was prepared using the preparation method similar to WX09 (Step 1). $^1$H NMR (400 MHz, METHANOL-$d_4$) $\delta$=9.23 (s, 1H), 8.58 (s, 1H), 7.71-7.76 (m, 1H), 7.58-7.65 (m, 2H), 4.70 (d, J=9.28 Hz, 2H), 4.39 (d, J=9.04 Hz, 2H), 3.64 (s, 2H), 2.72 (dt, J=12.74, 6.31 Hz, 1H), 1.78 (d, J=7.04 Hz, 1H), 1.08-1.14 (m, 6H), 1.00 (dd, J=7.28, 3.26 Hz, 2H). MS (ESI) Calcd. for $C_{21}H_{22}N_8O_3S$ [M+H]$^+$ 467, Found 467.

Example 8

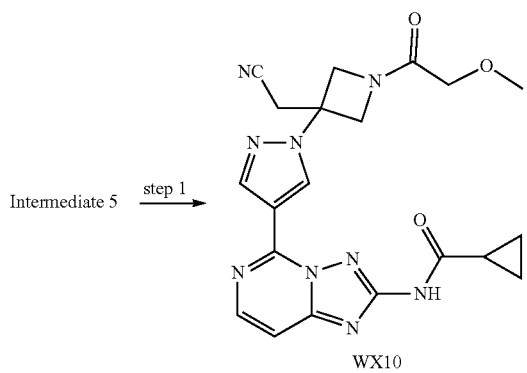

WX10

Step 1: Preparation of N-[5-[1-[3-(cyanomethyl)-1-(2-methoxyacetyl)azetidine-3-]pyrazole-4-]-[1,2,4]triazoloe[1,5-c]pyrimidine2-]cyclopropane carboxamide 2-Methoxyacetic acid (11 mg, 128.4 umol) was dissolved in mixture solvent of DCM/DMF (6 mL, 5:1). HOBt (35 mg, 256.9 umol) and EDCI (49 mg, 256.9 umol) was added to the mixture in order. The resulting mixture was stirred for reacting for 1 hour. Intermediate 5 (70 mg, 192.6 umol) and DIEA (50 mg, 385.3 umol) were added and stirred at 15° C. for reacting for 12 hours. LC-MS showed that the raw material was completely reacted to the target product. The reaction mixture was concentrated under reduced pressure to remove DCM and DMF and separated through preparative HPLC (alkalinity) to give N-[5-[1-[3-(cyanomethyl)-1-(2-methoxyacetyl)azetidine-3-]pyrazole-4-]-[1,2,4]triazoloe[1,5-c]pyrimidine2-]cyclopropane carboxamide (30 mg, 53.7% yield). $^1$H NMR (400 MHz, DMSO-$d_6$) $\delta$=9.26 (s, 1H), 8.80 (s, 1H), 8.34 (d, J=6.0 Hz, 1H), 7.61 (d, J=6.3 Hz, 1H), 4.81 (d, J=10.0 Hz, 1H), 4.61 (d, J=10.0 Hz, 1H), 4.46 (d, J=10.5 Hz, 1H), 4.33 (d, J=10.3 Hz, 1H), 4.01 (s, 2H), 3.72 (s, 2H), 3.32 (s, 3H), 2.12 (br. s., 1H), 0.98-0.84 (m, 4H). MS (ESI) Calcd. for $C_{20}H_{21}N_9O_3$ [M+H]$^+$ 436, Found 436.

Example 9

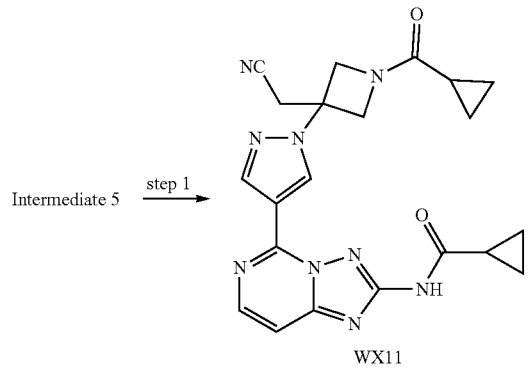

WX11

Step 1: Preparation of N-[5-[1-[3-(cyanomethyl)-1-(cyclopropylcarbonyl)azetidine-3-]pyrazole-4-]-[1,2,4]triazoloe[1,5-c]pyrimidine2-]cyclopropane carboxamide Intermediate 5 (79 mg, 216.3 umol) was dissolved in dichloromethane (3 mL), and DIEA (84 mg, 648.9 umol) was added. Then cyclopropionyl chloride (27 mg, 259.6 umol) was added though a syringe within 5 min, and the reaction mixture was stirred at 15° C. for reacting for 3 hours. LC-MS showed that the raw material was completely reacted to the target product. The reaction mixture was concentrated under reduced pressure to remove DCM and DMF and separated through preparative HPLC (alkalinity) to give N-[5-[1-[3-(cyanomethyl)-1-(cyclopropylcarbonyl)azetidine-3-]pyrazole-4-]-[1,2,4]triazoloe[1,5-c]pyrimidine2-]cyclopropane carboxamide (50 mg, 53.6% yield). $^1$H NMR (400 MHz, DMSO-$d_6$) $\delta$=9.25 (s, 1H), 8.83-8.78 (m, 1H), 8.32 (dd, J=3.8, 6.0 Hz, 1H), 7.60-7.52 (m, 1H), 4.88 (d, J=9.3 Hz, 1H), 4.68 (d, J=9.5 Hz, 1H), 4.44 (d, J=10.5 Hz, 1H), 4.29 (d, J=10.3 Hz, 1H), 3.72 (d, J=5.5 Hz, 2H), 3.13 (br. s., 1H), 1.69-1.55 (m, 1H), 0.98-0.85 (m, 4H), 0.77 (br. s., 4H). MS (ESI) Calcd. for $C_{21}H_{21}N_9O_2$ [M+H]$^+$ 432, Found 432.

Example 10

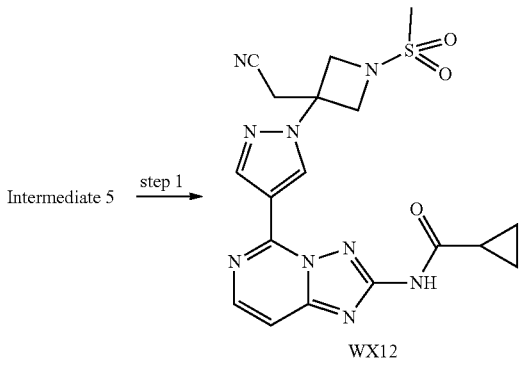

Step 1: Preparation of N-[5-[1-[3-(cyanomethyl)-1-methanesulfonyl-azetidine-3-]pyrazole-4-]-[1,2,4]triazoloe[1,5-c]pyrimidine2-] cyclopropane carboxamide(WX12)

Intermediate 5 (100 mg, 275.2 umol) was suspended in dichloromethane (8 mL). DIEA (107 mg, 825.6 umol) and MsCl (140 mg, 1.2 mmol) was added in order. The reaction mixture was stirred at 15° C. for reacting for 2 hours. LC-MS showed that the raw material was completely reacted, and the target product was detected. The reaction mixture was concentrated under reduced pressure to remove DCM and separated through preparative HPLC (alkalinity) to give N-[5-[1-[3-(cyanomethyl)-1-methanesulfonyl-azetidine-3-]pyrazole-4-]-[1,2,4]triazoloe[1,5-c]pyrimidine2-] cyclopropane carboxamide (39 mg, 31.1% yield). $^1$H NMR (400 MHz, DMSO-d$_6$) δ=9.28 (s, 1H), 8.86 (s, 1H), 8.35 (d, J=6.3 Hz, 1H), 7.63 (d, J=6.3 Hz, 1H), 6.08 (br. s., 1H), 4.55 (d, J=9.5 Hz, 2H), 4.33 (d, J=9.3 Hz, 2H), 3.72 (s, 2H), 3.16 (s, 3H), 2.10 (d, J=14.8 Hz, 1H), 1.01-0.79 (m, 4H). MS (ESI) Calcd. for C$_{18}$H$_{19}$N$_9$O$_3$S [M+H]$^+$ 442, Found 442.

Example 11

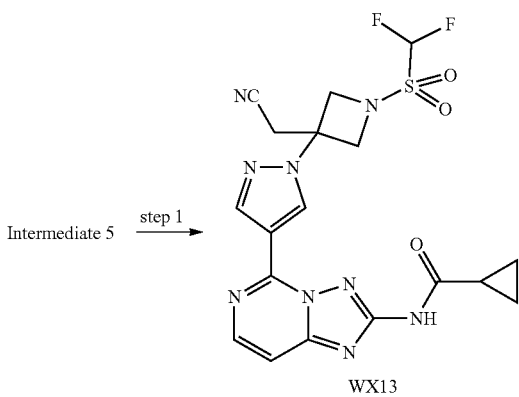

Step 1: Preparation of N-[5-[1-[3-(cyanomethyl)-1-(difluoromethylsulfonyl)-azetidine-3-]pyrazole-4-]-[1,2,4]triazoloe[1,5-c]pyrimidine2-]cyclopropane carboxamide (WX13)

Intermediate 5 (100 mg, 275.2 umol) was suspended in dichloromethane (8 mL). DIEA (178 mg, 1.4 mmol) and difluoromethylsulfonyl chloride (62 mg, 412.8 mmol) was added in order. The reaction mixture was stirred at 15° C. for reacting for 12 hours. LC-MS showed that the raw material was completely reacted, and the target product was detected. The reaction mixture was concentrated under reduced pressure to remove DCM. The residue was diluted with DMF and MeOH to a solution (5 mL), and separated through preparative HPLC (alkalinity) to give N-[5-[1-[3-(cyanomethyl)-1-(difluoromethylsulfonyl)-azetidine-3-]pyrazole-4-]-[1,2,4]triazolo[1,5-c]pyrimidin2-]cyclo propyl carboxamide (8 mg, 6.1% yield). $^1$H NMR (400 MHz, DMSO-d$_6$) δ=11.46 (br. s., 1H), 9.27 (s, 1H), 8.87 (s, 1H), 8.34 (d, J=6.3 Hz, 1H), 7.63 (d, J=6.0 Hz, 1H), 7.42-7.06 (m, 1H), 4.79 (d, J=9.0 Hz, 2H), 4.67-4.49 (m, 2H), 3.78 (s, 2H), 2.26-1.96 (m, 1H), 0.97-0.84 (m, 4H). MS (ESI) Calcd. for C$_{18}$H$_{17}$F$_2$N$_9$O$_3$S [M+H]$^+$ 478, Found 478.

Example 12

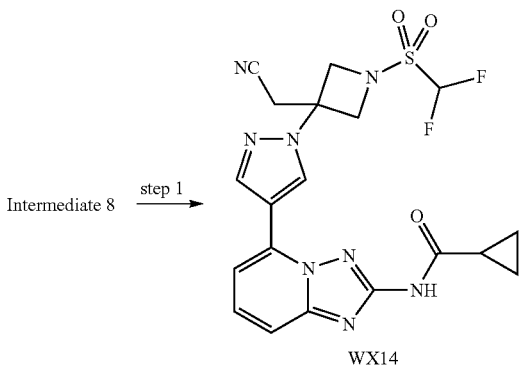

Step 1: Preparation of N-[5-[1-[3-(cyanomethyl)-1-(difluoromethylsulfonyl) azetidine-3-]pyrazole-4-]-[1,2,4]triazolo[1,5-c]pyridin-2-]cyclopropyl carboxamide (WX14)

Intermediate 8 (300 mg, 629.7 umol, trifluoroacetate) was suspended in DCM (4 mL). DMAP (8 mg, 63 umol), DIEA (407 mg, 3.2 mmol) and difluoromethylsulfonyl chloride (142 mg, 944.6 umol) was added in order. The reaction mixture was stirred at 15° C. for reacting for 12 hours. LC-MS showed that the raw material was completely reacted, and the target product was detected. The reaction mixture was concentrated under reduced pressure to remove DCM. The residue was diluted with DMF and MeOH to a solution (5 mL), and separated through preparative HPLC (alkalinity) to give N-[5-[1-[3-(cyanomethyl)-1-(difluoromethylsulfonyl)azetidine-3-]pyrazole-4-]-[1,2,4]triazolo[1,5-c]pyridin-2-]cyclopropyl carboxamide (8 mg, 2.7 yield). $^1$H NMR (400 MHz, METHANOL-d$_4$) δ=9.99 (s, 1H), 9.57-9.44 (m, 1H), 8.52-8.44 (m, 1H), 8.39 (d, J=7.3 Hz, 1H), 8.33 (d, J=8.3 Hz, 1H), 8.01-7.68 (m, 1H), 5.57 (d, J=8.8 Hz, 2H), 5.36 (d, J=9.0 Hz, 2H), 4.47 (s, 2H), 1.81-1.61 (m, 4H). MS (ESI) Calcd. for C$_{19}$H$_{18}$F$_2$N$_8$O$_3$S [M+H]$^+$ 477, Found 477.

Example 13

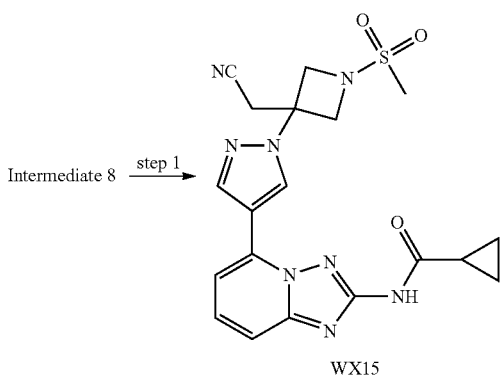

Intermediate 8 →(step 1)→ WX15

Step 1: Preparation of N-[5-[1-[3-(cyanomethyl)-1-methylsulfony-azetidine-3-]pyrazole-4-]-[1,2,4]triazolo[1,5-a]pyrimidin2-]cyclopropyl carboxamide Intermediate 8 (150 mg, 314.9 umol, trifluoroacetate) was suspended in dichloromethane (2 mL). DIEA (203 mg, 1.6 mmol), DMAP (11 mg, 94.5 mmol) and MsCl (180 mg, 1.6 mmol) was added in order. The reaction mixture was stirred at 15° C. for reacting for 12 hours. LC-MS showed that the raw material was completely reacted, and the target product was detected. The reaction mixture was concentrated under reduced pressure to remove DCM. The residue was diluted with MeOH to a solution (5 mL), and separated through preparative HPLC (alkalinity) to give N-[5-[1-[3-(cyanomethyl)-1-methylsulfony-azetidine-3-]pyrazole-4-]-[1,2,4]triazolo[1,5-a]pyrimidin2-]cyclopropyl carboxamide (10 mg, 7.15% yield). $^1$H NMR (400 MHz, DMSO-d$_6$) δ=11.17 (br. s., 1H), 9.27 (s, 1H), 8.79 (s, 1H), 7.83-7.68 (m, 1H), 7.62 (dd, J=7.8, 17.6 Hz, 2H), 4.51 (d, J=9.0 Hz, 2H), 4.34 (d, J=9.0 Hz, 2H), 3.69 (s, 2H), 3.16 (s, 3H), 2.25-2.00 (m, 1H), 0.95-0.80 (m, 4H). MS (ESI) Calcd. for C$_{19}$H$_{20}$N$_8$O$_3$S [M+H]$^+$ 441, Found 441.

Example 14

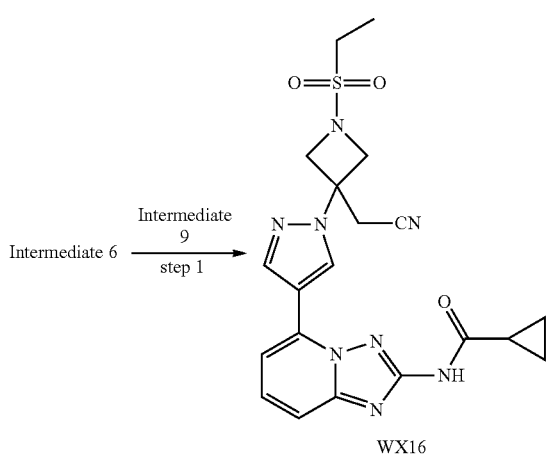

Intermediate 6 →(Intermediate 9, step 1)→ WX16

Step 1: Preparation of N-(5-(1-(3-(cyanomethyl)-1-(ethylsulfony)azetidine-3-yl)-1H-pyrazole-4-yl]-[1,2,4]triazolo[1,5-a]pyridin-2-yl)cyclopropyl carboxamide(WX16)

To a solution of Intermediate 6 (1.5 g, 5.6 mmol) and Intermediate 9 (1.5 g, 7.8 mmol) in acetonitrile (15 mL) was added dropwise DBU (1.7 g, 11.2 mmol) under the protection of nitrogen. The reaction mixture was stirred at 25° C. for 16 hours. TLC (petroleum ether/ethyl acetate=0:1) detected that the reaction was completed. The reaction mixture was poured into methanol (200 mL) at 0° C., a great number of solids were precipitated immediately, stirred for 10 min, and then filtered. The resulting solid was washed with methanol (5 mL) and dried under vacuum to give N-(5-(1-(3-(cyanomethyl)-1-(ethylsulfony)azetidine-3-yl)-1H-pyrazole-4-yl]-[1,2,4]triazolo[1,5-a]pyridin-2-yl)cyclopropyl carboxamide (1.60 g, 60% yield) as a product. $^1$H NMR (400 MHz, DMSO-d$_6$) δ=9.25 (s, 1H), 8.79 (s, 1H), 7.76-7.70 (m, 1H), 7.64 (d, J=7.0 Hz, 1H), 7.60 (d, J=8.5 Hz, 1H), 4.49 (d, J=9.0 Hz, 2H), 4.32 (d, J=9.0 Hz, 2H), 3.68 (s, 2H), 1.26 (t, J=7.3 Hz, 3H), 0.91-0.85 (m, 4H). MS (ESI) Calcd. for C$_{20}$H$_{22}$N$_8$O$_3$S [M+H]$^+$ 455, Found 455.

Example 15

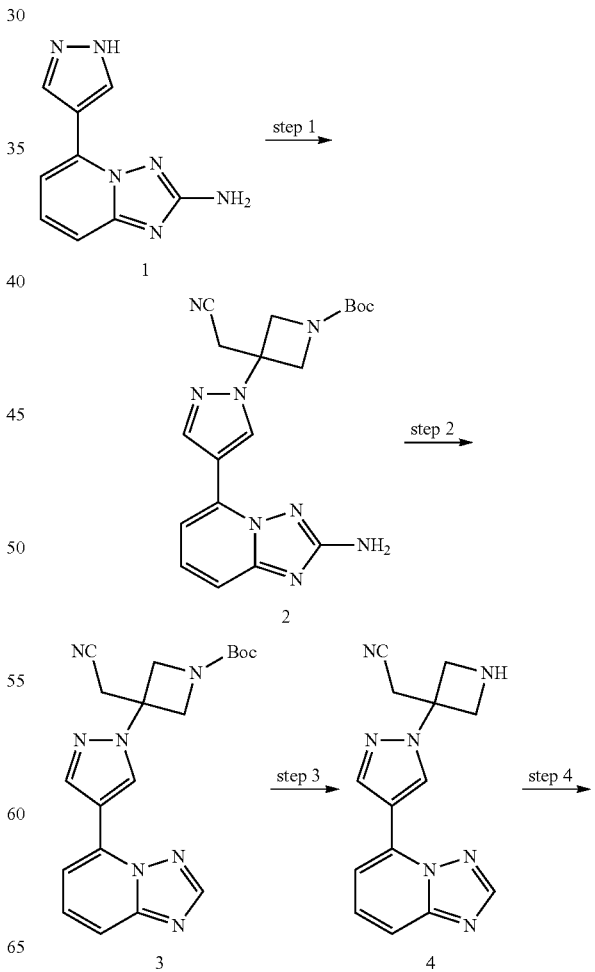

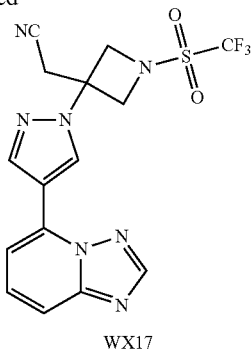

WX17

Step 1: Preparation of tert-butyl 3-[4-(2-amino-[1,2,4]triazolo[1,5-a]pyridin-1-]-3-(cyanoethyl) azetidine-1-formate To 5-(1H-pyrazole-4-)-[1,2,4]triazolo[1,5-a]pyridin-2-amine (700 mg, 3.5 mmol) and tert-butyl 3-(cyanomethyl)azetidine-1-formate (747 mg, 3.9 mmol), dissolved in acetonitrile (20.00 mL), was added DBU (1.6 g, 10.5 mmol). The mixture was reacted at 40° C. for 3 hour. LC-MS showed that the raw material was completely reacted, and the target product was detected. The reaction mixture was poured into water (30 mL), stirred for 30 min. The water phase was extracted with ethyl acetate (20 mL×3). The organic phase was combined, washed with saturated salt water (20 mL×2), dried with anhydrous sodium sulfate, filtered, and distilled under reduced pressure to give tert-butyl 3-[4-(2-amino-[1,2,4]triazolo[1,5-a]pyridin-1-]-3-(cyanoethyl) azetidine-1-formate (1.33 g, crude product) as a brown solid. MS (ESI) Calcd. for $C_{19}H_{22}N_8O_2$ [M+H]$^+$ 395, Found 395.

Step 2: Preparation of tert-butyl 3-(cyanomethyl-3-[4-([1,2,4]triazolo[1,5-a]pyridin-5-) pyrazole-1-]azetidine-1-formate To 3-[4-(2-amino-[1,2,4]triazolo[1,5-a]pyridin-1-]-3-(cyanoethyl)azetidine-1-formate (150 mg, 380.3 umol) dissolved in tetrahydrofuran (2 mL) was added t-BuONO (59 mg, 570.5 umol), and stirred at 15° C. for 3 hours. LC-MS showed that the raw material was completely reacted, and the target product was detected. The reaction mixture was concentrated under reduced pressure, diluted with DCM (4 mL), and separated through preparative TLC (DCM:MeOH=10:1) to give tert-butyl 3-(cyanomethyl-3-[4-([1,2,4]triazolo[1,5-a]pyridin-5-)pyrazole-1-]azetidine-1-formate (80 mg, 55.4% yield). MS (ESI) Calcd. for $C_{19}H_{21}N_7O_2$ [M+H]$^+$ 380, Found 380.

Step 3: Preparation of 2-[3-[4-([1,2,4]triazolo[1,5-a]pyridin-5-)pyrazole-1-] azetidine-3-]acetonitrile Tert-butyl 3-(cyanomethy-3-[4-([1,2,4]triazolo[1,5-a]pyridin-5-)pyrazole-1-]azetidine-1-formate (80 mg, 210.9 umol) was suspended in DCM (1.5 mL). Trifluoroacetic acid (857 mg, 7.5 mmol) was added, and stirred at 15° C. for 3 hours. LC-MS showed that the reaction was completed, and the target product MS was detected. The reaction mixture was concentrated under reduced pressure to remove solvent and the rest of trifluoroacetic acid to 2-[3-[4-([1,2,4]triazolo[1,5-a]pyridin-5-)pyrazole-1-]azetidine-3-]acetonitrile (129 mg, crude product) as brown dope. MS (ESI) Calcd. for $C_{14}H_{13}N_7$ [M+H]$^+$ 280, Found 280.

Step 4: Preparation of 2-[3-[4-([1,2,4]triazolo[1,5-a]pyridin-5-)pyrazole-1-]-1-(trifluoromethylsulfonyl)azetidine-3-]acetonitrile 2-[3-[4-([1,2,4]triazolo[1,5-a]pyridin-5-)pyrazole-1-]azetidine-3-]acetonitrile (60 mg, 214.8 umol) was dissolved in DCM (2 mL), DMAP (13 mg, 107.4 umol) and Et$_3$N (109 mg, 1.1 mmol) were added, then trifluoromethanesulfonyl chloride (47 mg, 279.3 umol) was add dropwise at 15° C. The reaction mixture was stirred at 15° C. for reacting for 4 hours. LC-MS showed that the raw material was completely reacted, and the target product MS was detected. The reaction mixture was concentrated under reduced pressure to remove solvent and give 2-[3-[4-([1,2,4]triazolo[1,5-a]pyridin-5-)pyrazole-1-]-1-(trifluoromethylsulfonyl)azetidine-3-]acetonitrile (25 mg, 28.3% yield) through preparative HPLC (alkalinity). $^1$H NMR (400 MHz, DMSO-d$_6$) δ=9.28 (br. s., 1H), 8.73 (d, J=17.8 Hz, 2H), 7.82 (br. s., 3H), 5.22-4.50 (m, 4H), 3.86 (br. s., 2H). MS (ESI) Calcd. for $C_{15}H_{12}F_3N_7O_2S$ [M+H]$^+$ 412, Found 412.

Example 16

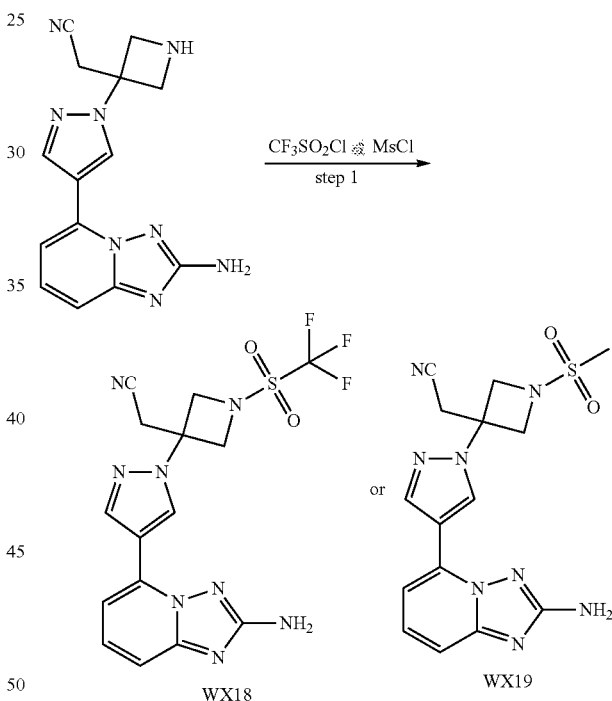

WX18  WX19

Step 1: Preparation of 2-(3-(4-(2-amino-[1,2,4]triazolo[1,5-a]pyridinyl)-1H-pyrazolyl)-1-(trifluoromethyl sulfonyl)cyclobutane)acetonitrile(WX18)

2-(3-(4-(2-amino-[1,2,4]triazolo[1,5-a]pyridinyl)-1H-pyrazolyl)cyclobutane-3) acetonitrile (200 mg, 489.8 umol) was dissolved in DCM (10 mL), and TEA (198 mg, 2 mmol) was added. The resulting mixture was cooled to 0° C., then trifluoromethanesulfonyl chloride (107 mg, 636 umol) was slowly added dropwise. After dropwise adding, the reaction was warmed to room temperature and reaction was carried out at room temperature for 12 hours. LC-MS showed that the reaction was completed. The solvent was spun dry under reduced pressure. The residue was dissolved with DMF, further purified and freeze-dried through preparative HPLC (HCl) to give 2-(3-(4-(2-amino-[1,2,4]triazolo[1,5-a]pyridinyl)-1H-pyrazolyl)-1-(trifluoromethylsulfonyl)cyclobutane)acetonitrile. $^1$H-NMR (400 MHz, MeOD-d$_4$) δ=9.14 (s, 1H), 8.56 (s, 1H), 7.58 (t, J=7.8, 1H), 7.41 (d, J=7.5 Hz, 1H), 7.30 (d, J=8.8 Hz, 1H), 4.98 (d, J=9.3 Hz, 2H), 4.68 (d, J=9.0 Hz, 2H), 3.67 (s, 2H). MS (ESI) Calcd. for $C_{15}H_{13}F_3N_8O_2S$ [M+H]$^+$ 427, Found 427.

Preparation of WX19: WX19 was prepared in the same method as the preparation of WX18 (Step 1). It was purified and freeze-dried through preparative HPLC (HCl) to give 2-(3-(4-(2-amino-[1,2,4]triazolo[1,5-a]pyridinyl)-1H-pyrazolyl)-1-(methylsulfonyl) cyclobutane)acetonitrile. $^1$H-NMR (400 MHz, MeOD-d$_4$) δ=9.13 (s, 1H), 8.53 (s, 1H), 7.57 (m, 1H), 7.41 (d, J=6.8 Hz, 1H), 7.30 (d, J=8.5 Hz, 1H), 4.64 (d, J=9.3 Hz, 2H), 4.35 (d, J=9.3 Hz, 2H), 3.62 (s, 2H), 3.08 (s, 3H). MS (ESI) Calcd. for $C_{15}H_{16}N_8O_2S$[M+H]$^+$ 373, Found 373.

Example 17

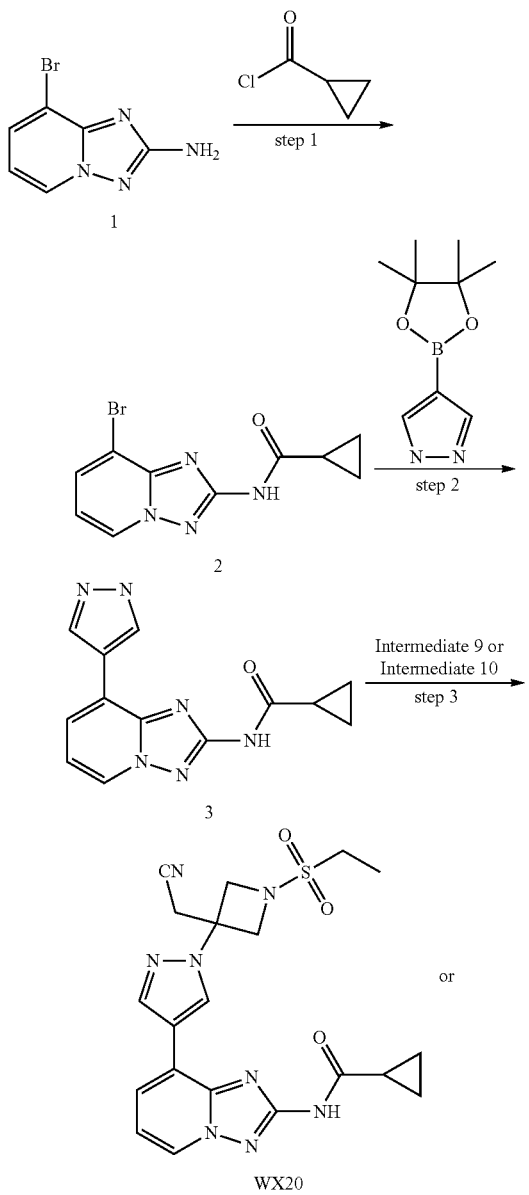

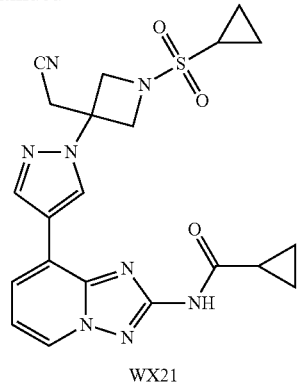

WX21

Step 1: Preparation of N-(8-bromo-[1,2,4]triazolo[1,5-a]pyridin-2-yl) cyclopropanecarboxamide To 8-bromo-[1,2,4]triazolo[1,5-a]pyridin-2-amine (1.0 g, 4.7 mmol) and triethylamine (1.4 g, 14.1 mmol), dissolved in acetonitrile (15.0 mL), was added dropwise cyclopropanecarboxylic acid chloride (1.5 g, 14.1 mmol). Then the mixture is stirred at 26° C. for reacting for 12 hours. LC-MC showed that the reaction was completed. The reaction mixture was distilled under reduced pressure to remove acetonitrile. The residue was added to H$_2$O (5 mL) and water layer was extracted with DCM (15 mL×3). The organic phase was combined, washed with saturated salt water (15 mL), dried with anhydrous sodium sulfate, filtered, and distilled under reduced pressure to remove the filtrate. The residue was purified through silica gel column chromatography (DCM/MeOH=20/1) to give a yellow solid (700 mg, 47.8% yield). MS (ESI) Calcd. for $C_{10}H_9N_4OBr$ [M+H]$^+$ 282, Found 282.

Step 2: Preparation of N-[8-(1H-pyrazole-4-yl)-[1,2,4]triazolo[1,5-a]pyridin-2-yl) cyclopropanecarboxamide To N-(8-bromo-[1,2,4]triazolo[1,5-a]pyridin-2-yl) cyclopropanecarboxamide (700 mg, 2.5 mmol) and 4-(4,4,5,5-tetramethyl-1,3,2-dioxaborolan-2-yl)-1H-pyrazole (579 mg, 3.0 mmol), dissolved in dioxane (25 mL) and water (6 mL), was respectively added potassium carbonate (1.0 g, 7.5 mmol) and Pd(dppf)Cl$_2$ (182 mg, 249 umol). The system is vacuumed and filled with nitrogen. Then the mixture is heated to reflux for 1 hour. LC-MC showed that the reaction was completed. The reaction mixture was distilled under reduced pressure to remove the solvent. The residue was dissolved in DCM (50 mL) and water (10 mL). The organic layer was separated and the water layer was extracted with DCM (2×50 mL) twice. The organic phase was combined, washed with saturated salt water (10 mL), dried with anhydrous sodium sulfate, filtered, and distilled under reduced pressure to remove the filtrate. The residue was purified through silica gel column chromatography (EA/PE=3/1 to 1/1) to give a yellow solid (300 mg, 40.4% yield). MS (ESI) Calcd. for $C_{13}H_{12}N_6O$ [M+H]$^+$ 269, Found 269.

Step 3: Preparation of compound of N-(8-(1-(3-(cyanomethyl)-1-(ethylsulfonyl) azetidine-3-yl)-1H-pyrazole-4-yl)-[1,2,4]triazolo[1,5-a]pyridin-2-yl) cyclopropanecarboxamide(WX20)

To N-[8-(1H-pyrazole-4-yl)-[1,2,4]triazolo[1,5-a]pyridin-2-yl) cyclopropanecarboxamide (100 mg, 372.8 umol)

and 2-(1-ethylsulfonyl azetidine-3-yl) acetonitrile (83 mg, 447.3 umol), dissolved in acetonitrile (15 mL), was added dropwise DBU (68 mg, 447.3 umol). The formed mixture was stirred at 26° C. for reacting for 12 hours. After TLC showed that the reaction was completed, the reaction mixture was distilled under reduced pressure to remove the solvent. The residue was dissolved in DCM (15 mL) and water (10 mL). The organic layer was separated and the water layer was extracted with DCM (15 mL×2) twice. The organic phase was combined, washed with saturated salt water (10 mL), dried with anhydrous sodium sulfate, filtered, and distilled under reduced pressure to remove the filtrate. The residue was purified through preparative HPLC (alkaline method) to give (WX20)(65 mg, 37.98% yield): $^1$H NMR (400 MHz, METHANOL-d$_4$) δ=8.72 (s, 1H), 8.37 (d, J=6.8 Hz, 1H), 8.28 (s, 1H), 7.71 (d, J=7.3 Hz, 1H), 6.98 (t, J=7.0 Hz, 1H), 4.63 (d, J=9.0 Hz, 2H), 4.28 (d, J=9.0 Hz, 2H), 3.58 (s, 2H), 3.20 (q, J=7.3 Hz, 2H), 1.44-1.31 (m, 3H), 1.07 (quin, J=3.8 Hz, 2H), 0.96 (qd, J=3.7, 7.3 Hz, 2H). MS (ESI) Calcd. for $C_{20}H_{22}N_8O_3S$ [M+H]$^+$ 455, Found 455.

Preparation of WX21: WX21 was prepared in the same method as the preparation of WX20 (Step 3). $^1$H NMR (400 MHz, CDCl$_3$) δ=8.93-8.82 (m, 1H), 8.67 (s, 1H), 8.42 (d, J=6.3 Hz, 1H), 8.15 (s, 1H), 7.63 (d, J=7.3 Hz, 1H), 6.96 (t, J=7.2 Hz, 1H), 4.62 (d, J=9.3 Hz, 2H), 4.25 (d, J=9.3 Hz, 2H), 3.42 (s, 2H), 2.54-2.42 (m, 1H), 1.87 (br. s., 1H), 1.25-1.17 (m, 4H), 1.13-1.06 (m, 2H), 0.94 (dd, J=3.0, 7.5 Hz, 2H). MS (ESI) Calcd. for $C_{21}H_{22}N_8O_3S$ [M+H]$^+$ 467, Found 467.

Example 18

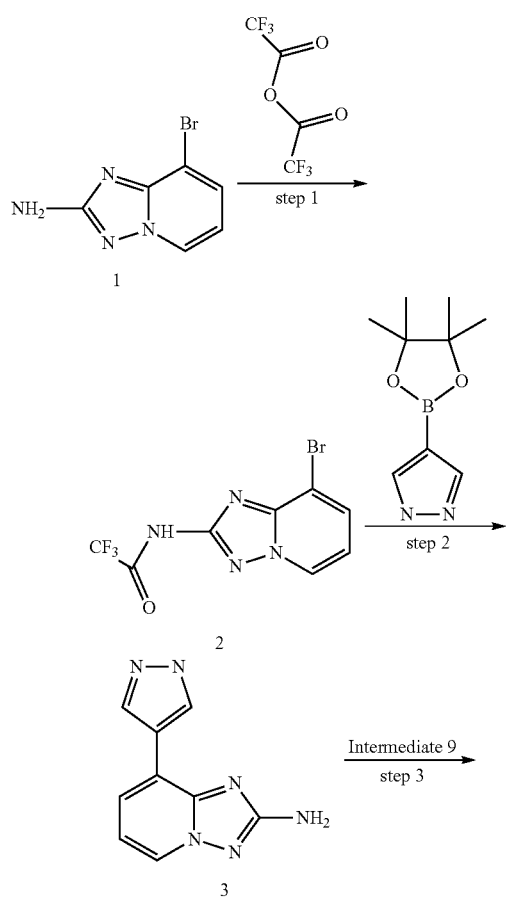

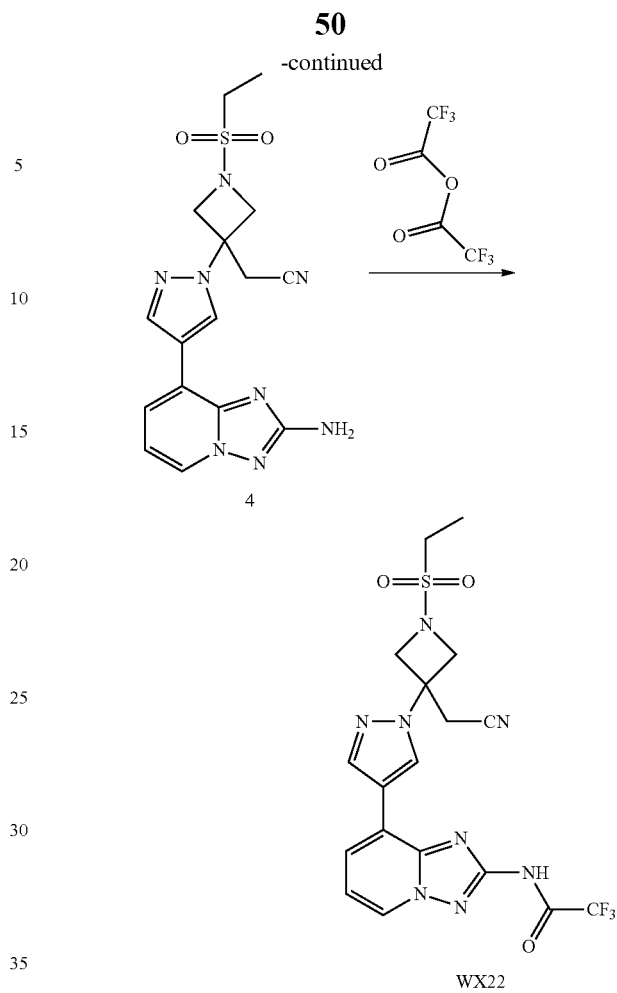

Step 1: Preparation of N-(8-bromo-[1,2,4]triazolo[1,5-a]pyridin-2-yl)-2,2,2-trifluoro-acetamide To a solution of 8-bromo-[1,2,4]triazolo[1,5-a]pyridin-2-amine (1.0 g, 4.7 mmol) and triethylamine (1.4 g, 14.1 mmol) dissolved in dichloromethane (25.00 mL), was added dropwise trifluoroacetic acid (3.0 g, 14.1 mmol). The formed reaction mixture was stirred at 26° C. for reacting for 12 hours. After LC-MS showed that the reaction was completed, the reaction mixture was distilled under reduced pressure to remove the solvent. The residue was dissolved in DCM (50 mL) and saturated water (10 mL). The organic layer was separated and the water layer was extracted with DCM (50 mL×2) twice. The organic phase was combined, washed with saturated salt water (10 mL), dried with anhydrous sodium sulfate, filtered, and distilled under reduced pressure to remove the filtrate to give N-(8-bromo-[1,2,4]triazolo[1,5-a]pyridin-2-yl)-2,2,2-trifluoro-acetamide (1.1 g) as a crude product which was used directly without purification. MS (ESI) Calcd. for $C_8H_4N_4OBrF_3$ [M+H]$^+$ 310, Found 310.

Step 2: Preparation of 8-(1H-pyrazole-4-yl)-[1,2,4]triazolo[1,5-a]pyridin-2-amine To N-(8-bromo-[1,2,4]triazolo[1,5-a]pyridin-2-yl)-2,2,2-trifluoro-acetamide (1.1 g, 3.6 mmol) and 4-(4,4,5,5-tetramethyl-1,3,2-dioxaborolan-2-yl)-1H-pyrazole (1.0 g, 356 umol), dissolved in dioxane (25 mL) and water (6 mL), was respectively added potassium carbonate (492 mg, 3.6 mmol) and Pd(dppf)Cl$_2$ (260 mg, 356 umol). The system is vacuumed and filled with nitrogen. Then the mixture was heated to reflux for 1 hour. After LC-MC showed that the reaction was completed, the reaction mixture was filtered, and the filtrate was washed with water (10 mL) and then extracted with EA (30 mL×3). The organic phase was combined, washed with saturated salt water (10 mL), dried with anhydrous sodium sulfate, filtered, and distilled under reduced pressure to remove the filtrate. The residue was purified through silica gel column chromatography (DCM/MeOH=DCM to 20/1) to give (430 mg, 57.3% yield) as a yellow solid. MS (ESI) Calcd. for C$_9$H$_8$N$_6$ [M+H]$^+$ 201, Found 201.

Step 3: Preparation of 2-[3-[4-(2-amino-[1,2,4]triazolo[1,5-a]pyridine-8-yl)pyrazole-1-yl]-1-ethyl sulfonyl-azetidine-3-yl] acetonitrile To 8-(1H-pyrazole-4-yl)-[1,2,4]triazolo[1,5-a]pyridin-2-amine (50 mg, 249.7 umol) and 2-(1-ethylsulfonyl-azetidine-3-ylene) acetonitrile (56 mg, 299.7 umol), dissolved in acetonitrile (8 mL), was added dropwise DBU (46 mg, 299.7 umol). The reaction mixture was stirred at 26° C. for reacting for 12 hours. After LC-MS showed that the reaction was completed, the reaction mixture was distilled under reduced pressure to remove acetonitrile. To the residue was added water (10 mL), and then extracted with EA (10 mL×3). The organic phase was combined, washed with saturated salt water (10 mL), dried with anhydrous sodium sulfate, filtered, and distilled under reduced pressure to remove the filtrate. The residue was purified through silica gel column chromatography (DCM/MeOH=20/1) to give 2-[3-[4-(2-amino-[1,2,4]triazolo[1,5-a]pyridine-8-yl)pyrazole-1-yl]-1-ethylsulfonylazetidine-3-yl]acetonitrile (50 mg, 49.22% yield) as a white solid. MS (ESI) Calcd. for C$_{16}$H$_{18}$N$_8$SO$_2$[M+H]$^+$ 387, Found 387.

Step 4: Preparation of N-(8-(1-(3-(cyanomethyl)-1-(ethylsulfonyl)azetidine-3-yl)-1H-pyrazole-4-yl)-[1,2,4]triazolo[1,5-a]pyridin-2-yl)-2,2,2-trifluoroacetamide(WX22)

To a solution of 2-[3-[4-(2-amino-[1,2,4]triazolo[1,5-a]pyridine-8-yl)pyrazole-1-yl]-1-ethylsulfonyl-azetidine-3-yl] acetonitrile (50 mg, 129.4 umol) and triethylamine (39.28 g, 388.2 umol) dissolved in dichloromethane (5 mL), was added dropwise trifluoroacetic anhydride (81.5 mg, 388.2 umol). The reaction mixture was stirred at 26° C. for reacting for 12 hours. After TLC showed that the reaction was completed, H$_2$O (5 mL) was added and the organic layer was separated, the water layer was extracted with DCM (15 mL×3) twice. The organic phase was combined, washed with saturated salt water (10 mL), and washed with saturated salt water (10 mL), dried with anhydrous sodium sulfate, filtered, and distilled under reduced pressure to remove the filtrate. The residue was purified through preparative thin layer chromatography (DMC:MeOH=20:1) to give (WX22) (29 mg, 46.5% yield). $^1$H NMR (400 MHz, METHANOL-d$_4$) δ=8.93-8.89 (m, 1H), 8.63-8.59 (m, 1H), 8.48 (s, 1H), 8.02 (dd, J=1.0, 7.3 Hz, 1H), 7.28-7.21 (m, 1H), 4.68-4.58 (m, 4H), 4.32 (s, 2H), 3.60 (s, 2H), 3.19 (q, J=7.4 Hz, 2H), 1.38 (t, J=7.3 Hz, 3H). MS (ESI) Calcd. for C$_{18}$H$_{17}$N$_8$SO$_3$F$_3$ [M+H]$^+$483, Found 483.

Example 19

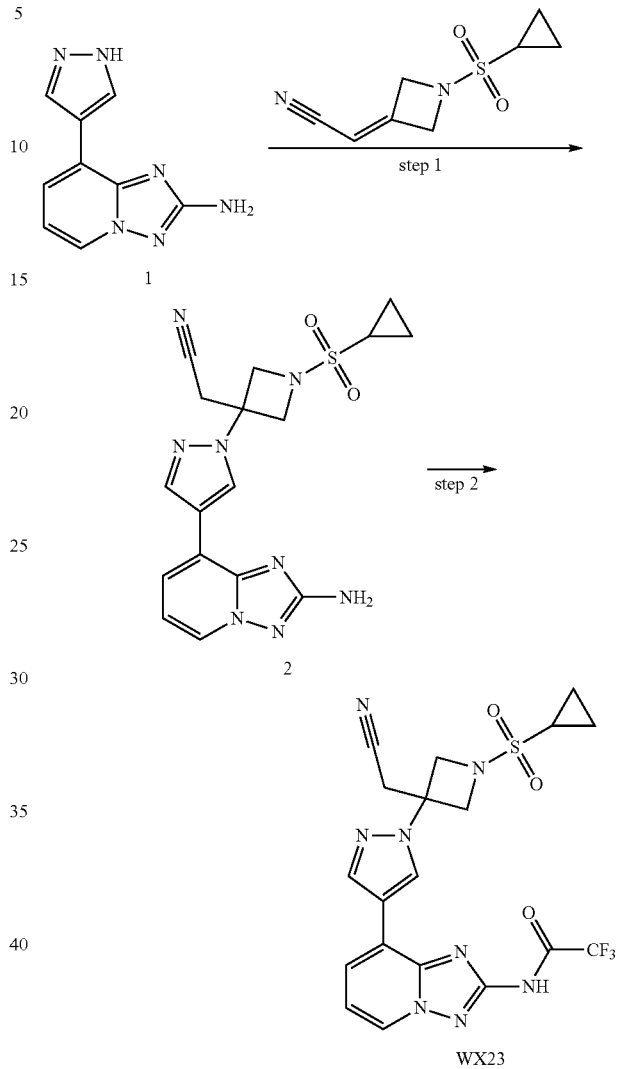

Step 1: Preparation of 2-[3-[4-(2-amino-[1,2,4]triazolo[1,5-a]pyridine-8-yl)pyrazole-1-yl]-1-cyclopropylsulfonyl-azetidine-3-yl]acetonitrile To 8-(1H-pyrazole-4-yl)-[1,2,4]triazolo[1,5-a]pyridin-2-amine (250 mg, 1.3 mmol) and 2-(1-cyclopropylsulfonyl-azetidine-3-ylene)acetonitrile (297 mg, 1.5 mmol), dissolved in acetonitrile (25.00 mL), was added dropwise DBU (228 mg, 1.5 mmol). The reaction mixture was stirred at 26° C. for reacting for 12 hours. After LC-MS showed that the reaction was completed, H$_2$O (5 mL) was added and the organic layer was separated, the water layer was extracted with DCM (2×15 mL) twice. The organic phase was combined, washed with saturated salt water (15 mL), dried with anhydrous sodium sulfate, filtered, and distilled under reduced pressure to remove the filtrate. The residue was purified through silica gel column chromatography (DCM/MeOH=20/1) to give 2-[3-[4-(2-amino-[1,2,4]triazolo[1,5- a]pyridine-8-yl) pyrazole-1-yl]-1-cyclopropylsulfonyl-azetidine-3-yl]acetonitrile (250 mg, 45.2% yield) as a yellow solid. MS (ESI) Calcd. for $C_{17}H_{18}N_8SO_2[M+H]^+$ 399, Found 399.

Step 2. Preparation of WX23

To 2-[3-[4-(2-amino-[1,2,4]triazolo[1,5-a]pyridine-8-yl) pyrazole-1-yl]-1-cyclopropylsulfonyl-azetidine-3-yl]acetonitrile (50 mg, 125.5 umol) and triethylamine (38 g, 376.5 umol) dissolved in DCM (5 mL), was added dropwise trifluoroacetic anhydride (79 mg, 376.5 umol). The reaction mixture was stirred at 26° C. for reacting for 12 hours. After LC-MS showed that the reaction was completed, $H_2O$ (5 mL) was added and the organic layer was separated, the water layer was extracted with DCM (2×15 mL) twice. The organic phase was combined, washed with saturated salt water (15 mL), dried with anhydrous sodium sulfate, filtered, and distilled under reduced pressure to remove the filtrate. The residue was purified through preparative HPLC (alkalinity, 0-60) to give (WX23)(17 mg, 27.4% yield). $^1H$ NMR $^1H$ NMR (400 MHz, $CDCl_3$) δ=9.09-9.04 (m, 1H), 8.74 (s, 1H), 8.55-8.52 (m, 1H), 8.19 (s, 1H), 7.79-7.74 (m, 1H), 7.12 (t, J=7.0 Hz, 1H), 4.64 (d, J=9.3 Hz, 2H), 4.27 (d, J=9.3 Hz, 2H), 3.44 (s, 2H), 2.50-2.43 (m, 1H), 1.25-1.21 (m, 2H), 1.15-1.08 (m, 2H). MS (ESI) Calcd. for $Cl_9H_{17}N_8SO_3$ $[M+H]^+$ 495, Found 495.

Example 20

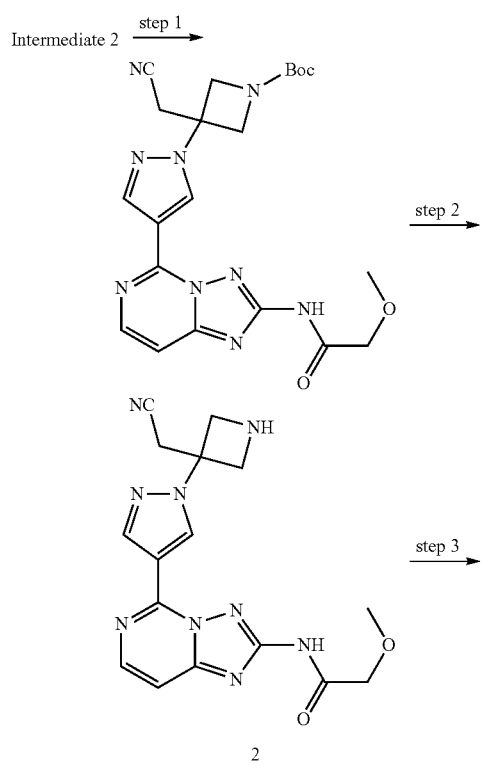

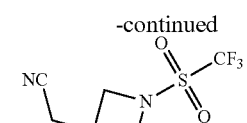

or

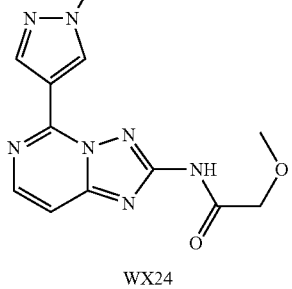

WX24

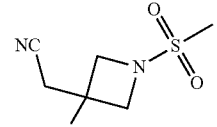

WX25

Step 1: Preparation of tert-butyl 3-(cyanomethyl)-3-(4-(2-(2-methoxyacetamide)-[1,2,4]triazolo[1,5-c]pyridin-5-yl]-1H-pyrazole-1-yl)azetidine-1-carboxylate (1)

To Intermediate 2 (0.1 g, 0.25 mmol) and triethylamine (0.15 mL, 1.2 mmol) dissolved in DMF (10.00 mL) was added 2-methoxyacetyl chloride (65 mg, 0.5 mmol). The resulting mixture was stirred at 60° C. for reacting for 16 hours until LC-MS showed that the reaction was completed. The mixture was poured into 10 ml of water and extracted with ethyl acetate (10 ml×3). The organic phase was combined, washed with saturated salt water (20 mL), dried with anhydrous sodium sulfate, and concentrated to give a crude product (120 mg) which was directly used in the next step. MS (ESI) Calcd. for $C_{21}H_{25}N_9O_4[M+H^+]$ 468, Found 468.

Step 2: Preparation of N-(5-(1-(3-(cyanomethyl) azetidine-3-yl)-1H-pyrazole-4-yl)-[1,2,4]triazolo[1,5-c]pyridin-2-yl)-2-methoxyacetamide (2)

Tert-butyl 3-(cyanomethyl)-3-(4-(2-(2-methoxyacetamide)-[1,2,4]triazolo[1,5-c]pyridin-5-yl]-1H-pyrazole-1-yl)azetidine-1-carboxylate (100 mg, 0.2 mmol) was dissolved in dichloromethane (5 mL), and then TFA (5 ml) was added. The resulting mixture was stirred at 10° C. for reacting for 1 hour. LC-MS showed that the reaction was completed and the solvent was concentrated to give 100 mg of crude product which was directly used in the next step. MS (ESI) Calcd. for $C_{16}H_{17}N_9O_2[M+H]^+$ 482, Found 482.

Step 3: Preparation of N-(5-(1-(3-(cyanomethyl)-1-((trifluoromethyl)sulfonyl) azetidine-3-yl)-1H-pyrazole-4-yl)-[1,2,4]triazolo[1,5-c]pyridin-2-yl)-2-methoxyacetamide (WX24)

N-(5-(1-(3-(cyanomethyl)azetidine-3-yl)-1H-pyrazole-4-yl)-[1,2,4]triazolo[1,5-c]pyridin-2-yl)-2-methoxyacetamide (50 mg, 0.14 mmol) was dissolved in dichloromethane (5 mL), triethylamine (42 mg, 0.4 mmol) and then trifluoromethanesulfonyl chloride (47 mg, 0.28 mmol) was added. The resulting mixture was stirred at 10° C. for reacting 1 hour. LC-MS showed that the reaction was completed and the solvent was concentrated to give a crude product (50 mg). The crude product was separated through preparative HPLC (alkalinity) to give N-(5-(1-(3-(cyanomethyl)-1-((trifluoromethyl)sulfonyl)azetidine-3-yl)-1H-pyrazole-4-yl)-[1,2,4]triazolo[1,5-c]pyridin-2-yl)-2-methoxyacetamide (WX24, 10 mg) as a white solid. $^1$H NMR (400 MHz, DMSO-$d_6$) 9.30 (s, 1H), 8.89 (s, 1H), 8.36 (d, J=6.27 Hz, 1H), 7.66 (d, J=6.02 Hz, 1H), 4.74 (s, 2H), 3.86 (s, 2H), 3.40 (s, 4H). MS (ESI) Calcd. for $C_{17}H_{16}F_3N_9O_4S$ [M+H]$^+$ 495, Found 495.

Preparation of WX25: N-(5-(1-(3-(cyanomethyl)-1-((methylsulfonyl)azetidine-3-yl)-1H-pyrazole-4-yl)-[1,2,4]triazolo[1,5-c]pyridin-2-yl)-2-methoxyacetamide(WX25) was prepared in the same method as the preparation of WX24 (Step 3). $^1$H NMR (400 MHz, CDCl$_3$) δ=9.29-9.32 (m, 1H), 8.67-8.71 (m, 1H), 8.28-8.33 (m, 1H), 7.44-7.48 (m, 1H), 4.60-4.68 (m, 1H), 4.30-4.36 (m, 2H), 4.13-4.19 (m, 1H), 3.58 (s, 2H), 3.41-3.48 (m, 1H), 3.04 (s, 3H), 1.45 (s, 3H). MS (ESI) Calcd. for $C_{17}H_{19}N_9O_4S$ [M+H]$^+$ 446, Found 446.

Example 21

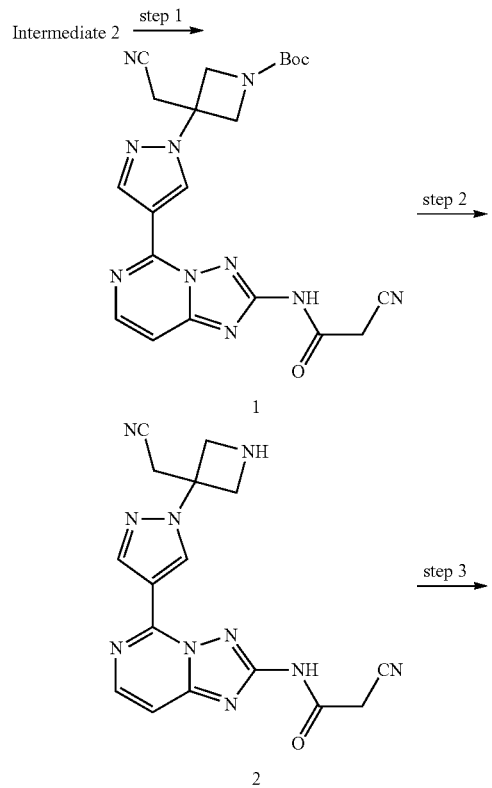

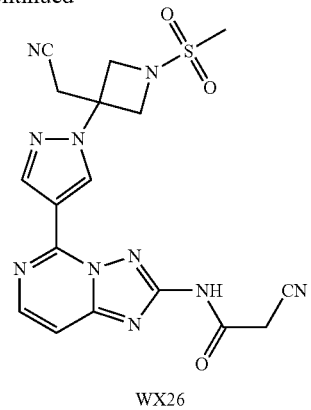

Step 1: Preparation of tert-butyl 3-(4-(2-(2-cyanoacetamide)-[1,2,4]triazolo[1,5-c]pyridin-5-yl)-1H-pyrazole-1-yl)-3-(cyanomethyl)azetidine-1-carboxylate (1)

To Intermediate 2 (0.1 g, 0.3 mmol) and triethylamine (0.17 ml, 1.3 mmol), dissolved in DMF (10 mL), was added 2-cyanoacetyl chloride (131 mg, 1.3 mmol). The resulting mixture was stirred at 60° C. for reacting for 2 hours until LC-MS showed that the reaction was completed. The mixture was poured into water (10 mL) and extracted with ethyl acetate (10 mL×3). The organic phase was combined, dried with anhydrous sodium sulfate, and concentrated to give tert-butyl 3-(4-(2-(2-cyanoacetamide)-[1,2,4]triazolo[1,5-c]pyridin-5-yl)-1H-pyrazole-1-yl)-3-(cyanomethyl)azetidine-1-carboxylate (100 mg, crude product) which was directly used in the next step. MS (ESI) Calcd. for $C_{21}H_{22}N_{10}O_3$ [M+H]$^+$ 463, Found 463.

Step 2: Preparation of 2-cyano-N-(5-(1-(3-(cyanomethyl)azetidine-3-yl)-1H-pyrazole-4-yl)-[1,2,4]triazolo[1,5-c]pyridin-2-yl)acetamide (2)

Tert-butyl 3-(4-(2-(2-cyanoacetamide)-[1,2,4]triazolo[1,5-c]pyridin-5-yl)-1H-pyrazole-1-yl)-3-(cyanomethyl)azetidine-1-carboxylate (1)(100 mg, 0.2 mmol) was dissolved in dichloromethane (5 mL) and TFA (5 mL) was added. The resulting mixture was stirred at 10° C. for reacting for 1 hour, LC-MS showed that the reaction was completed. The solvent was concentrated to give 2-cyano-N-(5-(1-(3-(cyanomethyl)azetidine-3-yl)-1H-pyrazole-4-yl)-[1,2,4]triazolo[1,5-c]pyridin-2-yl)acetamide (2)(100 mg, crude product) which was directly used in the next step. MS (ESI) Calcd. for $C_{16}H_{14}N_{10}O$[M+H]$^+$ 463, Found 463.

Step 3: Preparation of 2-cyano-N-(5-(1-(3-(cyanomethyl)-1-(methanesulfonamide) azetidine-3-yl)-1H-pyrazole-4-yl)-[1,2,4]triazolo[1,5-c]pyridin-2-yl) acetamide (WX26)

2-cyano-N-(5-(1-(3-(cyanomethyl)azetidine-3-yl)-1H-pyrazole-4-yl)-[1,2,4]triazolo[1,5-c]pyridin-2-yl)acetamide (50 mg, 0.14 mmol) was dissolved in dichloromethane (5 mL), triethylamine (42 mg, 0.4 mmol) and methanesulfonyl chloride (47 mg, 0.28 mmol). The resulting mixture was stirred at 10° C. for reacting for 1 hour, LC-MS showed that the reaction was completed. The solvent was concentrated to give 50 mg of crude product. The crude product was separated through preparative HPLC (alkalinity) to give 2-cyano-N-(5-(1-(3-(cyanomethyl)-1-(methanesulfonamide) azetidine-3-yl)-1H-pyrazole-4-yl)-[1,2,4]triazolo[1,5-c]pyridin-2-yl)acetamide(WX26 10 mg). $^1$H NMR (400 MHz, DMSO-d$_6$) 9.27 (s, 1H), 8.83 (s, 1H), 8.25-8.52 (m, 1H), 7.67 (d, J=6.27 Hz, 1H), 4.56 (d, J=9.29 Hz, 4H), 4.34 (d, J=9.29 Hz, 4H), 3.73 (s, 3H)$_○$ MS (ESI) Calcd. for C$_{17}$H$_{16}$N$_{10}$O$_3$S[M+H]$^+$ 441, Found 441.

Example 22

Step 1: Preparation of 1-(3-bromophenyl) thiourea(2)

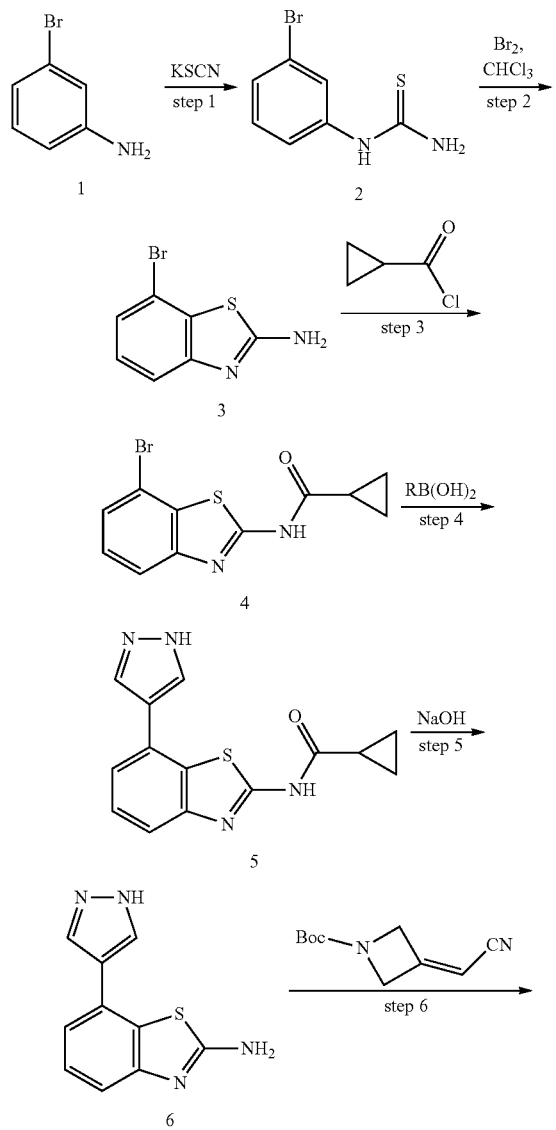

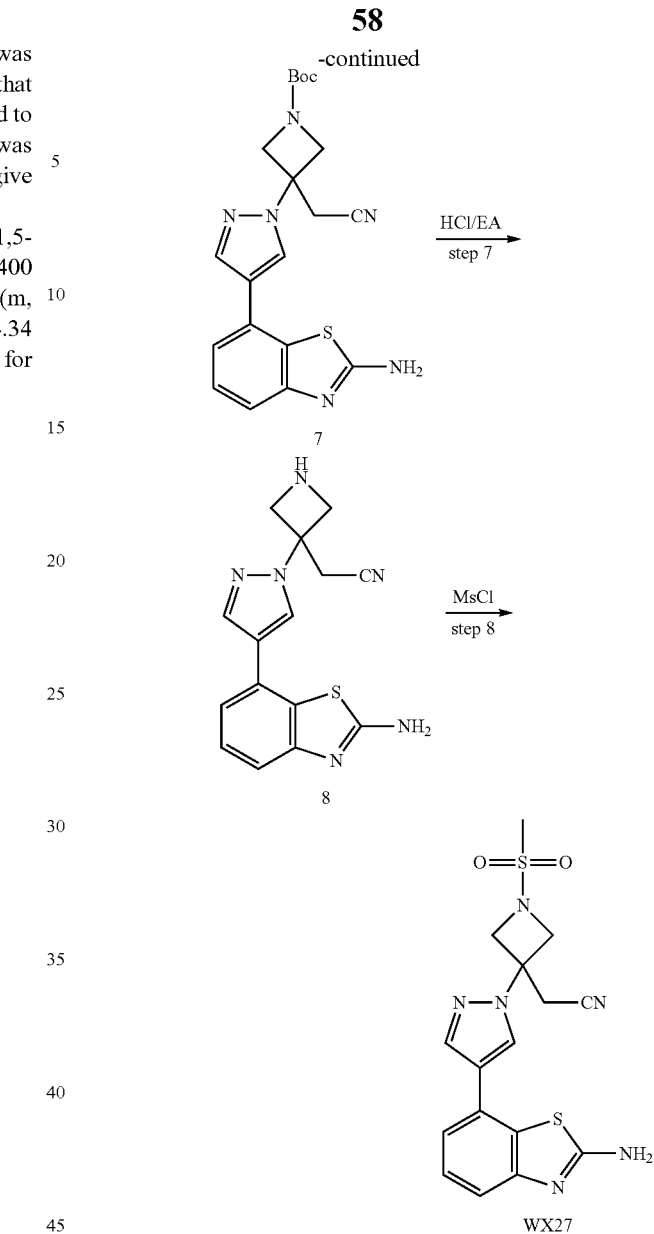

To a dilute hydrochloric acid solution (1M, 50 mL) of 3-bromaniline (30.0 g, 174 mmol) was added potassium thiocyanate (20.0 g, 205.8 mmol) at room temperature. The mixture was stirred at 100° C. for reacting for 12 hours. TLC (PE:EA=1:1) detected that there was part of 3-bromaniline left (about 20%). The reaction mixture was cooled to 0° C., then was alkalified with ammonium hydroxide to pH=10. The resulting violet emulsion was stirred continuously for half an hour and then extracted with ethyl acetate (200 mL×4). The organic phase was combined, washed with saturated salt water (30 mL), dried with anhydrous sodium sulfate, and filtered and spun dry to give thick violet suspension. Until a little cool, dichloromethane (50 mL) was added and then cooled to 0° C. in ice bath. After suction filtration of insoluble lavender solid, washed with a small amount of dichloromethane (10 mL×2), and dried under vacuum to give 1-(3-bromophenyl) thiourea (25 g, 55.8% yield). $^1$H NMR (400 MHz, CDCl3) □07.46 (s, 1H), 7.39-7.44 (m, 1H), 7.28-7.32 (m, 1H), 7.25 (s, 1H). MS (ESI) Calcd. for C$_7$H$_7$BrN$_2$S [M+H]$^+$ 230, Found 230.

Step 2: Preparation of 7-bromobenzo[d]thiazole-2-amine(3)

To 1-(3-bromophenyl) thiourea (5.0 g, 21.6 mmol) in acetic acid (50 mL) was added dropwise a solution of liquid bromine (4.7 g, 29.2 mmol) in chloroform (5 mL) at 0° C. The mixture was stirred at 85° C. for reacting for 3 hours. TLC (PE:EA=1:1) showed that raw material was completely reacted, and two points were obtained. The reaction mixture was filtered while it was hot. The insoluble solid was washed with a small amount of dichloromethane (10 mL×2) and dried to give a product as yellow solid (4.2 g, 50% yield). The filtrate was spun dry to give yellow suspension, and the residue was beat with dichloromethane (20 mL). After suction filtration of the insoluble substance, washed with DCM (5 mL×2), and dried under vacuum to give a product as a yellow solid (1.2 g, 13% yield). One part of the product P1 and P2 were dissolved in water (1 mL) respectively, alkalified with ammonium hydroxide to pH=10 and then extracted with ethyl acetate (0.2 mL). The two extracts were blew-dry with nitrogen, and were used directly for NMR detection. NMR showed that there was mainly a by-product of 5-bromide isomers in P1 and mainly 7-bromide product. The resulting crude product was directly used in the next step without further purification. $^1$H NMR (400 MHz, DMSO-d$_6$) □07.13-7.16 (m, 1H), 7.16-7.22 (m, 2H), 7.32 (dd, J=7.28, 1.51 Hz, 1H), 7.48 (d, J=1.76 Hz, 1H), 7.62 (d, J=8.53 Hz, 1H), 7.71 (br. s., 1H), 7.73 (s, 2H). MS (ESI) Calcd. for C$_7$H$_5$BrN$_2$S[M+H]$^+$ 228, Found 228.

Step 3: Preparation of N-(7-bromobenzo[d]thiazole-2-yl)cyclopropyl carboxamide (4)

To 7-bromobenzo[d]thiazole-2-amine (1.2 g, 3.9 mmol, HBr salt) and triethylamine (1.6 g, 15.5 mmol) in acetonitrile (50 mL) was added dropwise cyclopropanecarbonyl chloride (1.2 g, 11.6 mmol) at 0° C. under the protection of nitrogen. The mixture was stirred at 30° C. for reacting for 12 hours. TLC (PE:EA=1:1) detected and showed that the main point was the desired mono-substituted product. The reaction mixture was quenched with water (60 mL) and extracted with ethyl acetate (30 mL×3). The organic phase was combined, washed with saturated salt water (5 mL), dried with anhydrous sodium sulfate, and filtered and spun dry. The residue was purified through column chromatography (PE:EA=5:1) to give N-(7-bromobenzo[d]thiazole-2-yl) cyclopropyl carboxamide (580 mg, 40% yield) as a yellow solid. $^1$H NMR (400 MHz, DMSO-d$_6$) δ=12.85 (s, 1H), 7.75 (d, J=8.03 Hz, 1H), 7.52 (d, J=7.78 Hz, 1H), 7.38-7.43 (m, 1H), 1.98-2.05 (m, 1H), 0.95-1.02 (m, 4H). MS (ESI) Calcd. for C$_{11}$H$_9$BrN$_2$OS [M+H]$^+$ 296, Found 296.

Step 4: Preparation of N-(7-(1H-pyrazole-4-yl)benzo[d]thiazole-2-yl) cyclopropanecarboxamide (5)

To N-(7-bromobenzo[d]thiazole-2-yl) cyclopropanecarboxamide (480 mg, 1.6 mmol) and 1H-pyrazole-4-boronic acid pinacol ester (317 mg, 1.6 mmol) in dioxane (15 mL) was added Pd(dppf)Cl2 (119 mg, 162 umol), K$_2$CO$_3$ (672 mg, 4.9 mmol) and H$_2$O (2.5 mL) under the protection of nitrogen. The mixture was stirred at 90° C. for reacting for 12 hours. TLC (PE:EA=1:1) detected and showed a new point. LC-MS detected the target product. The reaction mixture was diluted with water (100 mL) and then extracted with ethyl acetate (30 mL×3). The organic phase was combined, washed with saturated salt water (5 mL), dried with anhydrous sodium sulfate, and filtered and spun dry. The residue was purified through column chromatography (PE:EA=1:1) to give N-(7-(1H-pyrazole-4-yl)benzo[d]thiazole-2-yl) cyclopropane carboxamide (80 mg, 15.63% yield) as a yellow solid. $^1$H NMR (400 MHz, DMSO-d$_6$) δ=13.22 (br. s., 1H), 12.70 (s, 1H), 8.23 (s, 1H), 7.99 (s, 1H), 7.64 (d, J=8.03 Hz, 1H), 7.52-7.55 (m, 1H), 7.45-7.50 (m, 1H), 2.03 (t, J=4.52 Hz, 1H), 0.95-1.00 (m, 4H). MS (ESI) Calcd. for C$_{14}$H$_{12}$N$_4$OS [M+H]$^+$ 285, Found 285.

Step 5: Preparation of 7-(1H-pyrazole-4-yl)benzo[d]thiazole-2-amine (6)

To a solution of N-(7-(1H-pyrazole-4-yl)benzo[d]thiazole-2-yl)cyclopropyl carboxamide (120 mg, 422.1 ummol) in methanol (3 mL) was added dropwise NaOH (240 mg, 6 mmol) in an aqueous solution (1 mL). The mixture was stirred at 80° C. for reacting for 12 hours. LCMS detected and showed that the reaction was completed. The reaction mixture was diluted with water (50 mL), neutralized with 1M of HCl to pH=7, and extracted with ethyl acetate (15 mL×4). The organic phase was combined, washed with saturated salt water (5 mL), dried with anhydrous sodium sulfate, and filtered and spun dry to give the residue of 7-(1H-pyrazole-4-yl)benzo[d] thiazole-2-amine (100 mg, 87.7% yield) as a crude product which was directly used in the next step without further purification. MS (ESI) Calcd. for C$_{10}$H$_8$N$_4$S [M+H]$^+$ 216, Found 216.8.

Step 6: Preparation of tert-butyl 3-(4-(2-aminobenzo[d]thiazole-7-yl)-1H-pyrazole-1-yl)-3-(cyanomethyl)azetidine-1-carbonate (7)

To a solution of 7-(1H-pyrazole-4-yl)benzo[d]thiazole-2-amine (100 mg, 462.4 umol) and tert-butyl 3-(cyanomethyl) azetidine-1-carbonate (90 mg, 463.4 umol) in acetonitrile (3 mL) was added dropwise DBU (140.8 mg, 924.8 umol) under the protection of nitrogen. The mixture was stirred at 30° C. for reacting for 12 hours. LC-MS detected and showed that the reaction was completed. The reaction mixture was diluted with water (50 mL) and extracted with ethyl acetate (20 mL×3). The organic phase was combined, washed with saturated salt water (30 mL), dried with anhydrous sodium sulfate, and filtered and spun dry to give the residue of tert-butyl 3-(4-(2-aminobenzo[d]thiazole-7-yl)-1H-pyrazole-1-yl)-3-(cyanomethyl)azetidine-1-carbonate (190 mg, 80% yield) as a crude product which was directly used in the next step without further purification. MS (ESI) Calcd. for C$_{20}$H$_{22}$N$_6$O$_2$S[M+H]$^+$ 410, Found 411.

Step 7: Preparation of 2-(3-(4-(2-aminobenzo[d]thiazole-7-yl)-1H-pyrazole-1-yl)-azetidine-3-yl) methyl cyanide(8)

Tht mixture of tert-butyl 3-(4-(2-aminobenzo[d]thiazole-7-yl)-1H-pyrazole-1-yl)-3-(cyanomethyl) azetidine-1-carbonate (180 mg, 438.5 umol) and hydrochloride ethyl acetate (30 mL) was stirred at 25° C. for reacting for 1 hour. LCMS detected that the reaction was completed. The reaction mixture was spun dry directly to give a yellow solid of 2-(3-(4-(2-aminobenzo[d]thiazole-7-yl)-1H-pyrazole-1-yl)-azetidine-3-yl) methyl cyanide (150 mg, 78.9% yield, HCl salt) as a crude product which was directly used in the next step without further purification. MS (ESI) Calcd. for C$_{15}$H$_{14}$N$_6$S [M+H]$^+$ 310, Found 310.

Step 8: Preparation of 2-(3-(4-(2-aminobenzo[d]thiazole-7-yl)-1H-pyrazole-1-yl)-(methyl sulfonyl) azetidine-3-yl) methyl cyanide(WX27)

To 2-(3-(4-(2-aminobenzo[d]thiazole-7-yl)-1H-pyrazole-1-yl)-azetidine-3-yl) methyl cyanide (150 mg, 345.9 umol, HCl salt) and Et₃N (140 mg, 1.4 mmol) in dichloromethane (3 mL) was added dropwise MsCl (80 mg, 698.9 umol) at 0° C. under the protection of nitrogen. The mixture was stirred at 0° C. for reacting for 1 hour. LC-MS detected that the reaction was completed. The reaction mixture was quenched with water (50 mL) and extracted with dichloromethane (15 mL×3). The organic phase was combined, washed with saturated salt water (5 mL), dried with anhydrous sodium sulfate, and filtered and spun dry. The residue was purified through preparative thin layer chromatography (DMC:MeOH=10:1) to give 2-(3-(4-(2-aminobenzo[d]thiazole-7-yl)-1H-pyrazole-1-yl)-(methylsulfonyl)azetidine-3-yl) methyl cyanide (30 mg, 20.1% yield) as a yellow solid. ¹H NMR (400 MHz, DMSO-d₆) δ=8.55 (s, 1H), 8.07 (s, 1H), 7.56 (s, 2H), 7.28-7.31 (m, 2H), 7.25-7.28 (m, 1H), 4.54 (d, J=9.29 Hz, 2H), 4.27 (d, J=9.29 Hz, 2H), 3.66 (s, 2H), 3.14 (s, 3H). MS (ESI) Calcd. for $C_{16}H_{16}N_6O_2S_2[M+H]^+$ 389, Found 389.

Example 23

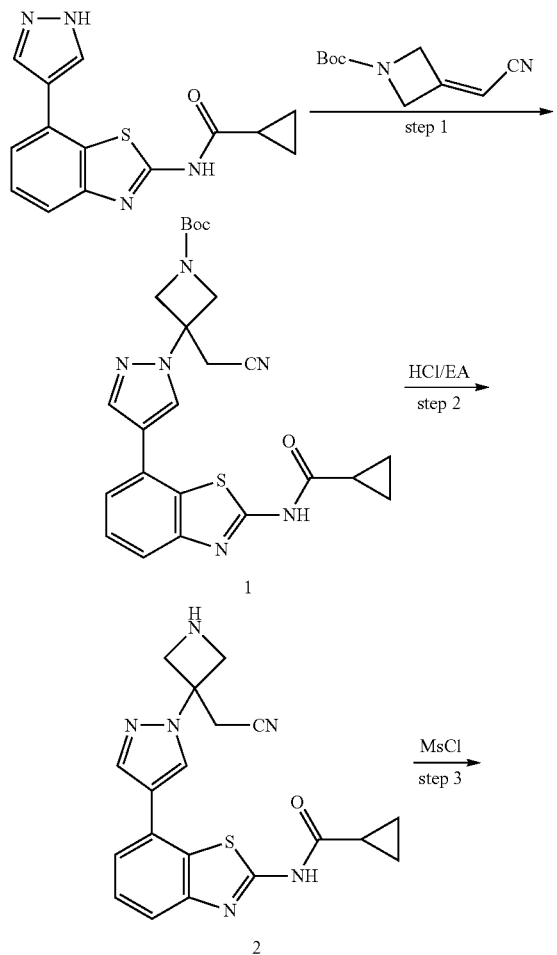

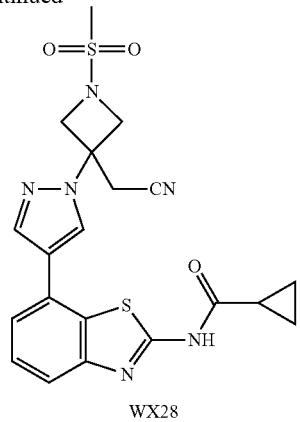

WX28

Step 1: Preparation of tert-butyl 3-(cyanomethyl)-3-(4-(2-(cyclopropanecarboxamido) benzo[d]thiazole-7-yl)-1H-pyrazole-1-yl) azetidin-1-carbonate To N-[7-(1H-pyrazole-4-yl)-1,3-benzothiazol-2-yl] cyclopropanecarboxamide (100 mg, 351.7 umol) and tert-butyl 3-(cyanomethylene) azetidin-carbonate (100 mg, 513.5 umol) in acetonitrile (3 mL) was added dropwise DBU (107 mg, 703.4 umol) under the protection of nitrogen. The mixture was stirred at 25° C. for reacting for 12 hours. TLC (PE:EA=1:1) detected and showed that the reaction was completed. The reaction mixture was diluted with water (50 mL) and extracted with ethyl acetate (20 mL×3). The organic phase was combined, washed with saturated salt water (5 mL), dried with anhydrous sodium sulfate, and filtered and spun dry. The residue was separated and purified through preparative TLC (PE:EA=1:1) to give tert-butyl 3-(cyanomethyl)-3-(4-(2-(cyclopropanecarboxamido)benzo[d]thiazole-7-yl)-1H-pyrazole-1-yl) azetidin-1-carbonate (80 mg, 47.5% yield) as a yellow solid. ¹H NMR (400 MHz, CDCl₃) δ=11.30 (br. s., 1H), 8.05 (d, J=12.05 Hz, 2H), 7.75 (d, J=7.78 Hz, 1H), 7.48-7.53 (m, 1H), 7.43-7.47 (m, 1H), 4.58 (d, J=9.79 Hz, 2H), 4.32 (d, J=9.54 Hz, 2H), 3.31 (s, 2H), 1.74 (dq, J=7.97, 3.95 Hz, 1H), 1.51 (s, 9H), 1.27-1.31 (m, 2H), 1.01-1.09 (m, 2H). MS (ESI) Calcd. for $C_{24}H_{26}N_6O_3S$ $[M+H]^+$ 479, Found 479.

Step 2: Preparation of N-(7-(1-(3-(cyanomethyl) azetidin-3-yl)-1H-pyrazole-4-yl) benzo[d]thiazole-2-yl) cyclopropanecarboxamide Tht mixture of tert-butyl 3-(cyanomethyl)-3-(4-(2-(cyclopropanecarboxamido) benzo[d]thiazole-7-yl)-1H-pyrazole-1-yl) azetidin-1-carbonate (80 mg, 167.2 umol) and hydrochloride ethyl acetate (30 mL) was stirred at 25° C. for reacting for 1 hour. LCMS detected that the reaction was completed. The reaction mixture was spun dry directly. The residue was dissolved in water (50 mL), adjusted with the aqueous solution of saturated NaHCO₃ to weakly alkaline (pH>7), and then extracted with ethyl acetate (15 mL×3). The organic phase was combined, washed with saturated salt water (5 mL), dried with anhydrous sodium sulfate, and filtered and spun dry to give a yellow solid of N-(7-(1-(3-(cyanomethyl)azetidin-3-yl)-1H-pyrazole-4-yl) benzo[d]thiazole-2-yl) cyclopropanecarboxamide (60 mg, 85.4% yield, purity of 90%) as a crude product which was directly used in the next step without further purification. MS (ESI) Calcd. for $C_{19}H_{18}N_6OS[M+H]^+$ 37, Found 378.

Step 3: Preparation of N-(7-(1-(3-(cyanomethyl)-1-(methylsulfonyl)azetidin-3-yl)-1H-pyrazole-4-yl)benzo[d]thiazole-2-yl) cyclopropanecarboxamide To a solution of N-(7-(1-(3-(cyanomethyl)azetidin-3-yl)-1H-pyrazole-4-yl) benzo[d]thiazole-2-yl) cyclopropanecarboxamide (60 mg, 158.54 umol) and triethylamine (50 mg, 494.6 umol) in dichloromethane (5 mL) was added dropwise methylsulfonyl chloride (50 mg, 436.5 umol). The mixture was stirred at 0° C. for 0.5 hour and stirred continuously at 25° C. for 1 hour. Both LC-MS and TLC detected and showed that the reaction was completed. The reaction mixture was quenched with water (50 mL) and extracted with ethyl acetate (15 mL×3). The organic phase was combined, washed with saturated salt water (5 mL), dried with anhydrous sodium sulfate, and filtered and spun dry. The residue was separated and purified through preparative TLC (PE:EA=1:1) to give N-(7-(1-(3-(cyanomethyl)-1-(methylsulfonyl)azetidin-3-yl)-1H-pyrazole-4-yl)benzo[d]thiazole-2-yl) cyclopropanecarboxamide (45 mg, 62% yield) as a white solid.

1H NMR (400 MHz, CDCl$_3$) δ=12.26 (br. s., 1H), 8.07 (s, 2H), 7.74 (d, J=7.78 Hz, 1H), 7.46-7.52 (m, 1H), 7.39-7.45 (m, 1H), 4.63 (d, J=9.03 Hz, 2H), 4.30 (d, J=9.03 Hz, 2H), 3.41 (s, 2H), 3.04 (s, 3H), 1.72-1.80 (m, 1H), 1.26 (d, J=3.26 Hz, 2H), 1.01 (dd, J=7.40, 2.89 Hz, 2H). MS (ESI) Calcd. for C$_{20}$H$_{20}$N$_6$O$_3$S$_2$[M+H]$^+$ 457, Found 457.

Example 24

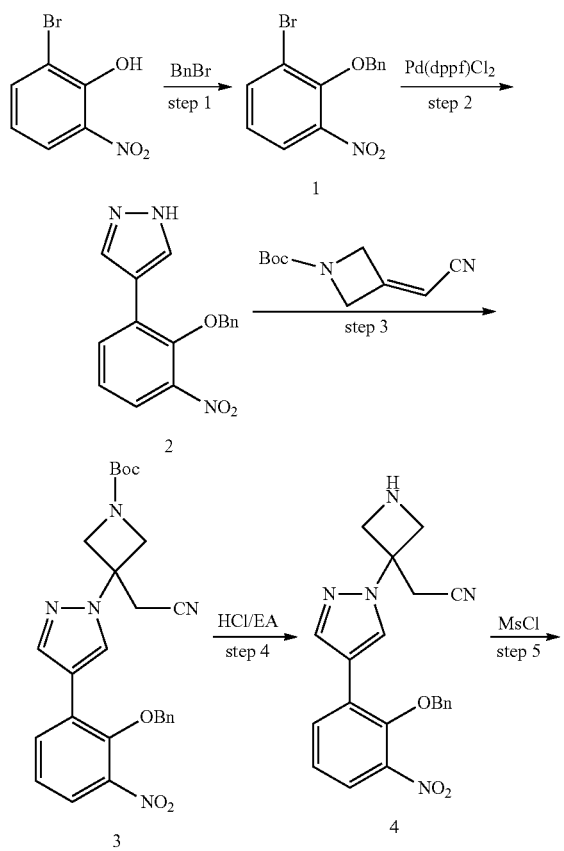

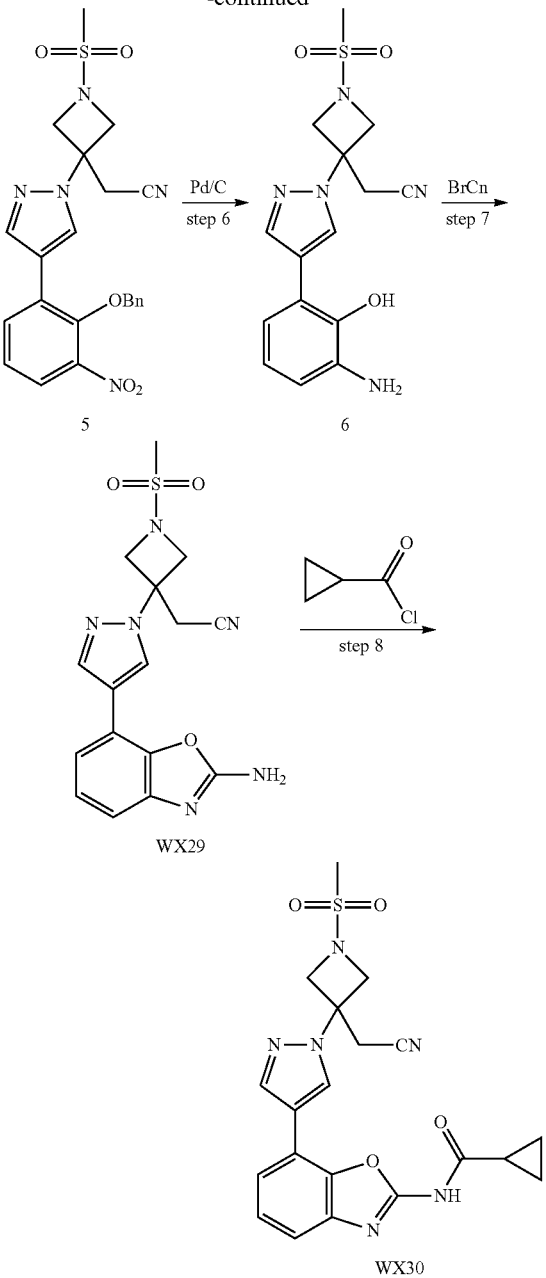

Step 1: Preparation of 2-(benzyloxy)-1-bromo-3-nitrobenzene

To 2-bromo-6-nitrophenol (5.2 g, 23.9 mmol) and K$_2$CO$_3$ (3.6 g, 26.3 mmol) in acetonitrile (100 mL) was benzyl bromide (4.3 g, 25.3 mmol). The mixture was stirred at 100° C. for 3 hour. TLC (PE:EA=10:1) detected and showed that the reaction was completed. The reaction mixture was filtered and the solid was eluted with ethyl acetate (10 mL×3). After the filtrate was spun dry, the residue was dissolved in ethyl acetate, and washed with water (20 m/L) and saturated salt water (20 mL). The organic phase was dried with anhydrous sodium sulfate, filtered and spun dry to give a yellow solid of 2-(benzyloxy)-1-bromo-3-nitrobenzene (7.50 g, 91.51% yield) as a crude product which was directly used in the next step without further purification. $^1$H NMR (400 MHz, CDCL$_3$) □7.84 (d, J=8.03 Hz, 1H), 7.79 (d, J=8.03 Hz, 1H), 7.56 (d, J=6.53 Hz, 2H), 7.37-7.45 (m, 3H), 7.16 (t, J=8.28 Hz, 1H), 5.21 (s, 2H). MS (ESI) Calcd. for C$_{13}$H$_{10}$BrNO$_3$ [M+H]$^+$ 308, Found 308.

Step 2: Preparation of 4-(2-(benzyloxy)-3-nitrophenyl)-1H-pyrazole

To 2-(benzyloxy)-1-bromo-3-nitrobenzene (1.0 g, 3.3 mmol) and ter-butyl 1H-pyrazole-4-boronic acid pinacol ester-1-carbonate (1.0 g, 3.4 mmol) in dioxane (30 mL) was added Pd(dppf)Cl$_2$ (250 mg, 341.7 umol), K$_2$CO$_3$ (1.4 g, 9.8 mmol) and H$_2$O (2.5 mL) under the protection of nitrogen. The mixture was stirred at 100° C. for reacting for 12 hours. Both TLC (PE:EA=1:1) and LC-MS detected and showed that the reaction was completed. The reaction mixture was diluted with water (20 mL), and extracted with ethyl acetate (20 mL×3). The organic phase was combined, washed with saturated salt water (5 mL), dried with anhydrous sodium sulfate, and filtered and spun dry. The residue was separated and purified through column chromatography (PE:EA=1:1) to give 4-(2-(benzyloxy)-3-nitrophenyl)-1H-pyrazole (900 mg, 89.1% yield) as a yellow oil product. $^1$H NMR (400 MHz, CDCl$_3$) δ=8.03 (s, 2H), 7.70-7.78 (m, 2H), 7.33-7.39 (m, 5H), 7.28-7.32 (m, 1H), 4.87 (s, 2H). MS (ESI) Calcd. for C$_{16}$H$_{13}$N$_3$O$_3$ [M+H]$^+$ 296, Found 296.

Step 3: Preparation of ter-butyl 3-(4-(2-(benzyloxy)-3-nitrophenyl)-1H-pyrazole-1-yl)-3-(cyanomethyl) azetidin-1-carbonate To 4-(2-(benzyloxy)-3-nitrophenyl)-1H-pyrazole (900 mg, 3.1 mmol) and ter-butyl 3-(cyanomethylene) azetidin-1-carbonate (900 mg, 4.6 mmol) in acetonitrile (20 mL) was added dropwise DBU (928 mg, 6.1 mmol) at 0° C. under the protection of nitrogen. The mixture was stirred at 25° C. for reacting for 3 hours. TLC (PE:EA=1:1) detected and showed that the reaction was completed. The reaction mixture was quenched with water (60 mL) and extracted with ethyl acetate (20 mL×3). The organic phase was combined, washed with saturated salt water (5 mL), dried with anhydrous sodium sulfate, and filtered and spun dry. The residue was separated and purified through column chromatography (PE:EA=1:1) to give ter-butyl 3-(4-(2-(benzyloxy)-3-nitrophenyl)-1H-pyrazole-1-yl)-3-(cyanomethyl) azetidin-1-carbonate (1.00 g, 60.3% yield) as a yellow oil product. $^1$H NMR (400 MHz, CDCl$_3$) δ=7.96 (d, J=9.03 Hz, 2H), 7.71-7.76 (m, 2H), 7.32-7.40 (m, 5H), 7.27-7.31 (m, 1H), 4.90 (s, 2H), 4.24 (d, J=9.54 Hz, 2H), 4.12 (d, J=9.03 Hz, 2H), 3.16 (s, 2H), 1.48 (s, 9H). MS (ESI) Calcd. for C$_{26}$H$_{27}$N$_5$O$_5$ [M+H]$^+$ 490, Found 490.

Step 4: Preparation of 2-(3-(4-2-(benzyloxy)-3-nitrophenyl-1H-pyrazole-1-yl) azetidin-3-yl)acetonitrile The mixture of 3-(4-(2-(benzyloxy)-3-nitrophenyl)-1H-pyrazole-1-yl)-3-(cyanomethyl)azetidin-1-carbonate (1.0 g, 2.04 mmol) and hydrochloride ethyl acetate (50 mL) was stirred at 25° C. for reacting for 3 hours. LC-MS detected and showed that the reaction was completed. After the reaction mixture was spun dry, the residue was dissolved in water (50 mL), adjusted with saturated NaHCO$_3$ solution to neutrality pH=7, and then extracted with ethyl acetate (15 mL×4). The organic phase was combined, washed with saturated salt water (2 mL), dried with anhydrous sodium sulfate, and filtered and spun dry to give a orange oil of 2-(3-(4-2-(benzyloxy)-3-nitrophenyl-1H-pyrazole-1-yl) azetidin-3-yl)acetonitrile (900 mg, 90.6% yield) as a crude product which can be directly used in the next step without further purification. MS (ESI) Calcd. for C$_{21}$H$_{19}$N$_5$O$_3$ [M+H]$^+$ 390, Found 390.

Step 5: Preparation of 2-(3-(4-2-(benzyloxy)-3-nitrophenyl-1H-pyrazole-1-yl)-1-(methylsulfonyl)azetidin-3-yl)acetonitrile To 2-(3-(4-2-(benzyloxy)-3-nitrophenyl-1H-pyrazole-1-yl) azetidin-3-yl)acetonitrile (900 mg, 2.3 mmol) and triethylamine (730 mg, 7.2 mmol) in dichloromethane (10 mL) was added dropwise methanesulfonyl chloride (529 mg, 4.6 mmol) at 0° C. under the protection of nitrogen. The mixture was stirred at 0° C. for reacting for 1 hour. LC-MS detected and showed that the reaction was completed. The reaction mixture was quenched with water (50 mL) and then extracted with ethyl acetate (20 mL×3). The organic phase was combined, washed with saturated salt water (5 mL), dried with anhydrous sodium sulfate, and filtered and spun dry. The residue was separated and purified through column chromatography (PE:EA=1:1 (0.5% Et$_3$N)) to give 2-(3-(4-2-(benzyloxy)-3-nitrophenyl-1H-pyrazole-1-yl)-1-(methylsulfonyl)azetidin-3-yl)acetonitrile (450 mg, 37.5% yield) as a yellow oil. $^1$H NMR (400 MHz, CDCl$_3$) δ=7.98 (d, J=12.55 Hz, 2H), 7.71-7.78 (m, 2H), 7.34-7.41 (m, 5H), 7.30 (t, J=8.03 Hz, 1H), 4.88-4.93 (m, 2H), 4.33 (d, J=9.03 Hz, 2H), 4.09 (d, J=9.54 Hz, 2H), 3.21 (s, 2H), 2.95 (s, 3H). MS (ESI) Calcd. for C$_{22}$H$_{21}$N$_5$O$_5$S [M+H]$^+$ 468, Found 468.

Step 6: Preparation of 2-(3-(4-(3-amino-2-hydroxypheyl)-1H-pyrazole-1-yl)-1-(methylsulfonyl)azetidin-3-yl)acetonitrile To 2-(3-(4-2-(benzyloxy)-3-nitrophenyl-1H-pyrazole-1-yl)-1-(methylsulfonyl) azetidin-3-yl)acetonitrile (400 mg, 855.6 umol) in ethyl acetate (10 mL) was added Pd/C (200 mg, 1.9 mmol) under the protection of nitrogen. The mixture was stirred at 25° C. for reacting for 1.5 hours. LC-MS detected and showed that the reaction was completed. The reaction mixture was filtered to remove Pd/C, and concentrated by rotary evaporation at low temperature to give 2-(3-(4-(3-amino-2-hydroxypheyl)-1H-pyrazole-1-yl)-1-(methylsulfonyl)azetidin-3-yl)acetonitrile (300 mg, 80.75%) as a pale yellow, which can be directly used in the next step without further purification. MS (ESI) Calcd. for C$_{15}$H$_{17}$N$_5$O$_3$S [M+H]$^+$ 348, Found 348.

Step 7: Preparation of 2-(3-(4-(2-aminobenzo[d]oxazole-7-yl)-1H-pyrazole-1-yl)-1-(methylsulfonyl)azetidin-3-yl)acetonitrile To 2-(3-(4-(3-amino-2-hydroxypheyl)-1H-pyrazole-1-yl)-1-(methyl sulfonyl)azetidin-3-yl)acetonitrile (300 mg, 863.58 umol) in ethyl acetate (10 mL) solution was added cyanogen bromide (100 mg, 944.1 umol) under the protection of nitrogen. The mixture was stirred at 50° C. for reacting for 12 hours. LC-MS and TLC (DCM:MeOH=10:1) detected and showed that the reaction was completed. After the reaction mixture was directly spun dry, dissolved in DCM:MeOH=10:1 (3 mL), separated and purified through preparative TLC (DCM:MeOH=10:1) to give 2-(3-(4-(2-aminobenzo[d]oxazole-7-yl)-1H-pyrazole-1-yl)-1-(methylsulfonyl)azetidin-3-yl)acetonitrile (200 mg, 56.0% yield) as a yellow solid. $^1$H NMR (400 MHz, CDCl$_3$) δ=8.26 (br. s., 1H), 8.10 (s, 1H), 7.26-7.28 (m, 2H), 7.24 (d, J=7.28 Hz, 1H), 4.65 (d, J=9.03 Hz, 2H), 4.28 (d, J=9.29 Hz, 2H), 3.45 (s, 2H), 3.04 (s, 3H). MS (ESI) Calcd. for $C_{16}H_{16}N_6O_3S$ $[M+H]^+$ 373, Found 373.

Step 8: Preparation of N-(7-(1-(3-(cyanomethyl)-1-(methylsulfonyl)azetidin-3-yl)-1H-pyrazole-4-yl) benzo[d]oxazole-2-yl) cyclopropanecarboxamide (WX30)

To 2-(3-(4-(2-aminobenzo[d]oxazole-7-yl)-1H-pyrazole-1-yl)-1-(methylsulfonyl) azetidin-3-yl)acetonitrile (100 mg, 268.5 umol) and triethylamine (54 mg, 537.1 umol) in acetonitrile (3 mL) was added dropwise cyclopropanecarboxylic acid chloride (30 mg, 287.3 umol) under the protection of nitrogen. The mixture was stirred at 30° C. for reacting for 12 hours. Low yield for the reaction was detected and showed from LCMS. The reaction mixture was directly spun dry, and the residue was separated and purified through preparative TLC (DCM:MeOH=10:1) to give N-(7-(1-(3-(cyanomethyl)-1-(methyl sulfonyl)azetidin-3-yl)-1H-pyrazole-4-yl)benzo[d]oxazole-2-yl) cyclopropanecarboxamide (10 mg, 8.45% yield) as a yellow solid. $^1$H NMR (400 MHz, DMSO-d$_6$) δ=12.05 (br. s., 1H), 8.77 (s, 1H), 8.34 (s, 1H), 7.60 (d, J=7.53 Hz, 1H), 7.44 (d, J=7.53 Hz, 1H), 7.31-7.38 (m, 1H), 4.52 (d, J=9.29 Hz, 2H), 4.30 (d, J=9.03 Hz, 2H), 3.66 (s, 2H), 3.15 (s, 3H), 2.14 (br. s., 1H), 0.96 (d, J=5.52 Hz, 4H). MS (ESI) Calcd. for $C_{20}H_{20}N_6O_4S$ $[M+H]^+$ 441, Found 441.

Example 25

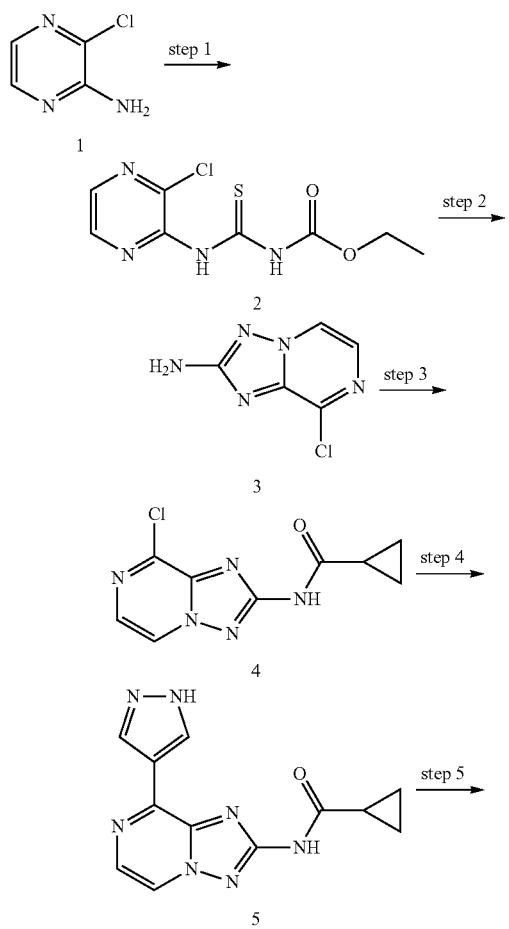

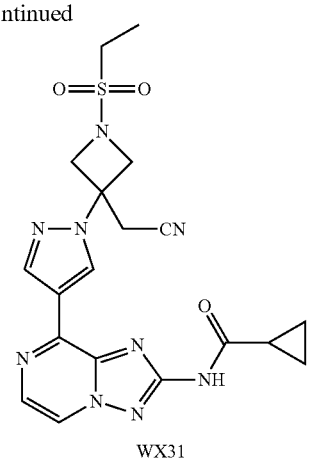

WX31

Step 1: Preparation of ethyl N-[(3-chloropyrazin 2-yl)thiocarbamoyl]carbamate

To 3-chloropyrazin-2-amine (8.7 g, 67.2 mmol) dissolved in THF (100 mL) was added ethyl isothiocyanate (9.7 g, 73.9 mmol). The resulting mixture was stirred at 27° C. for reacting for 48 hours until LC-MS showed complete reaction. The reaction mixture solvent THF was spun dry under reduced pressure to give a crude product of ethyl N-[(3-chloropyrazin-2-yl)thiocarbamoyl] carbamate which was washed with tert-butyl methyl ether, dried, and directly used in the next step without further purification (purity enough). MS (ESI) Calcd. for $C_8H_9ClN_4O_2S$ $[M+H]^+$ 261, Found 261.

Step 2: Preparation of 8-chloro-[1,2,4]triazolo[1,5-a]pyrazine-2-amine

Hydroxylamine hydrochloride (20.0 g, 287.7 mmol) was suspended in 100 mL of mixture of ethanol and methanol (1:1), and then DIEA (22.3 g, 172.6 mmol) was added. After the resulting mixture was stirred at 27° C. for reacting for 1 hour, ethyl N-[(3-chloropyrazin-2-yl)thiocarbamoyl]carbamate (15.0 g, 57.54 mmol) was added to this system and refluxed (70° C.) slowly for 3 hours. After LC-MS showed that the reaction was completed, the reaction mixture was cooled to room temperature, filtered, washed with water and MTBE, and then dried under vacuum (60° C.) to give 8-chloro-[1,2,4]triazolo[1,5-a]pyrazine-2-amine (6.50 g, 64.62% yield) as a yellow solid. MS (ESI) Calcd. for $C_8H_4ClN_5$ $[M+H]^+$ 170, Found 170.

Step 3: Preparation of N-(8-chloro-[1,2,4]triazolo[1, 5-a]pyrazine-2-yl) cyclopropanecarboxamide To 8-chloro-[1,2,4]triazolo[1,5-a]pyrazine-2-amine (2.0 g, 11.8 mmol) dissolved in anhydrous $CH_3CN$ (30 mL) was added $Et_3N$ (3 g, 29.5 mmol) at 5° C., followed by the addition of cyclopropanecarboxylic acid chloride (3.1 g, 29.5 mmol). After adding, the reaction mixture was warmed to 28° C. and stirred until LC-MS showed that all raw materials are consumed. If needed, $Et_3N$ (7.1 mmol) and cyclopropanecarboxylic acid chloride (7.1 mmol) were further added to ensure complete reaction. The solvent was spun dry under reduced pressure to give the residue. The residue was beat with $Et_2O$ (50 mL), the solid was collected by filtration, washed with $H_2O$ (2×50 mL), acetone (50 mL)

and Et₂O (50 mL), and then dried under vacuum to give N-(8-chloro-[1,2,4]triazolo[1,5-a]pyrazine-2-yl) cyclopropanecarboxamide (1.2 g) as a yellow solid. MS (ESI) Calcd. for $C_9H_8ClN_5O$ [M+H]⁺ 237, Found 237.

Step 4: Preparation of N-[8-(1H-pyrazole-4-yl)-[1,2,4]triazolo[1,5-a]pyrazine-2-yl]cyclopropanecarboxamide To N-(8-chloro-[1,2,4]triazolo[1,5-a]pyrazine-2-yl) cyclopropanecarboxamide (100 mg, 420.8 umol), 4-(4,4,5,5-tetramethyl-1,3,2-dioxaborolan-2-yl)-1H-pyrazole (122.5 mg, 631.2 umol) and K2CO3 (175 mg, 1.3 mmol), dissolved in the mixture solvent of H₂O (1 mL)/dioxane (4 mL), was added Pd(dppf)Cl₂.CH₂Cl₂ (34 mg, 42.08 umol). After vacuuming and filling with nitrogen, the mixture was stirred at 100° C. for reacting for 3 hours. After LC-MS showed that the reaction was completed, the mixture was cooled to room temperature. The mixture was filtered through diatomite bed and the diatomite was washed with DCM (30 mL). The organic layer was separated and the water layer was extracted with DCM (3×50 mL). The organic phase was combined, washed with saturated salt water, dried with anhydrous Na₂SO₄. The solvent was spun dry under reduced pressure, and the crude product was purified through thin layer chromatography (DCM/MeoH=10:1) to give N-[8-(1H-pyrazole-4-yl)-[1,2,4]triazolo[1,5-a]pyrazine-2-yl] cyclopropanecarboxamide (70 mg, 8.1% yield) as a pale yellow solid. MS ((ESI)) Calcd. for $C_{12}H_{11}N_7O$ [M+H]⁺ 270, Found 270.

Step 5: Preparation of N-[8-[1-[3-(cyanomethyl)-1-ethylsulfonylazetidin-3-yl]pyrazole-4-yl)-[1,2,4]triazolo[1,5-a]pyrazine-2-yl] cyclopropanecarboxamide(WX31)

To N-[8-(1H-pyrazole-4-yl)-[1,2,4]triazolo[1,5-a]pyrazine-2-yl] cyclopropanecarboxamide (120 mg, 445.7 umol) and 2-(1-ethylsulfonylazetidin-3-ylidene) acetonitrile (125 mg, 668.5 umol) dissolved in DMF (10 mL), was added DBU (136 mg, 891 umol). The resulting mixture was stirred at 40° C. for reacting for 16 hours. After LC-MS showed that the reaction was completed, the solvent was spun dry under reduced pressure, and the residue was dissolved in EtOAc (50 mL). The resulting solution was washed with 1N of HCl (10 mL) and saline water (20 mL), the organic phase was dried with anhydrous Na₂SO₄ and the solvent was spun dry. The residue was purified through preparative thin layer chromatography (PE/EA=1:4) to give a crude compound, which was purified and freeze-dried through preparative HPLC (HCl) to give N-[8-[1-[3-(cyanomethyl)-1-ethylsulfonylazetidin-3-yl]pyrazole-4-yl)-[1,2,4]triazolo[1,5-a]pyrazine-2-yl] cyclopropanecarboxamide (40 mg) as a white solid. ¹H-NMR (400 MHz, MeOD-d₄) δ=8.07 (d, J=8 Hz, 2H), 7.86 (dd, J=7.2, 13.2 Hz, 2H), 7.67 (d, J=8.4 Hz, 2H), 7.44-7.42 (m, 1H), 4.19 (s, 2H), 3.44 (d, J=4.8 Hz, 4H), 3.26 (d, J=4.8 Hz, 4H), 2.95 (m, 1H), 0.87 (m, 2H), 0.74 (m, 2H). MS (ESI) Calcd. for $C_{19}H_{21}N_9O_3S$ [M+H]⁺ 456, Found 456.

Example 26

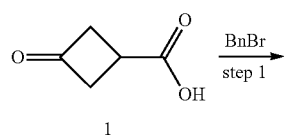

Step 1: Preparation of benzyl 3-oxocyclobutane-carboxylate

3-Oxocyclobutanecarboxylic acid (3.0 g, 26.3 mmol), benzyl bromide (6.7 g, 39.4 mmol) and potassium carbonate (7.3 g, 52.6 mmol) was dissolved in acetone (30 mL), and

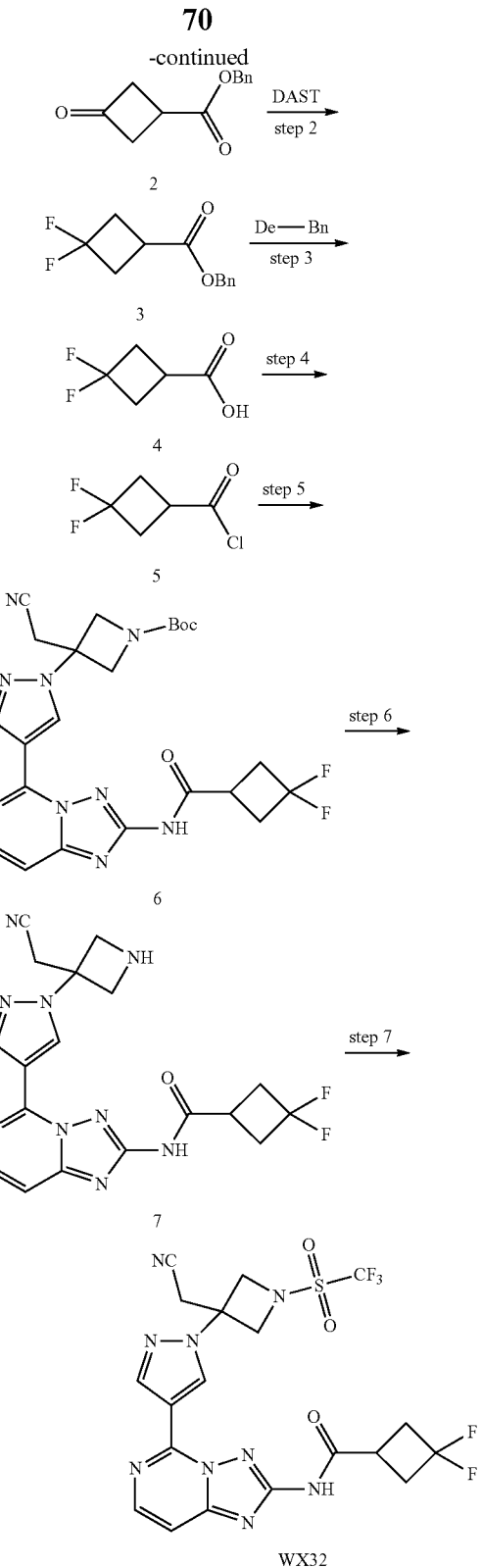

then heated to reflux for 10 hours. After TLC showed that the reaction was completed, the reaction mixture was concentrated under reduce pressure to remove the solvent, added water (20 mL), and extracted with ethyl acetate (150 mL×2). The combined organic phase was washed with saturated salt water (50 mL), dried with anhydrous sodium sulfate, filtered and concentrated under vacuum. The residue was purified through silica gel column chromatography (petroleum ether/ethyl acetate=10:1) to give benzyl 3-oxocyclobutane-carboxylate (2.5 g, 41.9% yield) as a colorless liquid. MS (ESI) Calcd. for $C_{12}H_{12}O_3$ [M+H]$^+$ 205, Found 205.

Step 2: Preparation of benzyl
3,3-difluorocyclobutane carboxylate

To benzyl 3-oxocyclobutane-carboxylate (1.0 g, 4.9 mmol) in dichloromethane (35 mL), was added dropwise DAST (1.6 g, 9.8 mmol) at −60° C. After adding, the reaction mixture was warmed slowly to 15° C. and stirred for 10 hours. After TLC showed that the reaction was completed, the reaction mixture was cooled to 0° C. Saturated sodium bicarbonate solution (10 mL) for quenching reaction, the water phase was extracted with dichloromethane (30 mL×2). The organic phase was combined, washed with saturated salt water (10 mL), dried with anhydrous sodium sulfate, filtered and concentrated under vacuum. The residue was purified through silica gel column chromatography (petroleum ether/ethyl acetate=20:1~10:1) to give benzyl 3,3-difluorocyclobutane carboxylate (450 mg, 36.54% yield) as a colorless oil. MS (ESI) Calcd. for $C_{12}H_{12}F_2O_2$ [M+H]$^+$ 227, Found 227.

Step 3: Preparation of 3,3-difluorocyclobutane
carboxylic acid

To solution of benzyl 3,3-difluorocyclobutane carboxylate (450 mg, 2.0 mmol) dissolved in ethanol (10 mL), was added Pd/C (10%, 40 mg). The reaction mixture was stirred at room temperature for 10 hours under the atmosphere of hydrogen (15 psi). After TLC showed that the reaction was completed, the solid was filtered out, the filtrate was concentrated under vacuum to give 3,3-difluorocyclobutane carboxylic acid (250 mg, 83.1% yield) as a white solid. MS (ESI) Calcd. for $C_5H_6F_2O_2$[M+H]$^+$ 137, Found 137.

Step 4: Preparation of 3,3-difluorocyclobutane
carbonyl chloride

To a solution of 3,3-difluorocyclobutane carboxylic acid (230 mg, 1.69 mmol) and DMF (13 mg, 169.0 umol) dissolved in dichloromethane (5 mL), was added dropwise oxalyl chloride (322 mg, 2.5 mmol) at 0° C. After adding, the reaction mixture was stirred at room temperature for 3 hours. After TLC showed that the reaction was completed, the reaction mixture was concentrated under vacuum to give 3,3-difluorocyclobutane carbonyl chloride (300 mg, a crude product) as a yellow solid. This product was directly used in the next step without further purification. MS (ESI) Calcd. for $C_5H_5ClF_2O$ [M+H]$^+$ 155, Found 155.

Step 5: Preparation of ter-butyl 3-(cyanomethyl)-3-
[4-[2-[(3,3-difluorocyclobutane carboxylic acid)
amino]-[1,2,4]triazolo[1,5-c]pyrimidin-5-ylpyrazole-
1-yl]azetidin-1-carboxylic acid To a solution of ter-butyl 3-[4-(2-amino-[1,2,4]triazolo[1,5-c]pyrimidin-5-yl) pyrazole-1-yl]-3-(cyanomethyl)-azetidin-1-carboxylic acid (395 mg, 1.0 mmol), DMAP (13 mg, 110 umol) and pyridine (396 mg, 5 mmol), dissolved in dichloromethane (8 mL), was added 3,3-difluorocyclobutane carbonyl chloride (294 mg, 1.9 mmol) at 0° C. The mixture was heated to 40° C. and stirred for 10 hours. The reaction was completed as shown from LCMS. The reaction mixture was poured into water (5 mL) and the water phase was extracted with dichloromethane (15 mL×2). The combined organic phase was washed with saturated salt water (10 mL), dried with anhydrous sodium sulfate, filtered and concentrated under vacuum. The residue was purified through preparative TLC (ethyl acetate/petroleum ether=1:0) to give ter-butyl 3-(cyanomethyl)-3-[4-[2-[(3,3-difluoro-cyclobutanecarboxylic acid)amino]-[1,2,4]triazolo[1,5-c]pyrimidin-5-ylpyrazole-1-yl] azetidin-1-carboxylic acid (80 mg, 12.00% yield) as a white solid. MS (ESI) Calcd. for $C_{23}H_{25}F_2N_9O_3$[M+H]$^+$ 514, Found 514.

Step 6: Preparation of N-[5-[1-[3-(cyanomethyl)
azetidin-3-yl]pyrazole-4-yl]-[1,2,4]triazolo[1,5-c]
pyrimidin-2-yl]-3,3-difluoro-cyclobutanecarboxam-
ide To a solution of ter-butyl 3-(cyanomethyl)-3-[4-[2-[(3,3-difluorocyclobutane carboxylic acid)amino]-[1,2,4]triazolo[1,5-c]pyrimidin-5-ylpyrazole-1-yl]azetidin-1-carboxylic acid (80 mg) dissolved in dichloromethane (5 mL) was added dropwise trifluoroacetic acid (765 mg, 6.7 mmol). The reaction mixture was stirred at room temperature for 2 hours. The reaction was completed as shown from LCMS. The reaction mixture was concentrated under vacuum to give N-[5-[1-[3-(cyanomethyl) azetidin-3-yl]pyrazole-4-yl]-[1,2,4]triazolo[1,5-c]pyrimidin-2-yl]-3,3-difluoro-cyclobutanecarboxamide (100 mg, crude product, TFA salt) as a brown solid. This product was directly used in the next step without purification. MS (ESI) Calcd. for $C_{18}H_{17}F_2N_9O$ [M+H]$^+$ 414, Found 414.

Step 7: Preparation of N-[5-[1-[3-(cyanomethyl)-1-
(trifluoromethylsulfonyl) azetidin-3-yl]pyrazole-4-
yl]-[1,2,4]triazolo[1,5-c]pyrimidin-2-yl]-3,3-dif-
luoro-cyclobutanecarboxamide(WX32)

To N-[5-[1-[3-(cyanomethyl)azetidin-3-yl]pyrazole-4-yl]-[1,2,4]triazolo[1,5-c]pyrimidin-2-yl]-3,3-difluoro-cyclobutanecarboxamide (100 mg, 189.61 umol, TFA salt) in dichloromethane (5 mL) was added trifluoromethanesulfonyl chloride (38 mg, 227.5 mmol), and then triethylamine (96 mg, 948.1 umol) was added. The reaction mixture was stirred at room temperature for 10 hours. The reaction was completed as shown from LCMS. The reaction mixture was concentrated under vacuum, and the residue was purified through preparative HPLC to give N-[5-[1-[3-(cyanomethyl)-1-(trifluoromethylsulfonyl)azetidin-3-yl]pyrazole-4-yl]-[1,2,4]triazolo [1,5-c]pyrimidin-2-yl]-3,3-difluoro-cyclobutanecarboxamide (3 mg, 2.9% yield) as a white solid. MS (ESI) Calcd. for $C_{19}H_{16}F_5N_9O_3S$ [M+H]$^+$ 546, Found 546.

Example 27

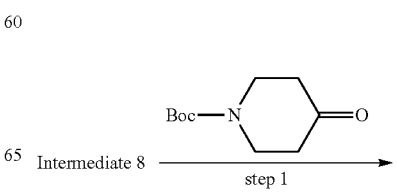

Intermediate 8 $\xrightarrow{\text{step 1}}$

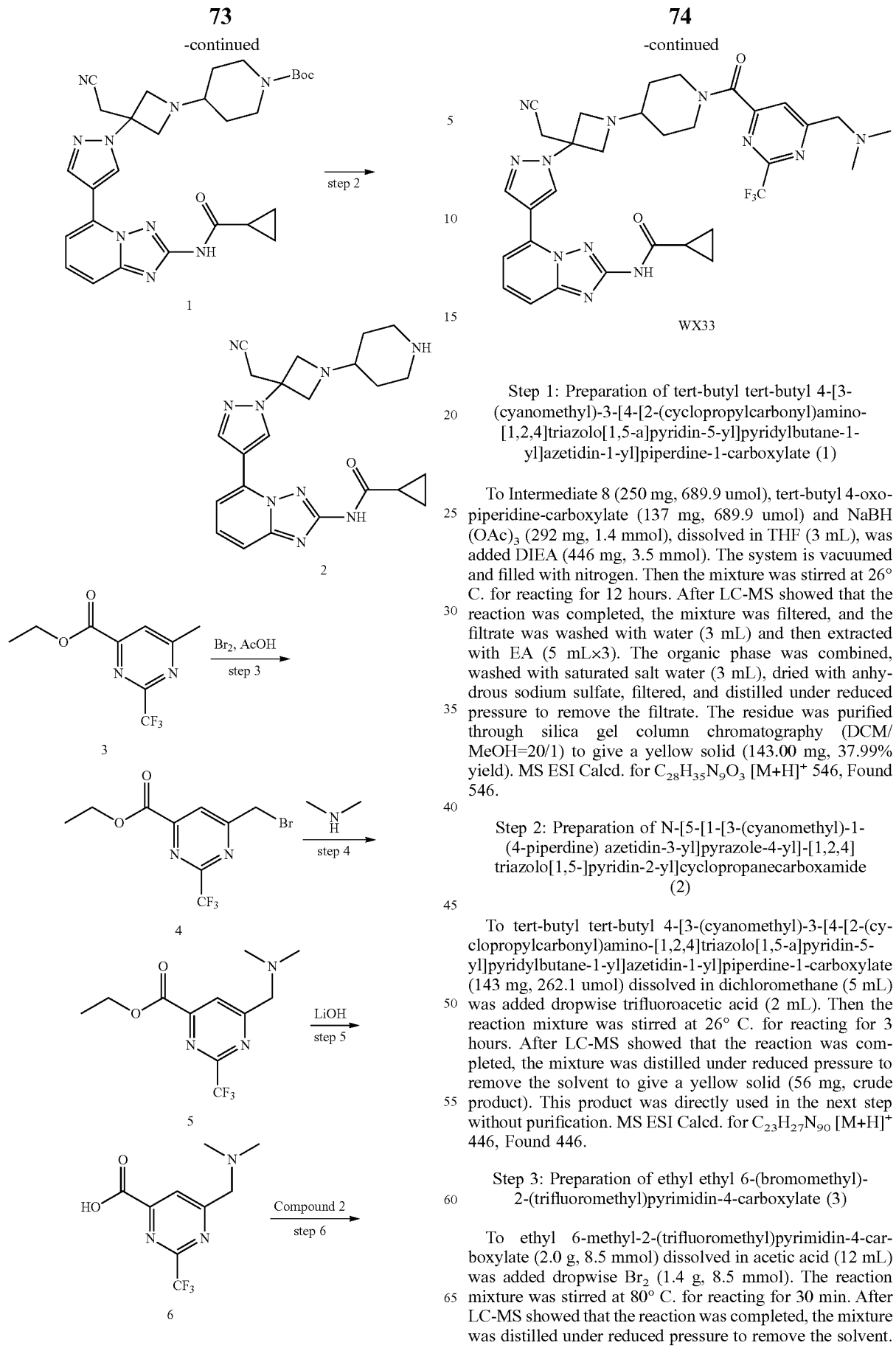

Step 1: Preparation of tert-butyl tert-butyl 4-[3-(cyanomethyl)-3-[4-[2-(cyclopropylcarbonyl)amino-[1,2,4]triazolo[1,5-a]pyridin-5-yl]pyridylbutane-1-yl]azetidin-1-yl]piperdine-1-carboxylate (1)

To Intermediate 8 (250 mg, 689.9 umol), tert-butyl 4-oxo-piperidine-carboxylate (137 mg, 689.9 umol) and NaBH(OAc)₃ (292 mg, 1.4 mmol), dissolved in THF (3 mL), was added DIEA (446 mg, 3.5 mmol). The system is vacuumed and filled with nitrogen. Then the mixture was stirred at 26° C. for reacting for 12 hours. After LC-MS showed that the reaction was completed, the mixture was filtered, and the filtrate was washed with water (3 mL) and then extracted with EA (5 mL×3). The organic phase was combined, washed with saturated salt water (3 mL), dried with anhydrous sodium sulfate, filtered, and distilled under reduced pressure to remove the filtrate. The residue was purified through silica gel column chromatography (DCM/MeOH=20/1) to give a yellow solid (143.00 mg, 37.99% yield). MS ESI Calcd. for $C_{28}H_{35}N_9O_3$ [M+H]⁺ 546, Found 546.

Step 2: Preparation of N-[5-[1-[3-(cyanomethyl)-1-(4-piperdine) azetidin-3-yl]pyrazole-4-yl]-[1,2,4]triazolo[1,5-]pyridin-2-yl]cyclopropanecarboxamide (2)

To tert-butyl tert-butyl 4-[3-(cyanomethyl)-3-[4-[2-(cyclopropylcarbonyl)amino-[1,2,4]triazolo[1,5-a]pyridin-5-yl]pyridylbutane-1-yl]azetidin-1-yl]piperdine-1-carboxylate (143 mg, 262.1 umol) dissolved in dichloromethane (5 mL) was added dropwise trifluoroacetic acid (2 mL). Then the reaction mixture was stirred at 26° C. for reacting for 3 hours. After LC-MS showed that the reaction was completed, the mixture was distilled under reduced pressure to remove the solvent to give a yellow solid (56 mg, crude product). This product was directly used in the next step without purification. MS ESI Calcd. for $C_{23}H_{27}N_9O$ [M+H]⁺ 446, Found 446.

Step 3: Preparation of ethyl ethyl 6-(bromomethyl)-2-(trifluoromethyl)pyrimidin-4-carboxylate (3)

To ethyl 6-methyl-2-(trifluoromethyl)pyrimidin-4-carboxylate (2.0 g, 8.5 mmol) dissolved in acetic acid (12 mL) was added dropwise Br₂ (1.4 g, 8.5 mmol). The reaction mixture was stirred at 80° C. for reacting for 30 min. After LC-MS showed that the reaction was completed, the mixture was distilled under reduced pressure to remove the solvent.

The residue was separated through preparation (PE/EA=3/1) to give a yellow oil liquid (610 mg, 12.3% yield). MS ESI Calcd. for $C_9H_8BrF_3N_2O_2$ [M+H]$^+$ 313, Found 313.

Step 4: Preparation of ethyl ethyl 6-[(dimethylamino)methyl]-2-(trifluoromethyl) pyrimidin-4-carboxylate (4)

To ethyl ethyl 6-(bromomethyl)-2-(trifluoromethyl)pyrimidin-4-carboxylate (610 mg, 2.0 mmol) and N-dimethylmethanamine (318 mg, 3.9 mmol), dissolved in dichloromethane (20 mL), was added dropwise triethylamine (592 mg, 5.9 mmol). The reaction mixture was stirred at 26° C. for 0.5 hour. After LC-MS showed that the reaction was completed, the filtrate was washed with water (20 mL) and then extracted with EA (20 mL×3). The organic phase was combined, washed with saturated salt water (20 mL), dried with anhydrous sodium sulfate, filtered, and distilled under reduced pressure to remove the filtrate. The residue was separated and purified through preparation (PE/EA=3/1) to give a yellow liquid (310 mg, 51.6% yield). MS ESI Calcd. for $C_{11}H_{14}F_3N_3O_2$[M+H]$^+$ 278, Found 278.

Step 5: Preparation of 6-[(dimethylamino)methyl]-2-(trifluoromethyl) pyrimidin-4-carboxylic acid (5)

To ethyl ethyl 6-[(dimethylamino)methyl]-2-(trifluoromethyl) pyrimidin-4-carboxylate (310 mg, 1.1 mmol) dissolved in tetrahydrofuran (8 mL) and water (2 mL) was added lithium hydroxide (54 mg, 2.3 mmol). The reaction mixture was stirred at 26° C. for 0.5 hour. After LC-MS showed that the reaction was completed, the mixture was distilled under reduced pressure to remove the solvent to give a yellow oil (314 mg) liquid which was directly used without purification. MS ESI Calcd. for $C_9H_{10}F_3N_3O_2$[M+H]$^+$ 250, Found 250.

Step 6: Preparation of N-(5-(1-(3-(cyanomethyl)-1-(1-(6-((dimethylamino)methyl)-2-(trifluoromethyl) pyrimidin-4-carbonyl)piperidine-4-yl)azetidin-3-yl)-1H-pyrazole-4-yl)-[1,2,4]triazolo[1,5-a] cyclopropanecarboxamide(WX33)

To a solution of N-[5-[1-[3-(cyanomethyl)-1-(4-piperidine)azetidin-3-yl]pyrazole-4-yl]-[1,2,4] triazolo[1,5-]pyridine-2-yl] cyclopropanecarboxamide (48 mg, 107.7 umol), the compound 2 (27 mg, 107.7 umol), EDCI (52 mg, 269.4 umol) and HOBt (36 mg, 269.4 umol), dissolved in DMF (3 mL), was added TEA (55 mg, 538.7 umol). The reaction mixture was stirred at 26° C. for reacting for 12 hours. After LC-MS showed that the reaction was completed, the reaction mixture was dissolved in EA (10 mL) and water (10 mL). The organic layer was separated and the water layer was extracted with EA (2×15 mL) twice. The organic phase was combined, washed with saturated salt water (5 mL), dried with anhydrous sodium sulfate, filtered, distilled under reduced pressure to remove the filtrate, separated through preparation to give a white solid (WX33) (5 mg, 6.9% yield). $^1$H NMR (400 MHz, METHANOL-d$_4$) δ=9.18 (s, 1H), 8.54 (s, 1H), 7.94 (s, 1H), 7.75-7.69 (m, 1H), 7.57 (ddd, J=1.1, 8.1, 18.9 Hz, 2H), 3.87-3.73 (m, 6H), 3.53 (s, 2H), 3.43-3.35 (m, 1H), 3.30-3.21 (m, 1H), 2.74-2.66 (m, 1H), 2.37 (s, 6H), 2.06-1.93 (m, 2H), 1.50 (d, J=10.3 Hz, 1H), 1.38-1.28 (m, 4H), 1.11-1.05 (m, 2H), 1.01-0.95 (m, 2H)。 MS ESI Calcd. for $C_{33}H_{35}F_3N_{12}O_2$ [M+H]$^+$ 677, Found 677.

Test for In Vitro Activity of Jak1, Jak2, and Jak3 Kinase
Experimental Materials
Recombinant human protease of JAK1, JAK2 and JAK3 were purchased from Life technology. LANCE Ultra ULight™-JAK-1 (Tyr1023) peptide and LANCE Eu-W1024 Anti-phosphotyrosine (PT66) were purchased from PerkinElmer. Multimode ELISA, Envison(PerkinElmer) reader was used.
Experimental Method
The test compound was diluted according to gradient of three times concentration with a final concentration of from 10 uM to 0.17 nM at 11 concentrations totally, each concentration with two complex holes, and the content of DMSO in the detection was 1%.
Enzyme Reaction of JAK1
2 nM of JAK1 Protein kinase, 50 nM of LANCE Ultra ULight™-JAK-1(Tyr1023) peptide, 38 uM of ATP, 50 mM of HEPES (pH 7.5), 10 mM of MgCl$_2$, 1 mM of EGTA, 2 mM of DTT, 0.01% BRIJ-35. Checker board is White Proxiplate 384-Plus plate (PerkinElmer). The reaction was carried out at room temperature for 90 min and the reaction system was 10 ul.
Enzyme Reaction of JAK2
0.02 nM of JAK2 Protein kinase, 50 nM of LANCE Ultra ULight™-JAK-1(Tyr1023) peptide, 12 uM of ATP, 50 mM of HEPES (pH 7.5), 10 mM of MgCl$_2$, 1 mM of EGTA, 2 mM of DTT, 0.01% BRIJ-35. Checker board is White Proxiplate 384-Plus plate (PerkinElmer). The reaction was carried out at room temperature for 60 min and the reaction system was 10 ul.
Enzyme Reaction of JAK3
0.05 nM of JAK3 Protein kinase, 50 nM of LANCE Ultra ULight™-JAK-1(Tyr1023) peptide, 4 uM of ATP, 50 mM of HEPES (pH 7.5), 10 mM of MgCl$_2$, 1 mM of EGTA, 2 mM of DTT, 0.01% BRIJ-35. Checker board is White Proxiplate 384-Plus plate (PerkinElmer). The reaction was carried out at room temperature for 90 min and the reaction system was 10 ul.
Determination for Reaction
10 ul detection reagent was added to reaction plate, wherein the final concentration of LANCE Eu-W1024 Anti-phosphotyrosine (PT66) was 2 nM, the final concentration of EDTA was 10 nM, incubated at room temperature for 60 min, with Envison reader.
Data Analysis
The reading was converted to inhibition ratio (%) by the following formula: the inhibition ratio (%)=(Min−Ratio)/(Max−Min)×100%. Four parameter curve fitting (Model 205 in XLFIT5, iDBS) measured IC50 data, as shown in Table 1.

TABLE 1

| Compound | JAK2 (nM) | JAK1/JAK2 (times) | JAK3/JAK2 (times) |
| --- | --- | --- | --- |
| Tofacitinib | 4 | 0.5 | 0.075 |
| WX00 | B | F1 | F4 |
| WX01 | B | F2 | F3 |
| WX02 | A | F1 | F3 |
| WX03 | B | F2 | F3 |
| WX04 | B | F1 | F3 |
| WX05 | B | F1 | F3 |
| WX06 | B | F1 | F3 |
| WX07 | B | F2 | F4 |
| WX08 | A | F1 | F4 |
| WX09 | A | F1 | F4 |
| WX10 | C | F1 | F1 |
| WX11 | C | F2 | F3 |
| WX12 | B | F2 | F3 |

TABLE 1-continued

| Compound | JAK2 (nM) | JAK1/JAK2 (times) | JAK3/JAK2 (times) |
|---|---|---|---|
| WX13 | A | F3 | F4 |
| WX14 | A | F2 | F4 |
| WX15 | A | F1 | F4 |
| WX16 | A | F1 | F3 |
| WX17 | B | F1 | F3 |
| WX18 | A | F1 | F3 |
| WX19 | B | F1 | F3 |
| WX20 | A | F1 | F4 |
| WX21 | A | F1 | F4 |
| WX22 | C | F1 | F3 |
| WX23 | C | F1 | F3 |
| WX24 | B | F3 | F4 |
| WX25 | C | F3 | F2 |
| WX26 | C | F3 | F3 |
| WX27 | A | F3 | F2 |
| WX28 | A | F3 | F4 |
| WX29 | A | F3 | F4 |
| WX30 | A | F2 | F4 |
| WX31 | C | F2 | F3 |
| WX32 | C | F2 | F3 |
| WX33 | B | F1 | F3 |

A ≤10 nM;
10 < B ≤ 100 nM;
100 < C ≤ 1000 nM;
1 ≤ F1 ≤ 5;
5 < F2 ≤ 10;
10 < F3 ≤ 25;
25 < F4 ≤ 100

Conclusion: The selectivity of the compounds of the present invention to JAK2 is superior to that of Tofacitinib.

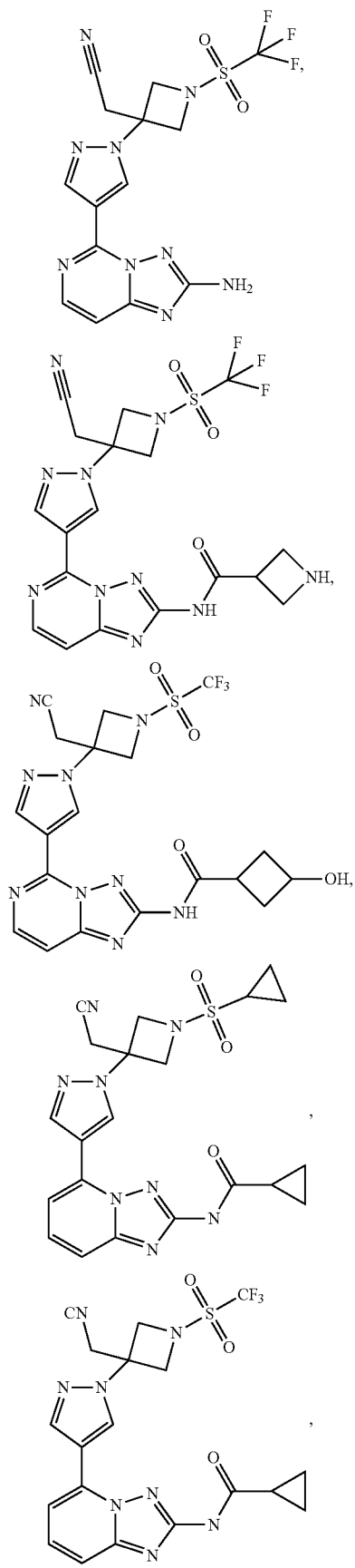
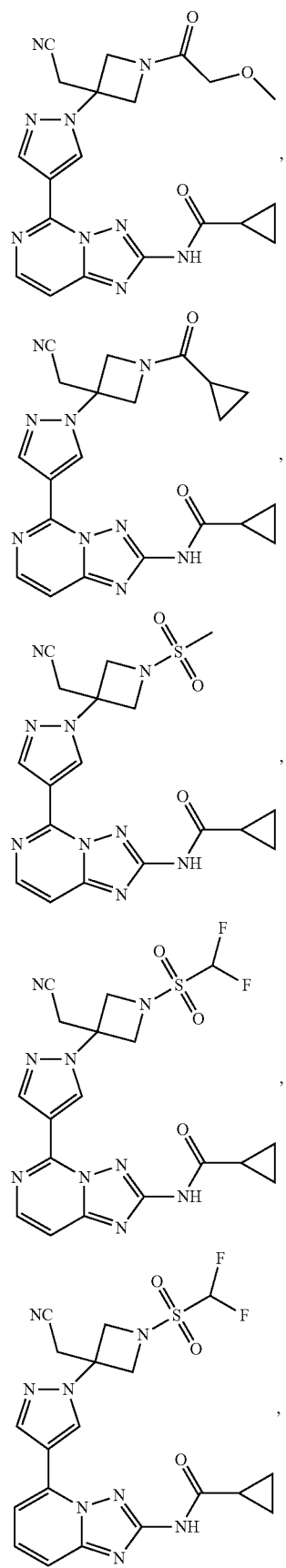

85
-continued
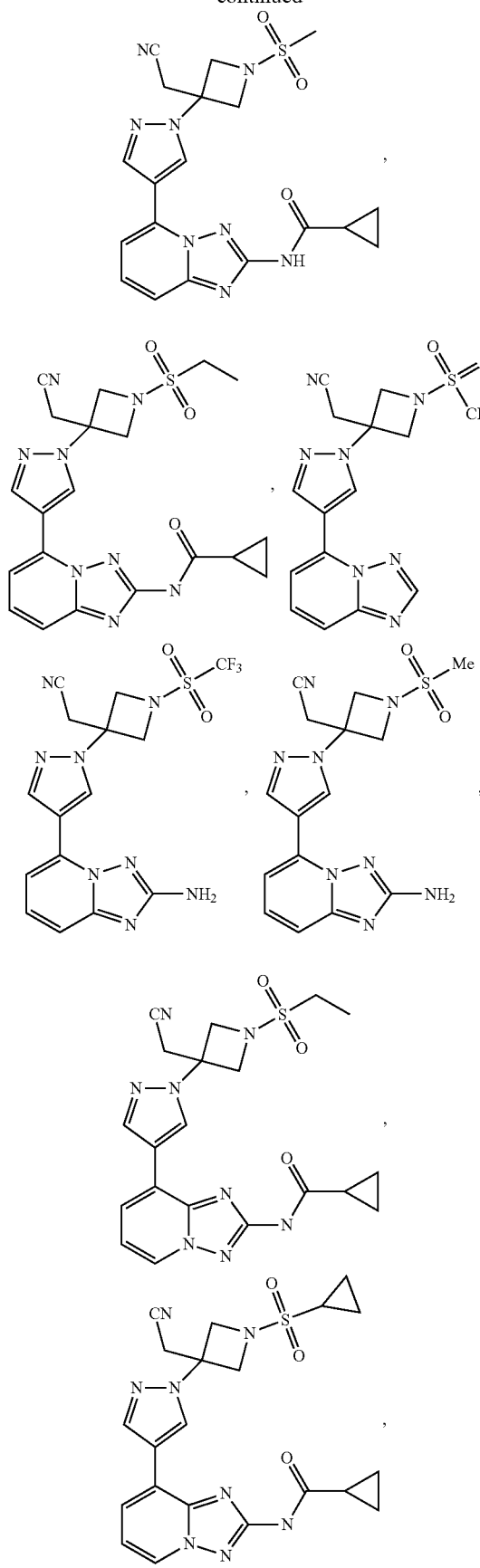
86
-continued
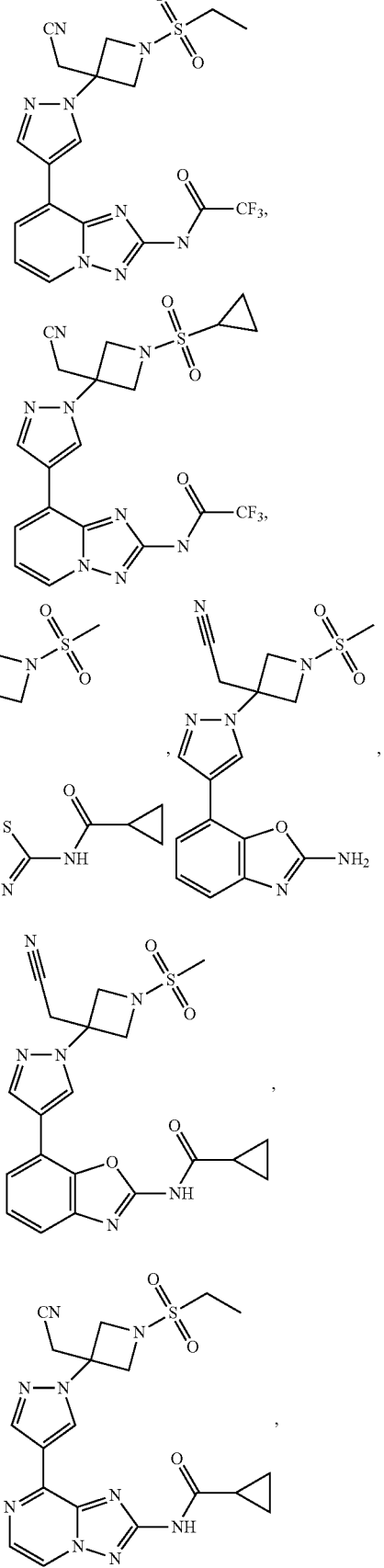

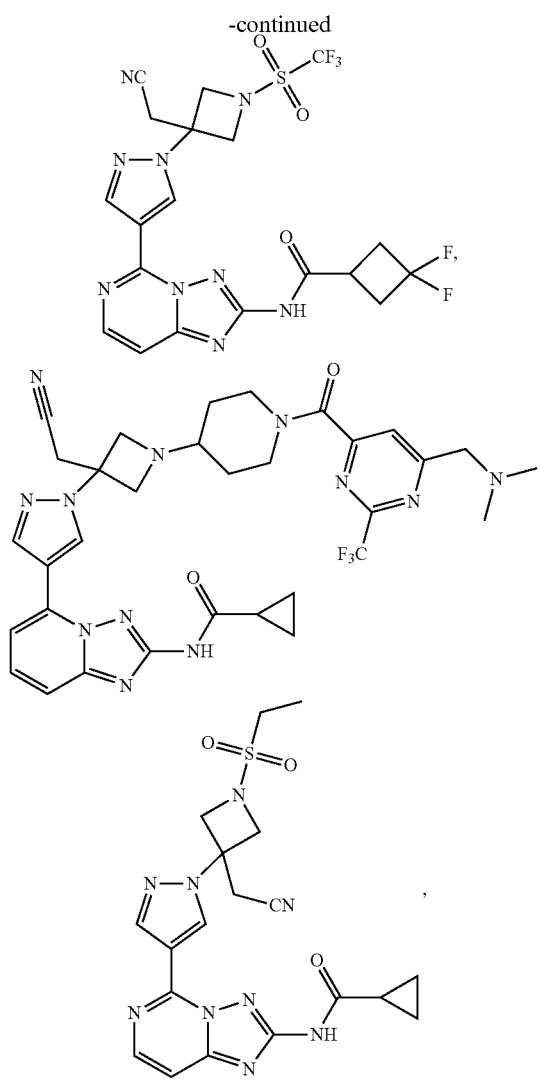
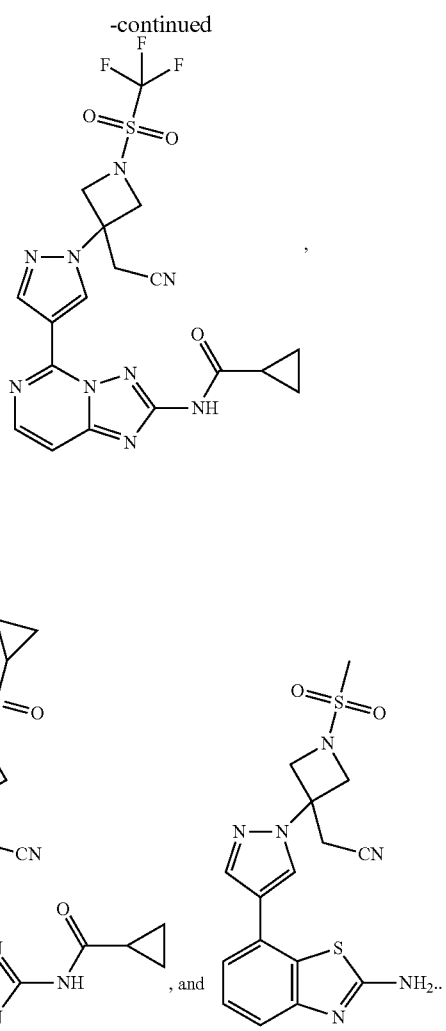

The invention claimed is:

1. A compound of Formula (I):

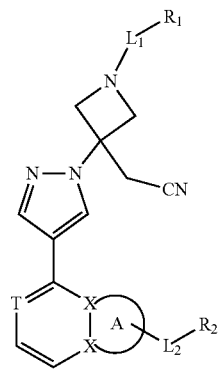

or a pharmaceutically acceptable salt thereof,
wherein:
ring A is 5-6 membered heteroaryl;
$L_1$ and $L_2$ are independently selected from a single bond, —S(=O)$_2$—, —S(=O)—, —C(=O)— or —NHC(=O)—;
$R_1$ is selected from H, $C_{1-6}$ alkyl, $C_{1-6}$ heteroalkyl, $C_{3-7}$ cycloalkyl, 3-7 membered heterocycloalkyl, 5-6 membered aryl or 5-6 membered heteroaryl, wherein the $C_{1-6}$ alkyl, $C_{1-6}$ heteroalkyl, $C_{3-7}$ cycloalkyl, 3-7 membered heterocycloalkyl, 5-6 membered aryl or 5-6 membered heteroaryl is optionally substituted with 1, 2, 3 or 4 R; or $R_1$ is Formula (II):

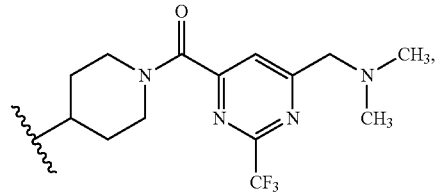

wherein Formula (II) is optionally substituted with 1, 2, 3 or 4 R;
$R_2$ is selected from H, NH$_2$, $C_{1-6}$ alkyl, $C_{1-6}$ heteroalkyl, $C_{3-7}$ cycloalkyl, 3-7 membered heterocycloalkyl, 5-6 membered aryl or 5-6 membered heteroaryl, wherein the $C_{1-6}$ alkyl, $C_{1-6}$ heteroalkyl, $C_{3-7}$ cycloalkyl, 3-7 membered heterocycloalkyl, 5-6 membered aryl or 5-6 membered heteroaryl is optionally substituted with 1, 2, 3 or 4 R;
R is selected from H, halogen, NH$_2$, CN, OH, $C_{1-3}$ alkyl, $C_{1-3}$ heteroalkyl, $C_{3-6}$ cycloalkyl, 3-6 membered heterocycloalkyl, 5-6 membered aryl or 5-6 membered heteroaryl, wherein the $C_{1-3}$ alkyl, $C_{1-3}$ heteroalkyl, $C_{3-6}$ cycloalkyl, 3-6 membered heterocycloalkyl, 5-6 membered aryl or 5-6 membered heteroaryl is optionally substituted with 1, 2, 3 or 4 R';
R' is selected from halogen, OH, CN or NH$_2$;
T is selected from N or C(R); and
each X is independently selected from N or C;
wherein hetero represents 0, 1, 2, 3 or 4 heteroatom(s) or heterogroup(s) independently selected from O, S, N, OH, SH, NH, NH$_2$, C(=O), S(=O) or S(O)$_2$.

2. The compound according to claim 1, or a pharmaceutically acceptable salt thereof, wherein:
R is selected from H, halogen, NH$_2$, CN, OH, $C_{1-3}$ alkyl, $C_{1-3}$ alkoxy or $C_{1-3}$ alkylamino, wherein the $C_{1-3}$ alkyl, $C_{1-3}$ alkoxy or $C_{1-3}$ alkylamino is optionally substituted with 1, 2, 3 or 4 R'.

3. The compound according to claim 1, or a pharmaceutically acceptable salt thereof, wherein:
R is selected from H, F, Cl, Br, I, NH$_2$, CN, OH, CH$_3$, CH$_2$CH$_3$, N(CH$_3$)$_2$ or NHCH$_3$.

4. The compound according to claim 1, or a pharmaceutically acceptable salt thereof, wherein:
$R_1$ is selected from H, $C_{1-3}$ alkyl, $C_{1-3}$ alkyl-O—$C_{1-3}$ alkyl, $C_{1-3}$ alkyl-S—$C_{1-3}$ alkyl, $C_{1-3}$ alkyl-NH—$C_{1-3}$ alkyl, $C_{1-6}$ alkoxy, $C_{1-3}$ alkylamino, $C_{3-6}$ cycloalkyl or $C_{3-6}$ heterocycloalkyl, wherein the $C_{1-3}$ alkyl, $C_{1-3}$ alkyl-O—$C_{1-3}$ alkyl, $C_{1-3}$ alkyl-S—$C_{1-3}$ alkyl, $C_{1-3}$ alkyl-NH—$C_{1-3}$ alkyl, $C_{1-6}$ alkoxy, $C_{1-3}$ alkylamino, $C_{3-6}$ cycloalkyl or $C_{3-6}$ heterocycloalkyl is optionally substituted with 1, 2, 3 or 4 R; or
$R_1$ is Formula (II):

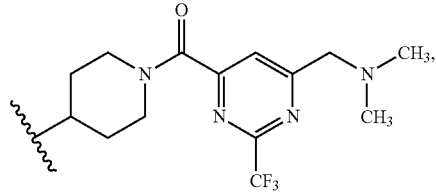

wherein Formula (II) is optionally substituted with 1, 2, 3 or 4 R.

5. The compound according to claim 1, or a pharmaceutically acceptable salt thereof, wherein:
R₁ is selected from H, CH₃, CH₂CH₃, CH₂OCH₃ or cyclopropyl, wherein the CH₃, CH₂CH₃, CH₂OCH₃ or cyclopropyl is optionally substituted with 1, 2, 3 or 4 R; or
R₁ is Formula (II):

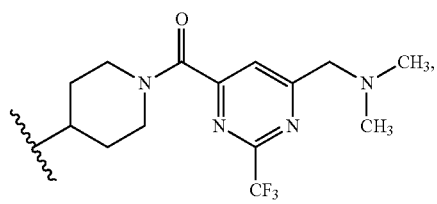

wherein Formula (II) is optionally substituted with 1, 2, 3 or 4 R.

6. The compound according to claim 1, or a pharmaceutically acceptable salt thereof, wherein:
R₁ is selected from H, CH₃, CH₂CH₃, CHF₂, CF₃, CH₂OCH₃ or cyclopropyl; or
R₁ is Formula (II):

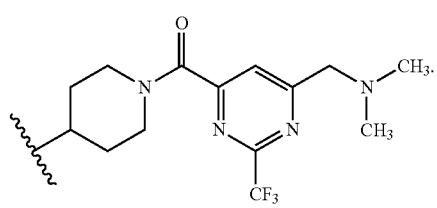

7. The compound according to claim 1, or a pharmaceutically acceptable salt thereof, wherein:
-L₁-R₁ is selected from —H, —S(=O)₂—CH₃, —S(=O)₂—CH₂CH₃, —S(=O)₂-cyclopropyl, —C(=O)-cyclopropyl or —C(=O)—CH₂OCH₃, wherein the S(=O)₂—CH₃, —S(=O)₂—CH₂CH₃, —S(=O)₂-cyclopropyl, —C(=O)-cyclopropyl or —C(=O)—CH₂OCH₃ is optionally substituted with 1, 2, 3 or 4 R; or
-L₁-R₁ is Formula (II):

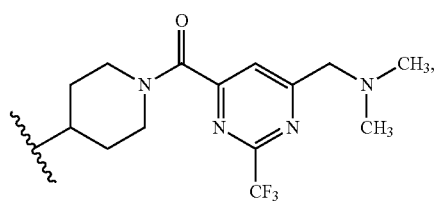

wherein Formula (II) is optionally substituted with 1, 2, 3 or 4 R.

8. The compound according to claim 1, or a pharmaceutically acceptable salt thereof, wherein:
-L₁-R₁ is selected from —H, S(=O)₂—CH₃, —S(=O)₂—CH₂CH₃, —S(=O)₂—CHF₂, —S(=O)₂—CF₃, —S(=O)₂-cyclopropyl, —C(=O)-cyclopropyl or —C(=O)—CH₂OCH₃; or -L₁-R₁ is Formula (II):

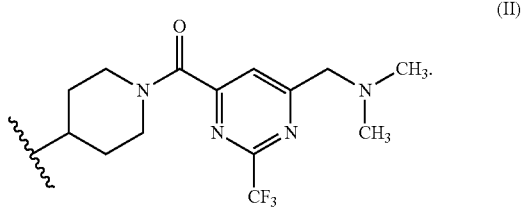 [SMILES: *C1CCN(C(=O)c2cc(CN(C)C)nc(C(F)(F)F)n2)CC1]

9. The compound according to claim 1, or a pharmaceutically acceptable salt thereof, wherein:
R₂ is selected from H, NH₂, C₁₋₃ alkyl, C₁₋₃ alkyl-O—C₁₋₃ alkyl, C₁₋₃ alkyl-S—C₁₋₃ alkyl, C₁₋₃ alkyl-NH—C₁₋₃ alkyl, C₁₋₆ alkoxy, C₁₋₆ alkylamino, C₃₋₆ cycloalkyl or 3-6 membered heterocycloalkyl, wherein the C₁₋₃ alkyl, C₁₋₃ alkyl-O—C₁₋₃ alkyl, C₁₋₃ alkyl-S—C₁₋₃ alkyl, C₁₋₃ alkyl-NH—C₁₋₃ alkyl, C₁₋₆ alkoxy, C₁₋₆ alkylamino, C₃₋₆ cycloalkyl or 3-6 membered heterocycloalkyl is optionally substituted with 1, 2, 3 or 4 R.

10. The compound according to claim 1, or a pharmaceutically acceptable salt thereof, wherein:
R₂ is selected from H, NH₂, CH₃, CH₂OCH₃, cyclopropyl, cyclobutyl or azetidinyl, wherein the CH₃, CH₂OCH₃, cyclopropyl, cyclobutyl or azetidinyl is optionally substituted with 1, 2, 3 or 4 R.

11. The compound according to claim 1, or a pharmaceutically acceptable salt thereof, wherein:
R₂ is selected from H, NH₂, CH₂CN, CF₃, CH₂OCH₃, cyclopropyl, cyclopropan-3-ol, 3,3-difluorocyclobutyl or azetidin-3-yl.

12. The compound according to claim 1, or a pharmaceutically acceptable salt thereof, wherein:
-L₂-R₂ is selected from H, NH₂, —NHC(=O)—CH₃, —NHC(=O)—CH₂OCH₃, —NHC(=O)-cyclopropyl, —NHC(=O)-cyclobutyl or —NHC(=O)-azetidin-3-yl, wherein the —NHC(=O)—CH₃, —NHC(=O)—CH₂OCH₃, —NHC(=O)-cyclopropyl, —NHC(=O)-cyclobutyl or —NHC(=O)-azetidin-3-yl is optionally substituted with 1, 2, 3 or 4 R'.

13. The compound according to claim 1, or a pharmaceutically acceptable salt thereof, wherein:
-L₂-R₂ is selected from H, NH₂, —NHC(=O)—CH₂CN, —NHC(=O)—CF₃, —NHC(=O)—CH₂OCH₃, —NHC(=O)-cyclopropyl, —NHC(=O)-cyclobutan-3-ol, —NHC(=O)-3,3-difluorocyclobutyl or —NHC(=O)-azetidin-3-yl.

14. The compound according to claim 1, or a pharmaceutically acceptable salt thereof, wherein:
ring A is 1,3,4-triazolyl, imidazolyl, oxazolyl or thiazolyl.

15. The compound according to claim 1, or a pharmaceutically acceptable salt thereof, wherein:

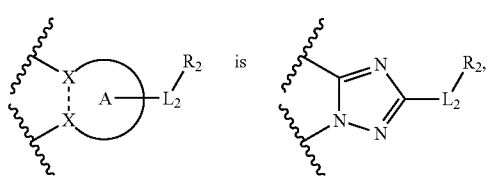

-continued

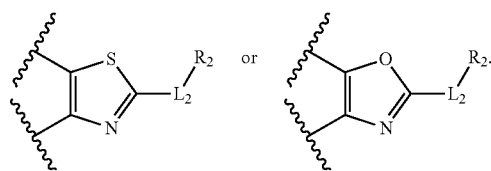

16. The compound according to claim 1, or a pharmaceutically acceptable salt thereof, wherein:

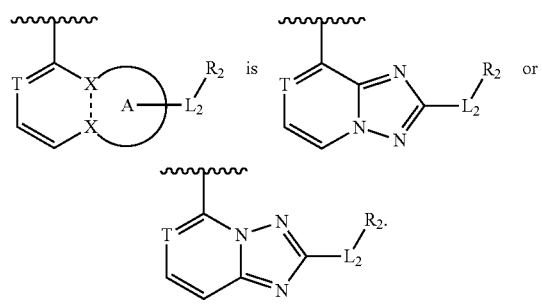

17. The compound according to claim 1, or a pharmaceutically acceptable salt thereof, wherein:

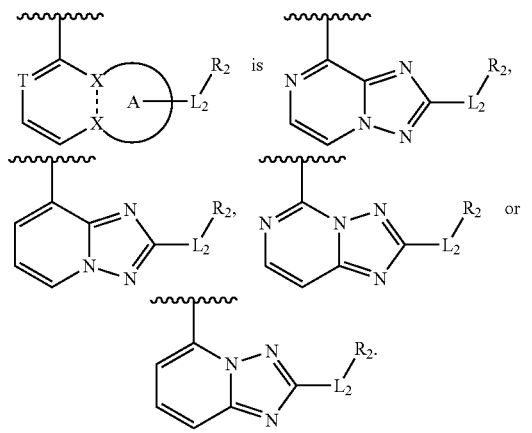

18. The compound according to claim 1, or a pharmaceutically acceptable salt thereof, wherein:

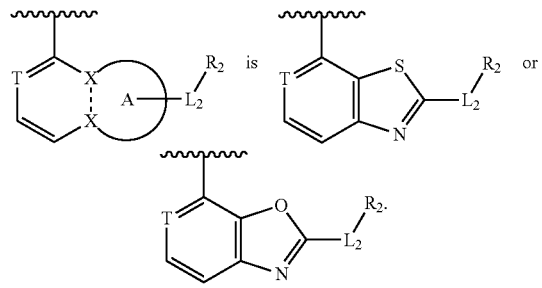

19. The compound according to claim 1, or a pharmaceutically acceptable salt thereof, wherein:

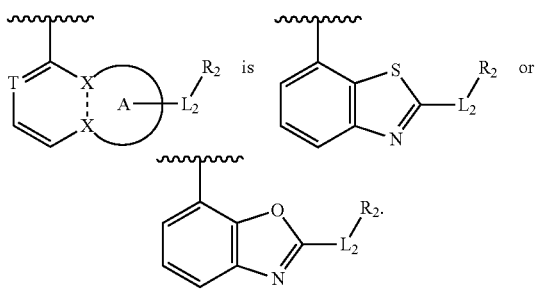

20. The compound according to claim 1, wherein the compound is selected from the group consisting of:

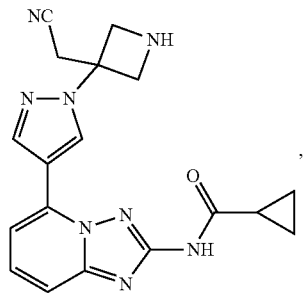

,

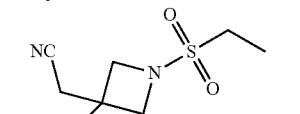

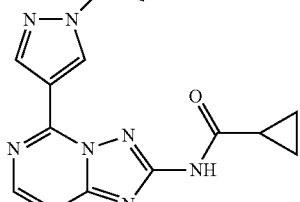

,

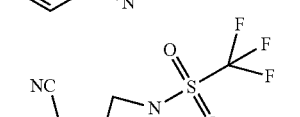

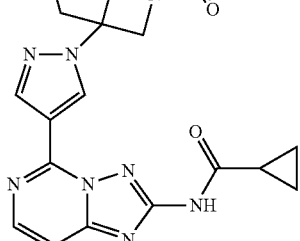

,

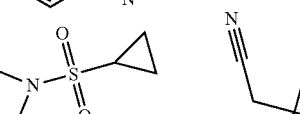

, 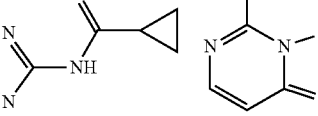,